US012747248B2

(12) United States Patent
Zhu et al.

(10) Patent No.: US 12,747,248 B2
(45) Date of Patent: Sep. 29, 2026

(54) PROCESSES FOR THE PREPARATION OF SUBSTITUTED SPIROOXINDOLE DERIVATIVES

(71) Applicant: ENANTA PHARMACEUTICALS, INC., Watertown, MA (US)

(72) Inventors: Kaicheng Zhu, Belmont, MA (US); Tao Wang, Berkeley Heights, NJ (US); Xin Zhang, Waltham, MA (US); Xiaowen Peng, Sudbury, MA (US); Ruichao Shen, Belmont, MA (US); Jiajun Zhang, Cambridge, MA (US); Wei Li, Lexington, MA (US); Hui Cao, Belmont, MA (US); Xuri Gao, Newtonville, MA (US); Guoqiang Wang, Belmont, MA (US); George G. Wu, Waltham, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 716 days.

(21) Appl. No.: 18/122,892

(22) Filed: Mar. 17, 2023

(65) Prior Publication Data

US 2023/0295175 A1 Sep. 21, 2023

Related U.S. Application Data

(60) Provisional application No. 63/321,244, filed on Mar. 18, 2022.

(51) Int. Cl.
*C07D 487/10* (2006.01)

(52) U.S. Cl.
CPC .................................. *C07D 487/10* (2013.01)

(58) Field of Classification Search
CPC .................................................... C07D 487/10
See application file for complete search history.

(56) References Cited

U.S. PATENT DOCUMENTS

| | | | |
|---|---|---|---|
| 8,222,288 | B2 | 7/2012 | Wang et al. |
| 8,222,425 | B2 | 7/2012 | Britt et al. |
| 8,372,802 | B2 | 2/2013 | Gai et al. |
| 8,546,416 | B2 | 10/2013 | Ambarkhane et al. |
| 9,290,757 | B2 | 3/2016 | Madison |
| 9,309,284 | B2 | 4/2016 | Chang et al. |
| 9,428,739 | B2 | 8/2016 | Colt et al. |
| 9,447,382 | B2 | 9/2016 | Mack |
| 9,474,759 | B2 | 10/2016 | Chang et al. |
| 9,591,858 | B2 | 3/2017 | Valles et al. |
| 9,828,342 | B2 | 11/2017 | Home et al. |
| 9,975,885 | B2 | 5/2018 | St John et al. |
| 10,130,701 | B2 | 11/2018 | Bickerton et al. |
| 10,590,084 | B2 | 3/2020 | Buckman et al. |
| 10,959,969 | B1 | 3/2021 | Johnson |
| 11,013,779 | B2 | 5/2021 | Chang et al. |
| 11,021,513 | B2 | 6/2021 | Schinazi et al. |
| 11,033,600 | B2 | 6/2021 | Chang et al. |
| 11,045,546 | B1 | 6/2021 | Kelly et al. |
| 11,058,763 | B2 | 7/2021 | Zhang et al. |
| 11,058,779 | B2 | 7/2021 | Lu et al. |
| 11,072,787 | B2 | 7/2021 | Wu et al. |
| 11,124,497 | B1 | 9/2021 | Arnold et al. |
| 11,174,231 | B1 | 11/2021 | Arnold et al. |
| 11,207,370 | B2 | 12/2021 | Schinazi et al. |
| 11,319,325 | B1 | 5/2022 | Zhang et al. |
| 11,325,916 | B1 | 5/2022 | Shen et al. |
| 11,339,170 | B1 | 5/2022 | Gao et al. |
| 11,352,363 | B1 | 6/2022 | Wang et al. |
| 11,358,953 | B2 | 6/2022 | Panarese et al. |

(Continued)

FOREIGN PATENT DOCUMENTS

| | | |
|---|---|---|
| CN | 114057624 A | 2/2022 |
| CN | 115894504 A | 4/2023 |

(Continued)

OTHER PUBLICATIONS

PubChem, SID 332063528, Deposited Apr. 10, 2017. [Retrieved on Feb. 21, 2024] online at https://pubchem.ncbi.nlm.nih.gov/substance/332063528.

Chen, L. , "Design, Synthesis, Characterization, and Biological Activities of Novel Spirooxindole Analogues Containing Hydantoin, Thiohydantoin, Urea, and Thiourea Moieties", J. Agric. Food Chem., 68(39), https://doi.org/10.1021/acs.jafc.0c04488, Aug. 31, 2020, 10618-10625.

Owen, D. R, "An oral SARS-CoV-2 Mpro inhibitor clinical candidate for the treatment of COVID-19", Science, 374(6575), doi: 10.1126/science.abl4784, Dec. 24, 2021, 1586-1593.

Panarese, Joseph D. et al., U.S. Appl. No. 18/102,850, filed Jan. 30, 2023.

Pubchem, SID 160923150, deposited Mar. 4, 2013.

Pubchem, SID 267351747, deposited Dec. 11, 2015.

(Continued)

*Primary Examiner* — Matthew P Coughlin

(74) *Attorney, Agent, or Firm* — Edgar W. Harlan; Carolyn S. Elmore; Elmore Patent Law Group, P.C.

(57) ABSTRACT

The present invention relates to processes for preparing a compound of Formula (A):

(A)

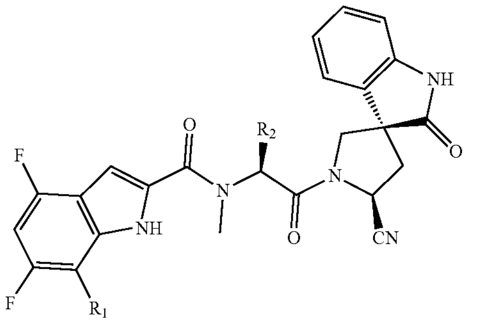

or a pharmaceutically acceptable salt or solvate thereof. Compound of Formula (A) and pharmaceutical compositions are useful as SARS-CoV-2 3CL pro inhibitors.

12 Claims, 3 Drawing Sheets

(56) References Cited

U.S. PATENT DOCUMENTS

| | | | |
|---|---|---|---|
| 11,384,090 B2 | 7/2022 | Wang et al. | |
| 11,858,945 B2 | 1/2024 | Panarese et al. | |
| 11,912,714 B2 | 2/2024 | Cao et al. | |
| 11,919,910 B2 | 3/2024 | Wang et al. | |
| 2005/0143320 A1 | 6/2005 | Yang et al. | |
| 2006/0014821 A1 | 1/2006 | He et al. | |
| 2008/0125430 A1 | 5/2008 | Wang et al. | |
| 2009/0137818 A1 | 5/2009 | Hilgenfeld et al. | |
| 2010/0272681 A1 | 10/2010 | Farmer et al. | |
| 2010/0317661 A1 | 12/2010 | Wang et al. | |
| 2013/0072500 A1 | 3/2013 | Banka et al. | |
| 2013/0072686 A1 | 3/2013 | Cadieux et al. | |
| 2014/0148494 A1 | 5/2014 | Wang et al. | |
| 2014/0243341 A1 | 8/2014 | Chang et al. | |
| 2014/0378680 A1 | 12/2014 | Wang et al. | |
| 2015/0133368 A1 | 5/2015 | Chang et al. | |
| 2015/0336928 A1 | 11/2015 | Fang et al. | |
| 2016/0014821 A1 | 1/2016 | Toebes | |
| 2017/0044183 A1 | 2/2017 | Lim et al. | |
| 2018/0099981 A1 | 4/2018 | Estrada et al. | |
| 2019/0161472 A1 | 5/2019 | Ombrato et al. | |
| 2020/0230198 A1 | 7/2020 | Chang et al. | |
| 2020/0354379 A1* | 11/2020 | Donald | A61P 31/12 |
| 2021/0355111 A1 | 11/2021 | Arnold et al. | |
| 2022/0033383 A1 | 2/2022 | Panarese et al. | |
| 2022/0041652 A1 | 2/2022 | Panarese et al. | |
| 2022/0048944 A1 | 2/2022 | Panarese et al. | |
| 2022/0162216 A1 | 5/2022 | Wang et al. | |
| 2022/0162231 A1 | 5/2022 | Wang et al. | |
| 2022/0380377 A1 | 12/2022 | Zhang et al. | |
| 2022/0402926 A1 | 12/2022 | Zhang et al. | |
| 2023/0103494 A1 | 4/2023 | Wang et al. | |
| 2023/0115107 A1 | 4/2023 | Gao et al. | |
| 2023/0122228 A1 | 4/2023 | Shen et al. | |
| 2023/0151019 A1 | 5/2023 | Cao et al. | |
| 2023/0159545 A1 | 5/2023 | Panarese et al. | |
| 2023/0159546 A1 | 5/2023 | Kass et al. | |
| 2023/0174531 A1 | 6/2023 | Panarese et al. | |
| 2023/0174542 A1 | 6/2023 | Panarese et al. | |
| 2023/0203048 A1 | 6/2023 | Wang et al. | |
| 2023/0295175 A1 | 9/2023 | Zhu et al. | |
| 2023/0331734 A1 | 10/2023 | Cao et al. | |
| 2024/0132512 A1 | 4/2024 | Zhu et al. | |

FOREIGN PATENT DOCUMENTS

| | | | | |
|---|---|---|---|---|
| EP | 4159211 A1 | 4/2023 | | |
| EP | 4209494 A1 | 7/2023 | | |
| GB | 2595975 A | 12/2021 | | |
| WO | WO-9509828 A1 * | 4/1995 | C07C 17/263 | |
| WO | 0059929 A1 | 10/2000 | | |
| WO | 0208244 A2 | 1/2002 | | |
| WO | 2004101742 A3 | 6/2005 | | |
| WO | 2005113580 A1 | 12/2005 | | |
| WO | 2006061714 A2 | 6/2006 | | |
| WO | 2006061714 A3 | 8/2006 | | |
| WO | 2007038138 A2 | 4/2007 | | |
| WO | 2008144507 A2 | 11/2008 | | |
| WO | 2012099454 A1 | 7/2012 | | |
| WO | 2013049382 A1 | 5/2013 | | |
| WO | 2013166319 A1 | 11/2013 | | |
| WO | 2017222935 A1 | 12/2017 | | |
| WO | 2018023054 A1 | 2/2018 | | |
| WO | 2018042343 A2 | 3/2018 | | |
| WO | 2019086141 A1 | 5/2019 | | |
| WO | 2019086142 A1 | 5/2019 | | |
| WO | 2020081636 A1 | 4/2020 | | |
| WO | 2020221826 A1 | 11/2020 | | |
| WO | 2021205296 A1 | 10/2021 | | |
| WO | 2021206876 A1 | 10/2021 | | |
| WO | 2021206877 A1 | 10/2021 | | |
| WO | 2021207409 A2 | 10/2021 | | |
| WO | 2021226546 A1 | 11/2021 | | |
| WO | 2021250648 A1 | 12/2021 | | |
| WO | 2021252491 A1 | 12/2021 | | |
| WO | 2021252644 A1 | 12/2021 | | |
| WO | 2022013684 A1 | 1/2022 | | |
| WO | 2022020242 A1 | 1/2022 | | |
| WO | 2022020711 A1 | 1/2022 | | |
| WO | 2022021841 A1 | 2/2022 | | |
| WO | 2022070048 A1 | 4/2022 | | |
| WO | 2022109363 A1 | 5/2022 | | |
| WO | 2022159644 A1 | 7/2022 | | |
| WO | 2022235605 A1 | 11/2022 | | |
| WO | 2022251615 A1 | 12/2022 | | |
| WO | 2022256434 A1 | 12/2022 | | |
| WO | 2023086350 A1 | 5/2023 | | |
| WO | 2023109926 A1 | 6/2023 | | |
| WO | 2024076680 A1 | 4/2024 | | |

OTHER PUBLICATIONS

Pubchem, SID 367622864, May 25, 2018.

Pubchem, SID 326247498, deposited Jan. 25, 2017.

"1-(2-oxospiro[1H-indole-3,3'-pyrrolidine]-1'-yl)-4-pyridin-2-ylbutane-1,4-dione", Pubchem CID 145894940. Create Date: Feb. 12, 2020. Date Accessed: Jun. 9, 2023, 2 pgs.

Anonymous, "Nirmatrelvir", Cortellis Database, Retrieved from the Internet: URL:https://www.cortellis.com/drugdiscovery/entity/drug/1126756/product?ent=qR5ruNw5&updateHistoryPage=5&orderBy=_score:desc, Nov. 8, 2022, 3 pgs.

Anonymous, "Pfizer Initiates Phase 1 Study of Novel Oral Antiviral Therapeutic Agent Against SARS-CoV-2 Science Products Stories Newsroom About", Retrieved from the Internet: URL:https://www.pfizer.com/news/press-release/press-release-detail/pfizer-initiatesphase-1-study-novel-oral-antiviral [retrieved on Nov. 11, 2022].

Bafna, K., et al., "Structural Similarity of SARS-CoV2 Mpro and HCV NS3/4A Proteases Suggests New Approaches for Identifying Existing Drugs Useful as COVID-19 Therapeutics", , ChemRxiv online at DOI: 10.26434/chem rxiv.12153615. v1, 2020.

Baker, J. D, et al., "A drug repurposing screen identifies hepatitis C antivirals as inhibitors of the SARS-CoV-2 main 1 protease", BioRxiv. Preprint. avail at https://doi.org/10.1101/2020.07.10.197889, Jul. 10, 2020.

Chia, C.S. Brian, "Novel Coronavirus Main Protease Di- and Tripeptide Inhibitors for Treating COVID-19", ACS Med. Chem. Lett., 13(9), URL:https://pubs.acs.org/doi/pdf/10.1021/acsmedchemlett.2c00332, Aug. 8, 2022, 1388-1389.

Chuck, C-P, et al., "Design, synthesis and crystallographic analysis of nitrile-based broad-spectrum peptidomimetic inhibitors for coronavirus 3C-like proteases", Euro. J. Med. Chem., 59, https://doi.org/10.1016/j.ejmech.2012.10.053, 1-6, 2012.

Dai, W., et al., "Structure-based design of antiviral drug candidates targeting the SARS-CoV-2 main protease", Science, 368(6497), DOI: 10.1126/science. abb4489, 1331-1334, 2020.

Efremov, I., et al., "Discovery and Optimization of a Novel Spiropyrrolidine Inhibitor of B-Secretase (BACE1) through Fragment-Based Drug Design", J. Med. Chem., 55, 9069-9088, 2012.

Halford, B., "Pfizer unveils its oral SARS-00V-2 inhibitor—The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/99/i13(a version appeared in 99(13)), 2 pgs, 2021.

Halford, B., "Pfizer's novel COVID-19 antiviral heads to clinical trials—The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, 2 pgs, 2020.

Kelemen, A., et al., "Spiro[pyrrolidine-3,3'-oxindoles] and Their Indoline Analogues as New 5-HT6 Receptor Chemotypes", Molecules, 22, DOI: 10.3390/molecules22122221, 1-25, 2017.

Konno, S., et al., "3CL Protease Inhibitors with an Electrophilic Arylketone Moiety as Anti-SARS-CoV-2 Agents", J. Medicinal Chemistry, https://doi.org/10.1021/acs.jmedchem.1c00665, pp. 1-14, 2021.

Lee, C., et al., "Structural Basis of Inhibition Specificities of 3C and 3C-like Proteases by Zinc-coordinating and Peptidomimetic Compounds", J. Biological Chem., 284(12), 7646-7655, 2009.

(56) References Cited

OTHER PUBLICATIONS

Mandadapu, S., et al., "Macrocyclic Inhibitors of 3c and 3C-Like Proteases of Picornavirus, Norovirus, and Coronavirus", Bioorg. & Med. Chem. Lett., 23, http:lfdx.doi.org/10.1016/j.bmcl.2013.05.021, 3709-3712, 2013.
Marti, C., "Novel Approach to Spiro-Pyrrolidine-Oxindoles and its Application to the Synthesis of (+−)-Horsfiline and (−)-Spirotryprostatin", ETH Library, Doctoral Thesis, https://doi.org/10.3929/ethz-a-004489068, 1-2, 23-25, 2003.
Owen, D., "Oral inhibitors of the 1-12 SARS-CoV-2 main protease for the treatment of COVID-19", 261ST Am. Chem. Soc. (ACS) Natl Meet, 1 pg, 2021.
Thanigaimalai, P., et al., "Design, synthesis, and biological evaluation of novel dipeptide-type SARS-CoV 3CL protease inhibitors: Structure-activity relationship study", Euro J. Med. Chem., 65, DOI: 10.1016/J.EJMECH.2013.05.005, 436-447, 2013.
Vandyck, K., et al., "Considerations for the discovery and development of 3-chymotrypsin-like cysteine protease inhibitors targeting SARS-CoV-2 infection", Current Opinion in Virology, 49, DOI: 10.1016/j.coviro.2021.04.006, 36-40, 2021.
Wang, Y., et al., "Inhibition of Enterovirus 71 Replication by an a-Hydroxy-Nitrile Derivative NK-1.9k", Antiviral Res., 141, 91-100, 2017.
Xu, J., et al., "Green Oxidation of Indoles Using Halide Catalysis", Nature Communications, 10:4754, https://doi.org/10.1038/s41467-019-12768-4, 1-11, 2019.
Yang, S., et al., "Synthesis, Crystal Structure, Structure-Activity Relationships, and Antiviral Activity of a Potent SARS Coronavirus 3CL Protease Inhibitor", J. Med. Chem., 49, 4971-4980, 2006.
Zhai, Y., et al., "Cyanohydrin as an Anchoring Group for Potent and Selective Inhibitors of Enterovirus 71 3C Protease", J. Med. Chem., 58, 9414-9420, 2015.
Zhang, L., et al., "a-Ketoamides as Broad-Spectrum Inhibitors of Coronavirus and Enterovirus Replication: Structue-Based Design, Synthesis, and Activity Assessment", J. Med. Chem., 63, https://dx.doi.org/10.1021/acs,jmedchem.9b01828, 4562-4578, 2020.
Zhou, L., et al., "An Overview of Spirooxindole as a Promising Scaffold for Novel Drug Discovery", Expert Opinion on Drug Discovery, 15(5), 603-625, 2020.
Ziarani, G., et al., "Synthesis of Spiro-Fused Heterocyclic Scaffolds Through Multicomponent Reactions Involving Isatin", ARKIVOC, 2016 (i), http://dx.doi.org/10.3998/ark.5550190.p009.385, 1, 14-16.
Hati, S., "Spiro[pyrrolidine-3, 1-7 3'-oxindole] as potent anti-breast cancer compounds: Their design, synthesis, biological evaluation and cellular target identification", Sci Reports, 6(1), DOI: 10.1038/srep32213, Aug. 30, 2016, 10 pgs.
Pellegrini, "Synthesis of the Oxindole Alkaloid (−)-Horsfiline", Tetrahedron Asymmetry 5(10), Oct. 1994, 1979-1992.
Pellegrini, "Synthesis of the Oxindole Alkaloid (−)-Horsfiline", Tetrahedron Asymmetry 5(10), Abstract only, Oct. 1994, 1.

* cited by examiner

PROCESSES FOR THE PREPARATION OF SUBSTITUTED SPIROOXINDOLE DERIVATIVES

RELATED APPLICATION

This application claims the benefit of U.S. Provisional Application No. 63/321,244, filed on Mar. 18, 2022. The entire teachings of the above application are incorporated herein by reference.

TECHNICAL FIELD

The present invention relates generally to the processes and intermediates useful in the preparation of biologically active molecules, especially in the synthesis of certain SARS-CoV-2 3CLpro inhibitors.

BACKGROUND OF THE INVENTION

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO 2004101742 A2, US 2005/0143320 A1, US 2006/0014821 A1, US 2009/0137818 A1, WO 2013049382 A2, WO 2013166319 A1, WO2018042343, WO2018023054, WO 2022013684, WO 2021252644, WO2022020711, WO 2022020242, U.S. Pat. No. 11,174,231 B1, U.S. Pat. No. 11,124,497 B1, WO 2005113580, and WO2006061714).

There is a need in the art for novel therapeutic agents that treat, ameliorate or prevent SARS-CoV-2 infection. The present invention provides the process of novel compounds which act in inhibiting or preventing SARS-CoV-2 viral replication and thus are used in the treatment of COVID-19 (see PCT/US21/60247).

Synthesis of substituted spirooxindole and its intermediate has been previously published (Refer to PCT/US21/60247, WO2019086142, WO 2020221811, WO2020221826, J. Med. Chem. 2012, 55, 9069). However, the scale-up using previous process is very challenging due to the safety concern associated with certain intermediates, instability of certain intermediates as well as lack of purification process other than column chromatograph. Thus, there is a strong need for developing a safe and efficient processes for the large-scale preparation of these novel substituted spirooxindole derivatives.

SUMMARY OF THE INVENTION

The present invention provides methods for preparing compounds of Formula (A):

(A)

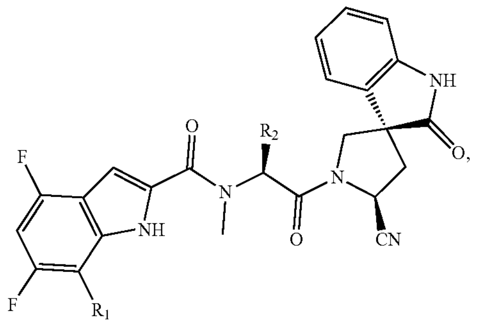

wherein $R_1$ is selected from the group consisting of hydrogen, Cl, F, optionally substituted methyl, and optionally substituted methoxy; and $R_2$ is selected from the group consisting of hydrogen, optionally substituted —$C_1$-$C_6$ alkyl, and optionally substituted —$C_1$-$C_6$alkylaryl. Preferably, $R_1$ is H or F; and $R_2$ is isobutyl, cyclopropylmethyl, 2,2-dimethylpropyl, or benzyl. More preferably, $R_1$ is F; and $R_2$ is isobutyl.

The invention further relates to methods with increased product yield and improved scalability for large scale production of a compound of Formula (A).

In certain embodiments, the present invention relates to processes for isolating a compound of Formula (A) as a toluene solvate or an amorphous solid.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
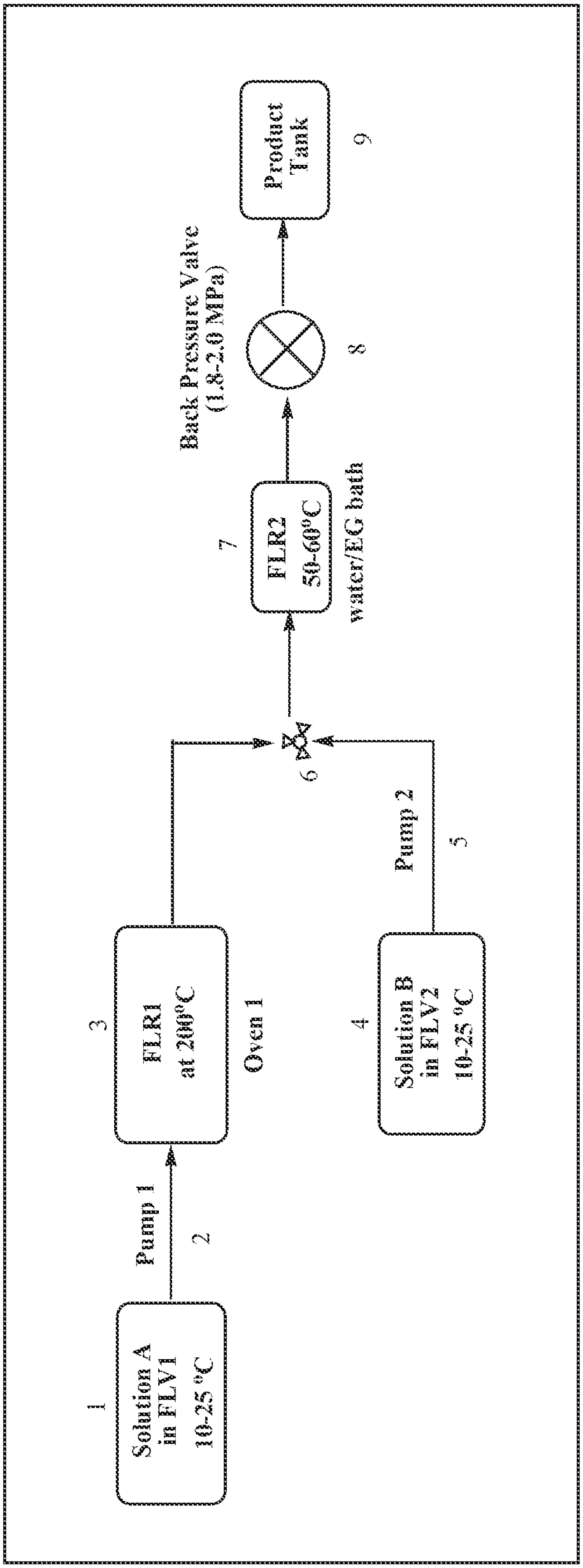
FIG. 1 is a schematic of the flow reaction process described in Example 9.

The present invention provides methods for preparing a compound of Formula (A), (A)

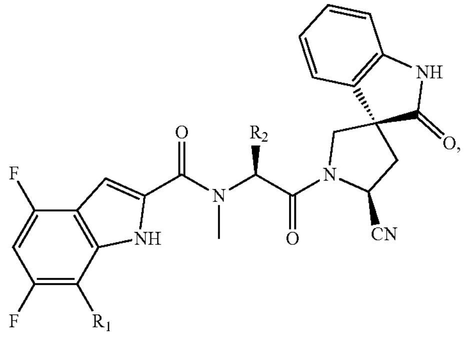

wherein $R_1$ is selected from the group consisting of hydrogen, Cl, F, optionally substituted methyl, and optionally substituted methoxy; and $R_2$ is selected from the group consisting of hydrogen, optionally substituted —$C_1$-$C_6$ alkyl, and optionally substituted —$C_1$-$C_6$ alkylaryl. Preferably, $R_1$ is H or F; and $R_2$ is isobutyl, cyclopropylmethyl, 2,2-dimethylpropyl or benzyl. More preferably, $R_1$ is F; and $R_2$ is isobutyl.

In preferred embodiments, the compound of Formula (A) is represented by Formula (A-I):

(A-I)

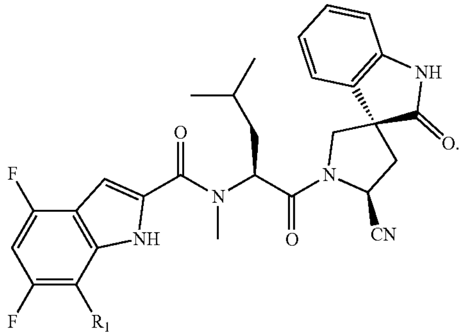

In one embodiment the compound of Formula (A) is Compound (I):

(I)

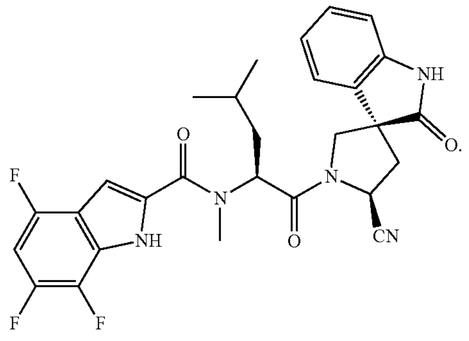

In one embodiment, the process for preparing a compound of Formula (A) comprises the steps of:

(a) reacting a compound of Formula (W) with formaldehyde, to produce a compound of Formula (B):

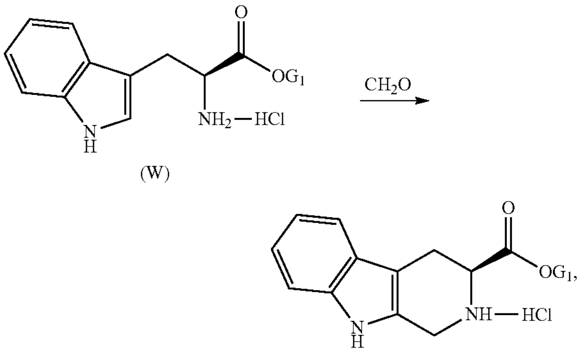

(W)

(B)

wherein $G_1$ is $C_1$-$C_6$-alkyl or aryl, preferably methyl, ethyl or phenyl, and more preferably methyl;

(b) converting the compound of Formula (B) to a compound of Formula (C):

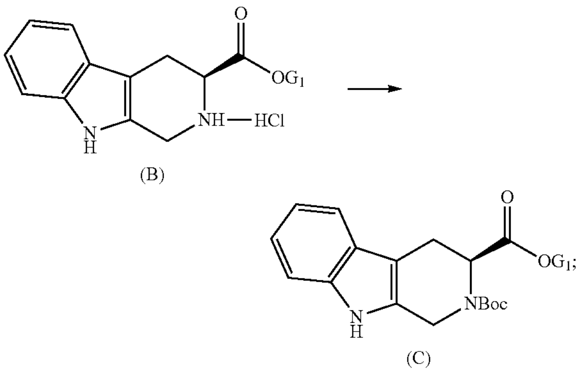

(B)

(C)

(c) subjecting the compound of Formula (C) to rearrangement to produce a compound of Formula (D-1):

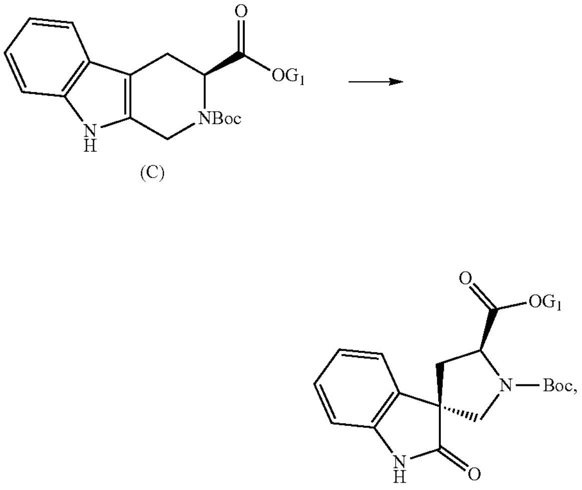

(C)

(D-1)

(d) converting the compound of Formula (D-1) to a compound (e-1):

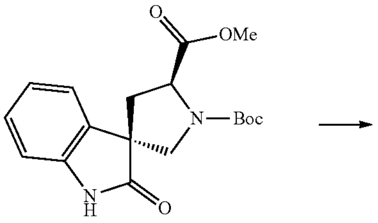

(D-1)

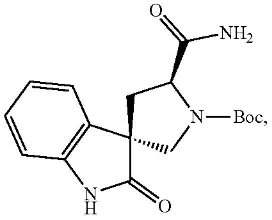

(e-1)

(e) converting Compound (e-1) to a compound of Formula (F-1):

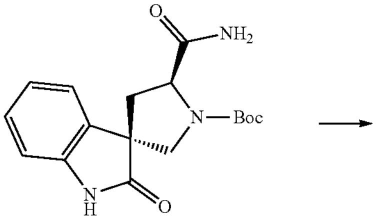

(e-1)

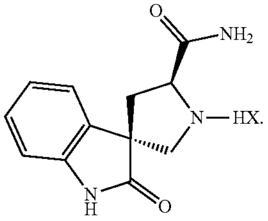

(F-1)

wherein X is an anion selected from $Cl^-$, $Br^-$, and $CF_3CO_2^-$, preferably X is $Cl^-$;

(f) reacting the compound of Formula (F-1) with a compound of Formula (K)

(K)

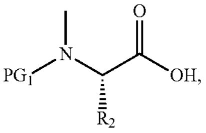

wherein $PG_1$ is selected from -Boc, -Cbz, —C(O)OMe, —C(O)OEt, -Fmoc, -Troc, -Moz, -Pnz, and -Teoc, preferably $PG_1$ is -Boc or -Cbz, more preferably $PG_1$ is -Cbz; and $R_2$ is as previously defined and is preferably isobutyl; to produce a compound of Formula (L):

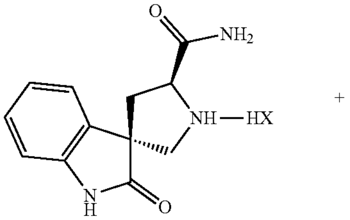

(F-1)

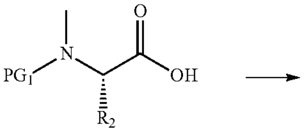

(K)

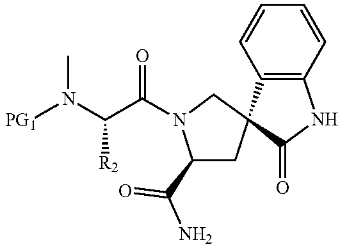

(L)

(g) converting the compound of Formula (L), optionally in the presence of a suitable acid, to a compound of Formula (M) or a salt thereof:

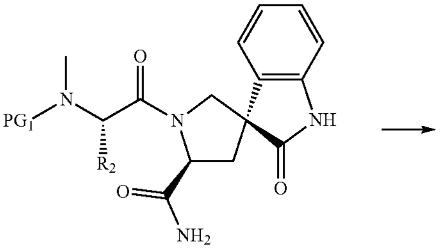

(L)

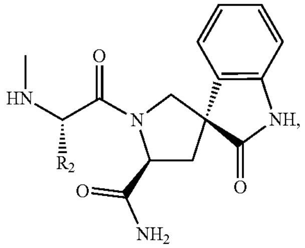

(M)

(h) Reacting the compound of Formula (M) or salt thereof with a compound of Formula (J) or a salt thereof,

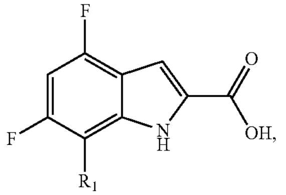

(J)

wherein $R_1$ is as previously defined and is preferably hydrogen or F, to provide a compound of Formula (N):

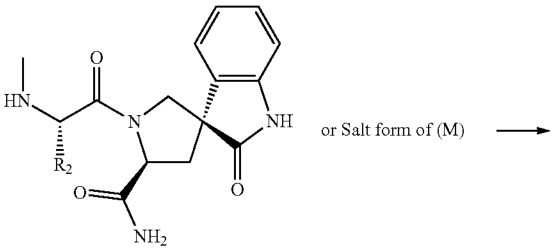

(M)

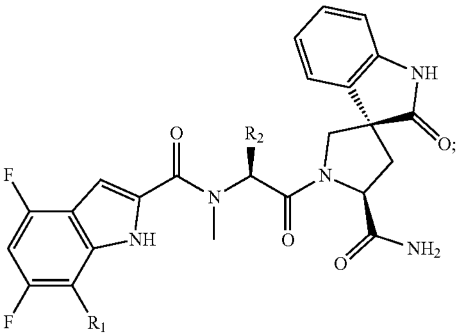

(N)

and (i) converting the compound of Formula (N) to the compound of Formula (A):

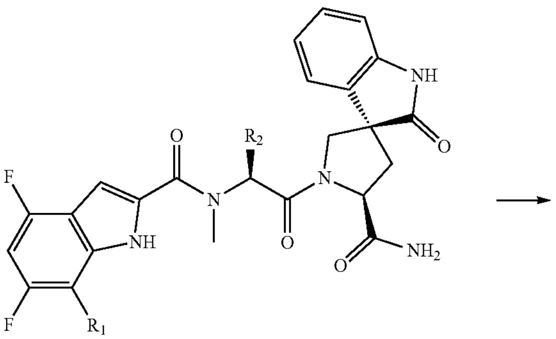

(N)

-continued

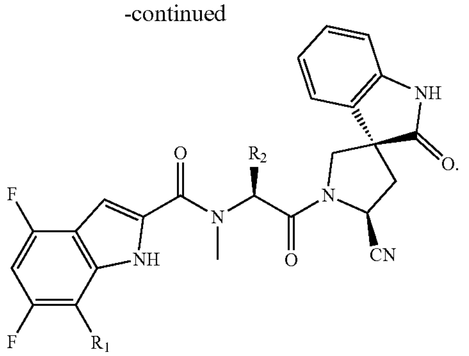

(A)

In one preferred embodiment of the foregoing process, $R_1$ is F, $R_2$ is isobutyl, $G_1$ is methyl, X is $Cl^-$, and $PG_1$ is Cbz.

Step (a)

In preferred embodiments, step (a) occurs in a suitable solvent, such as, but not limited to, methanol, t-butyl alcohol, acetonitrile, acetone, dichloromethane, chloroform, dimethylformamide, dimethylsulfoxide, dioxane, ethyl acetate, heptane, hexane, methyl t-butyl ether, tetrahydrofuran, and toluene, or a mixture of two or more thereof. Preferably the solvent is methanol.

In one embodiment, the reaction is conducted at a temperature from about 0° C. to about 100° C., preferably from about 45° C. to about 85° C., and more preferably about 65° C. In one embodiment, step a) takes place for a period from about half an hour to about 1 day, preferably about half an hour to about 5 hours, and more preferably about 1 hour.

In a preferred embodiment, the process of the invention further comprises isolating Compound of Formula (B), preferably in a substantially pure form.

Step (b)

In step (b) Compound (b) is reacted with a suitable Boc protection agent, such as, but not limited to tert-butyl phenyl carbonate, di-tert-butyl dicarbonate, N-(tert-butoxycarbonyloxy)phthalimide or 1-tert-butoxycarbonyl-1,2,4-triazole. Preferably the Boc protection reagent is di-tert-butyl dicarbonate (Boc anhydride).

Step (b) preferably occurs in the presence of a suitable base, such as, but not limited to, triethylamine, diisopropylethylamine, sodium bicarbonate or N-methylmorpholine. A preferred base is triethylamine.

In preferred embodiments, step (b) occurs in a solvent. A suitable solvent is included, but not limited to 2-Me THF, t-butyl alcohol, acetonitrile, acetone, dichloromethane, chloroform, dimethyl formamide, dimethyl sulfoxide, dioxane, ethyl acetate, heptane, hexane, methyl t-butyl ether, tetrahydrofuran, water, and toluene, or a mixture of two or more thereof. Preferably the solvent is 2-Me THE and water as co-solvent. Preferably the volume ratio of 2-Me THE to water is 4:1.

In one embodiment, the reaction of step (b) is conducted at a temperature from about −10° C. to about 60° C., preferably from about 0° C. to about 40° C., and more preferably about 5° C. to about 25° C. In one embodiment, step (b) takes place for a period from about 1 hour to about 24 hours, preferably about 1 hour to about 10 hours, and more preferably about 5 hours.

In a preferred embodiment, the process of the invention further comprises isolating the compound of Formula (C), preferably in a substantially pure form.

Step (c)

In step (c), the compound of Formula (C) is reacted with an oxidizing agent to produce the compound of Formula (D-1). In certain embodiments this reaction also produces the compound of Formula (D-2), which is a diastereomer of the compound of Formula (D-1).

(D-1)

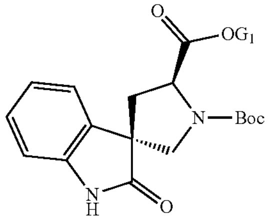

(D-2)

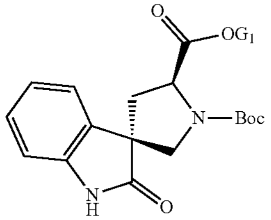

Preferably the reaction produces the compound of Formula (D-1) in diastereomeric excess. The weight ratio of the compound of Formula (D-1) and the compound of Formula (D-2) produced is preferably from about from 55:45 to 95:5, and more preferably is from about 6:1 to about 8:1.

Suitable oxidizing agents include, but are not limited to, N-bromosuccinimide (NBS), hydrogen peroxide, meta-chloroperoxybenzoic acid (m-CPBA), potassium peroxymonosulfate (Oxone), 1-chloromethyl-4-fluoro-1,4-diazoniabicyclo[2.2.2]octane bis(tetrafluoroborate) (Selecfluor), tert-butyl hypochlorite, N-iodosuccinimide (NIS), or the like. A preferred oxidizing agent is N-bromosuccinimide (NBS).

In certain embodiments, step (c) occurs in the presence of a suitable acid, such as, but not limited to, acetic acid, formic acid, trifluoroacetic acid, benzoic acid, hydrochloride acid, phosphonic acid, sulfuric acid, p-toluenesulfonic acid, or the like. A preferred acid is acetic acid.

In preferred embodiments of step (c), the oxidizing agent is N-bromosuccinimide (NBS) and the acid is acetic acid.

In preferred embodiments, step (c) occurs in a in a solvent. A suitable solvent is included, but not limited to dichloromethane, chloroform, dioxane, ethyl acetate, heptane, hexane, methyl t-butyl ether, tetrahydrofuran (THF), 2-Me THF, water and toluene, or a mixture of two or more thereof. Preferably the solvent is a mixture of 2-Me THF, THF and water. Preferably the volume ratio of 2-Me THF/TiF/water is around 3.5/1.5/1.

In one embodiment, the reaction is conducted at a temperature from about −40° C. to about 30° C., preferably from about −30° C. to about −10° C., and more preferably about −30° C. In one embodiment, step (c) takes place for a period from about 30 minutes to about 3 hours, preferably about 30 minutes to about 1 hours, and more preferably about 30 min.

In one embodiment, the compound of Formula (D-1) is the major product. In a preferred embodiment, the process of the invention further comprises isolating the compound of Formula (D-1) and the compound of Formula (D-2).

Step (d)

The compound of Formula (D-1) is converted to the compound of Formula (e-1) by reaction with an ammonolysis reagent. In certain embodiments, in step (d), the compound of Formula (D-1) is reacted with the ammonolysis reagent as a mixture with the compound of Formula (D-2), resulting in production of both Compound (e-1) and Compound (e-2).

(e-1)

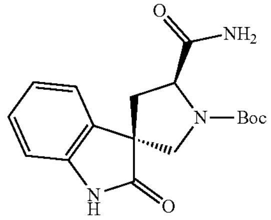

(e-2)

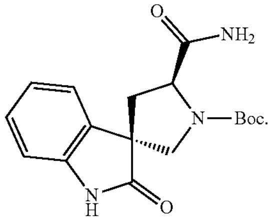

In certain embodiments of step (d), Compound (e-1) is produced in diastereomeric excess. In certain embodiments, the weight ratio of Compound (e-1) and Compound (e-2) produced is about from 55:45 to 95:5, preferably from about 6:1 to 8:1.

Suitable ammonolysis reagents include, but are not limited to, ammonia, ammonium hydroxide, and the like. A preferred ammonolysis reagent is ammonia.

In preferred embodiments, step (d) occurs in a solvent. A suitable solvent is included, but not limited to dichloromethane, chloroform, dioxane, ethyl acetate, heptane, hexane, methyl t-butyl ether, tetrahydrofuran, methanol, ethanol, propanol and toluene, or a mixture of two or more thereof. Preferably the solvent is methanol.

In one embodiment, the reaction is conducted at a temperature from about 20° C. to about 60° C., preferably from about 40° C. to about 60° C., and more preferably about 45° C. In one embodiment, step (d) takes place for a period from about 2 days to about 7 days, preferably about 3 days to about 5 days, and more preferably about 5 days.

In one embodiment, Compound (e-1) is the major product. In a preferred embodiment, the process of the invention further comprises isolating Compound (e-1) and Compound (e-2).

Step (e)

In certain embodiments of step (e), Compound (e-1) is reacted with an acid as a mixture with Compound (e-2) to produce a mixture of a compound of Formula (F-1) and a compound of Formula (F-2):

(F-1)

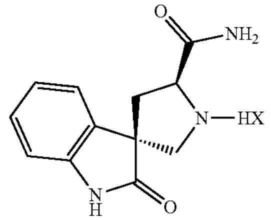

(F-2)

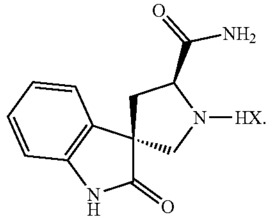

In certain embodiments of step (e), the compound of Formula (F-1) is produced in diastereomeric excess. In certain embodiments, the weight ratio of the compound of Formula (F-1) and the compound of Formula (F-2) produced is from about 55:45 to 95:5 and is preferably from about 6:1 to 8:1.

Suitable acids, such as but not limited to hydrogen chloride, hydrogen bromide, trifluoroacetic acid, or the like. A preferred acid is hydrogen chloride or hydrogen chloride generated in situ from the reaction of acetyl chloride and alkyl alcohol.

In preferred embodiments, step (e) occurs in a solvent. Suitable solvents include, but are not limited to, dichloromethane, chloroform, dioxane, ethyl acetate, heptane, hexane, methyl t-butyl ether, acetonitrile, acetone, N,N-dimethylformamide, tetrahydrofuran, and toluene, and mixtures of two or more thereof. Preferably the solvent is N,N-dimethylformamide or N,N-dimethylformamide with one or more co-solvents selected from toluene, acetonitrile, ethyl acetate and dichloromethane. In certain embodiments of step (e), the mixture of the compound of Formula (F-1) and the compound of Formula (F-2) is formed as a DMF solvate.

In one embodiment, the reaction is conducted at a temperature from about 0° C. to about 40° C., preferably from about 10° C. to about 30° C., and more preferably about 25° C. In one embodiment, step (e) takes place for a period from about 30 minutes to about 10 hours, preferably about 5 hours to about 3 days, and more preferably about 2 days.

In one embodiment, the compound of Formula (F-1) is separated from the compound of Formula (F-2) by recrystallizing the mixture of the compound of Formula (F-1) and the compound of Formula (F-2). The recrystallization is preferably conducted at a temperature from about 20° C. to about 100° C., more preferably from about 50° C. to about 85° C., and most preferably about 55° C. A preferred solvent for recrystallization is N,N-dimethylformamide (DMF).

In a preferred embodiment, the process of the invention further comprises isolating the compound of Formula (F-1), preferably in a substantially pure form.

Step (f)

The compound of Formula (F-1) from step (e) is preferably reacted with the compound of Formula (K) in the presence of an amide coupling agent. Suitable amide coupling agents include, but are not limited to, acetic anhydride, pivaloyl chloride, ethyl chloroformate (ECF), isobutyl chloroformate (IBCF), Boc anhydride, or di-tert-butyl dicarbonate ($Boc_2O$), 2-ethoxy-1-ethoxycarbonyl-1,2-dihydroquinoline, methanesulfonyl chloride (MsCl), p-toluenesulfonyl chloride (TsCl), n-propanephosphonic acid anhydride (T3P), ethylmethylphosphinic anhydride (EMPA), 1,1'-carbonyldiimidazole (CDI), N,N'-dicyclohexylcarbodiimide (DCC), N,N'-diisopropylcarbodiimide (DIC), (1-ethyl-3-(3'-dimethylaminopropyl)-carbodiimide hydrochloride (EDC), 1-hydroxy-7-azabenzotriazole (HOAt), 1-hydroxybenzotriazole (HOBt), ((benzotriazol-1-yloxy)tris-(dimethylamino)phosphonium hexafluorophosphate (BOP), N-[(dimethylamino)-1H-1,2,3-triazolo[4,5-b]pyridin-1-ylmethylene]-N-methylmethanaminium hexafluorophosphate N-oxide (HATU), N-[(1Hbenzotriazol-1-yl)-(dimethylamino)methylene]-N-methylmethanaminiumtetrafluoroborate N-oxide (TBTU), 2-(2-oxo-1(2H)-pyridyl-1,1,3,3-tetramethyluronium tetrafluoroborate (TPTU), O-[(cyano(ethoxycarbonyl)methyleneamino]-N,N,N',N'-tetramethyluronium tetrafluoroborate (TOTU), N-[(1H-benzotriazol-1-yl) (dimethylamino)-methylene]-N-methylmethanaminium hexafluorophosphate N-oxide (HBTU), cyanuric chloride, 2-chloro-4,6-dimethoxy-1,3,5-triazine (CDMT), 4-(4,6-dimethoxy-1,3,5-triazin-2-yl)-4-methylmorpholinium chloride (DMTMM), or boric acid. Preferably the coupling agent is n-propanephosphonic acid anhydride (T3P).

In certain embodiments, step (f) occurs in the presence of a suitable base, such as but not limited to triethylamine, diisopropylethylamine, or N-methylmorpholine. A preferred base is N-methylmorpholine.

In certain embodiments, step (f) occurs in the presence of a coupling agent and a suitable base. Preferably the coupling agent is n-propanephosphonic acid anhydride (T3P) and the base is N-methylmorpholine.

In preferred embodiments, step (f) occurs in a solvent. Suitable solvents include, but are not limited to, methanol, ethanol, acetonitrile, dichloromethane, chloroform, dioxane, ethyl acetate, heptane, hexane, methyl t-butyl ether, tetrahydrofuran, N,N-dimethylformamide and toluene, or a mixture of two or more thereof. Preferably the solvent is N, N-dimethylformamide.

In certain embodiments, step (f) is carried out at a suitable temperature, such as for example from about −10° C. to about 30° C., preferably from about −10° C. to about 10° C., and more preferably about 0° C. In one embodiment, step (f) takes place for a period from about 1 hour to about 24 hours, preferably about 4 hours.

In preferred embodiments, the process of the invention further includes isolating the compound of Formula (L), preferably in substantially pure form.

Step (g)

The compound of Formula (L) is preferably converted to the compound of Formula (M) by reaction with a hydrogen source. In embodiments wherein $PG_1$ is Cbz, Fmoc, Moz, or Pnz, the hydrogen source can be hydrogen, ammonium formate, or the like. In certain embodiments, the reaction proceeds in the presence of a catalyst such as, but not limited to, palladium on carbon, palladium hydroxide on carbon, or Raney nickel. Preferably the hydrogen source is $H_2$, and the catalyst is palladium on carbon. In certain embodiments, the reaction is conducted under a suitable hydrogen pressure, such as, but not limited to, from about 0.5 atm to about 10 atm, preferably from about 1 atm to 5 atm.

In certain embodiments, the compound of Formula (L) is reacted with the hydrogen source in the presence of a suitable acid, such as, but not limited to, hydrogen chloride, hydrogen bromide, trifluoroacetic acid, methanesulfonic acid, trifluoromethanesulfonic acid, acetic acid, or a combination of two or more thereof, or the like to remove the $PG_1$ group, and to generate a salt form of the Compound of Formula (M). A preferred acid is hydrogen bromide in acetic acid.

In certain embodiments where $PG_1$ is Cbz, Fmoc, Moz, or Pnz, the hydrogen source is $H_2$, the catalyst is palladium on carbon and the reaction is conducted in the presence of a suitable acid, such as but not limited to p-toluenesulfonic acid or methanesulfonic acid to remove the $PG_1$ group and to generate a salt form of the compound of Formula (M).

In preferred embodiments, step (g) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, N, N-dimethylformamide, toluene, acetic acid and mixtures of two or more thereof. Preferred solvents include methanol, acetic acid, and N,N-dimethylformamide.

In certain embodiments, step (g) is carried out at a suitable temperature, such as, for example, from about −20° C. to about 50° C., preferably about 0° C. to about 30° C. In one embodiment, the reaction takes place over a period from about 1 hours to about 24 hours, preferably from about 1 hour to about 8 hours.

In certain embodiments, the compound of Formula (M) or salt form thereof is directly used for next step without further separation.

In preferred embodiments, the process of the invention further comprises isolating the compound of Formula (M) or salt form thereof, preferably in substantially pure form.

Step (h)

The compound of Formula (M) or salt thereof is preferably reacted with the compound of Formula (J) or salt thereof in the presence of an amide coupling agent. Suitable amide coupling agents include, but are not limited to, acetic anhydride, pivaloyl chloride, ethyl chloroformate (ECF), isobutyl chloroformate (IBCF), Boc anhydride, or di-tert-butyl dicarbonate ($Boc_2O$), 2-ethoxy-1-ethoxycarbonyl-1,2-dihydroquinoline, methanesulfonyl chloride (MsCl), p-toluenesulfonyl chloride (TsCl), n-propanephosphonic acid anhydride (T3P), ethylmethylphosphinic anhydride (EMPA), 1,1'-carbonyldiimidazole (CDI), N,N'-dicyclohexylcarbodiimide (DCC), N,N'-diisopropylcarbodiimide (DIC), (1-ethyl-3-(3'-dimethylaminopropyl)-carbodiimide hydrochloride (EDC), 1-hydroxy-7-azabenzotriazole (HOAt), 1-hydroxybenzotriazole (HOBt), ((benzotriazol-1-yloxy)tris-(dimethylamino)phosphonium hexafluorophosphate (BOP), N-[(dimethylamino)-1H-1,2,3-triazolo[4,5-b]pyridin-1-ylmethylene]-N-methylmethanaminium hexafluorophosphate N-oxide (HATU), N-[(1Hbenzotriazol-1-yl)-(dimethylamino)methylene]-N-methylmethanaminiumtetrafluoroborate N-oxide (TBTU), 2-(2-oxo-1(2H)-pyridyl-1,1,3,3-tetramethyluronium tetrafluoroborate (TPTU), O-[(cyano(ethoxycarbonyl)methyleneamino]-N,N,N',N'-tetramethyluronium tetrafluoroborate (TOTU), N-[(1H-benzotriazol-1-yl) (dimethylamino)-methylene]-N-methylmethanaminium hexafluorophosphate N-oxide (HBTU), cyanuric chloride, 2-chloro-4,6-dimethoxy-1,3,5-triazine (CDMT), 4-(4,6-dimethoxy-1,3,5-triazin-2-yl)-4-methylmorpholinium chloride (DMTMM), and boric acid. Preferably the coupling agent is N-[(dimethylamino)-1H-1,2,3-triazolo[4,5-b]pyridin-1-ylmethylene]-N-methylmethanaminium hexafluorophosphate N-oxide (HATU).

Preferred salts of the compound of Formula (J) include the potassium and sodium salts. Preferred salts of the compound of Formula (M) include the acetate, chloride and bromide salts.

In certain embodiments, step (h) occurs in the presence of a suitable base, such as, but not limited to, triethylamine, diisopropylethylamine, or N-methylmorpholine. A preferred base is N-methylmorpholine.

In certain embodiments, step (h) occurs in the presence of an amide coupling agent and a suitable base where the amide coupling agent is HATU and the base is N-methylmorpholine.

In preferred embodiments, step (h) occurs in a solvent such as, but are not limited to acetonitrile, acetone, chloroform, dichloromethane, N,N-dimethylformamide, dimethyl sulfoxide, dioxane, ethyl acetate, heptane, hexane, methanol, methyl t-butyl ether, tetrachloromethane, tetrahydrofuran, toluene, or a mixture of two or more thereof. Preferably the solvent is N,N-dimethylformamide.

Step (h) is conducted at a suitable temperature, for example from about 0° C. to about 50° C., preferably from about 20° C. to about 30° C., and more preferably about 25° C. In one embodiment, step (h) takes place for a period from about 1 hour to about 24 hours, preferably from about 3 hours to about 12 hours.

In a preferred embodiment, the process of the invention further comprises isolating Compound of Formula (N), preferably in a substantially pure form.

Step (i)

The compound of Formula (N) is converted to the compound of Formula (A) by reaction with a dehydration reagent. Suitable dehydration reagents include but are not limited to, n-propylphosphonic anhydride (T3P), trifluoroacetic anhydride (TFAA), methyl N-(triethylammonium-sulfonyl)carbamate (Burgess reagent), phosphorus oxide ($P_2O_5$). A preferred dehydration reagent is trifluoroacetic anhydride (TFAA).

In certain embodiments, step (i) occurs in the presence of a suitable base, such as, but not limited to, triethylamine, diisopropylethylamine, N-methylmorpholine, 1,8-diazabicyclo(5.4.0)undec-7-ene (DBU), imidazole, pyridine, 2,6-lutidine, ethyl nicotinate, N-methylpiperazine, or 1-methylimidazole. A preferred base is triethylamine.

In certain embodiments, step (i) occurs in the presence of a dehydration reagent and a base where the dehydration reagent is trifluoroacetic anhydride (TFAA), and the base is triethylamine.

In preferred embodiments, step (i) occurs in a solvent. Suitable solvents include, but are not limited to, acetonitrile, acetone, dichloromethane, dichloroethane, N,N-dimethylformamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is ethyl acetate.

In certain embodiments, step (i) is carried out at a suitable temperature, such as for example from about −10° C. to about 10° C., preferably from about −5° C. to about 5° C., and more preferably about 0° C. In one embodiment, step (i) takes place for a period from about 30 minutes to about 2 hours, preferably about 1 hour.

In preferred embodiments, the process of the invention further includes isolating the compound of Formula (A), preferably in substantially pure form.

In certain embodiments, the invention provides a method of producing the Compound of Formula (A) comprising steps (f), (g), (h), and (i) described above.

In certain embodiments, the invention provides a method of producing the Compound of Formula (A) comprising steps (h) and (i) described above.

In one embodiment, the present invention provides a process for preparing a compound of Formula (J) or salt thereof (J)

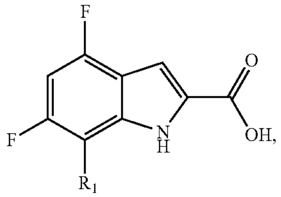

comprising the steps of:

(J-1) reducing a compound of Formula (G-a) to produce a compound of Formula (G-b):

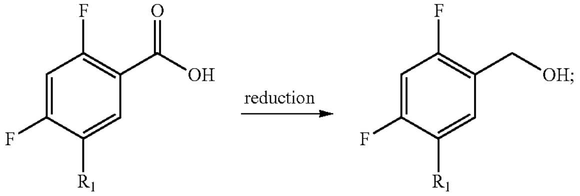

(G-a) (G-b)

(J-2) oxidizing the compound of Formula (G-b) to produce a compound of Formula (G):

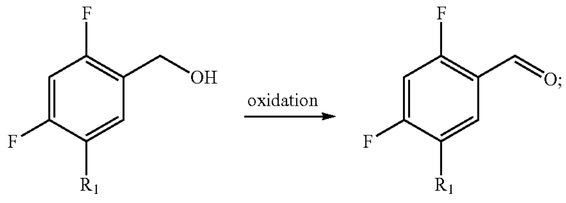

(G-b) (G)

(J-3) reacting the compound of Formula (G) with a compound of Formula (G-1), in the presence of a base to produce a Compound of Formula (H):

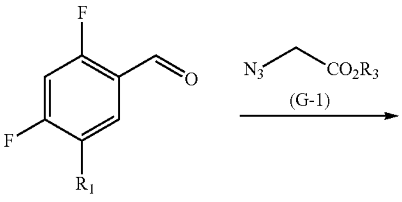

(G)

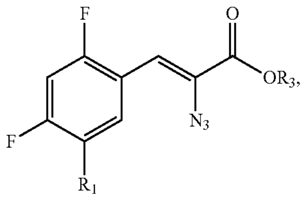

(H)

wherein $R_3$ is methyl, ethyl, or benzyl;

(J-4) converting the compound of Formula (H) to a compound of Formula (I) via Hemetsberger indole cyclization:

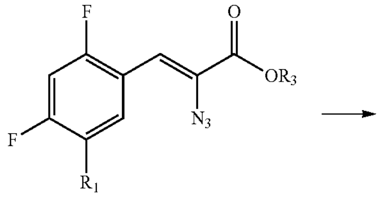

(H)

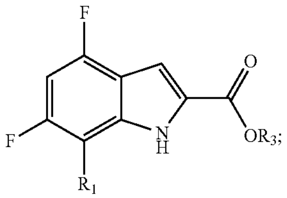

(I)

and (J-5) reacting the compound of Formula (I) with a base to yield the Compound of Formula (J), or salt thereof:

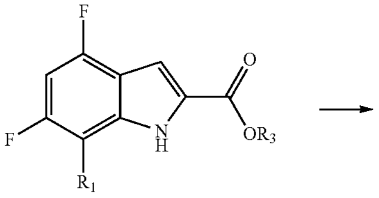

(I)

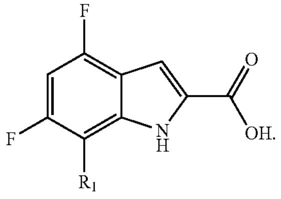

(J)

In another embodiment, the present invention provides a process for preparing a compound of Formula (J) or salt thereof:

(J)

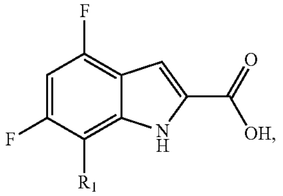

comprising the steps of:

(J-1) reducing a compound of Formula (G-a) to produce a compound of Formula (G-b):

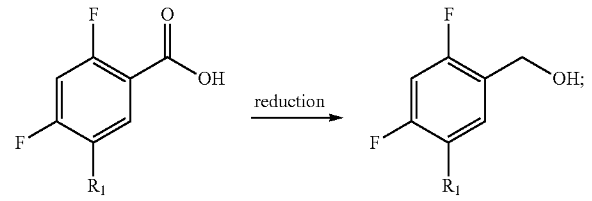

(G-a) (G-b)

(J-2) oxidizing the compound of Formula (G-b) to produce a compound of Formula (G):

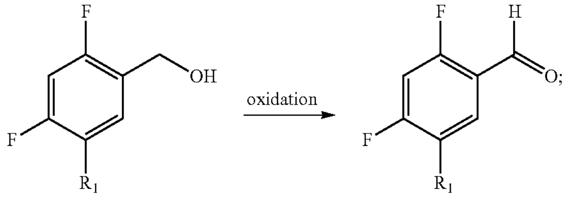

(G-b) (G)

(J-2a) reacting the compound of Formula (G) with sodium bisulfite to produce a compound of Formula (G-c):

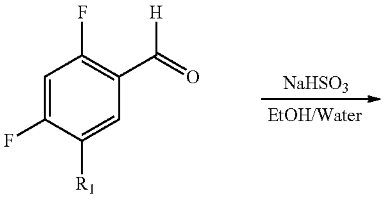

(G)

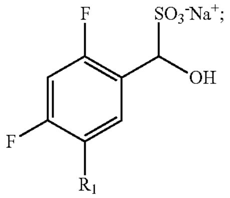

(G-c)

(J-2b) reacting the compound of Formula (G-c) with a base to produce a compound of Formula (G):

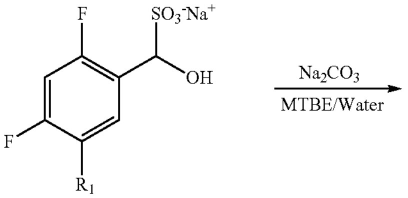

(G-c)

-continued

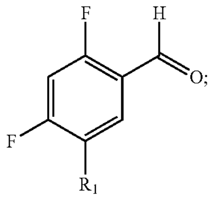

(G)

(J-3) reacting the compound of Formula (G) with a compound of Formula (G-1), in the presence of a base to produce a Compound of Formula (H):

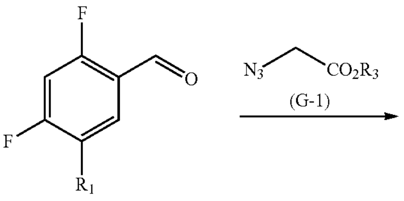

(G)

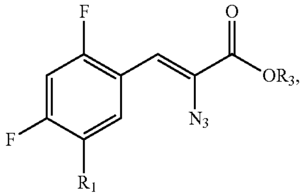

(H)

wherein $R_3$ is methyl, ethyl, or benzyl;

(J-4) converting the compound of Formula (H) to a compound of Formula (I) via Hemetsberger indole cyclization:

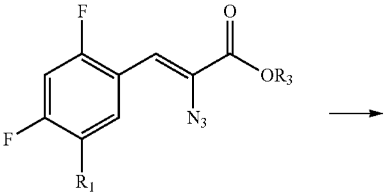

(H)

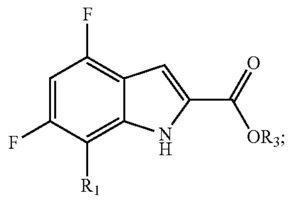

(I)

and (J-5) reacting the compound of Formula (I) with a base to yield the Compound of Formula (J), or salt thereof:

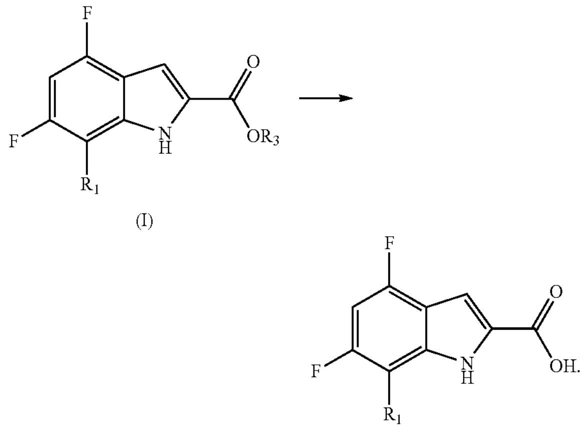

(I)

(J)

Step (J-1)

The compound of Formula (G-a) is preferably reduced by reaction with a reducing agent. Suitable reducing agents include, but are not limited to, lithium aluminum hydride, lithium borohydride, sodium borohydride, diisobutylaluminum hydride, borane-tetrahydrofuran complex, borane-dimethyl sulfide complex, and the like. Preferably the reducing agent is sodium borohydride or borane-tetrahydrofuran complex.

In preferred embodiments, step (J-1) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and mixtures of two or more thereof. A preferred solvent is tetrahydrofuran.

In one embodiment, the reaction in step (J-1) is conducted at a suitable temperature, for example, from about −20° C. to about 50° C., preferably from about −5° C. to about 25° C. In one embodiment, the reaction takes place over a period from about 0.5 hours to about 12 hours, preferably about 2 to 6 hours.

In certain embodiments, the process of the invention further comprises isolating the compound of Formula (G-b), preferably in substantially pure form.

Step (J-2)

The compound of Formula (G-b) is oxidized by reaction with an oxidizing agent. Suitable oxidizing agents include, but are not limited to, trichloroisocyanuric acid with TEMPO, sodium hypochlorite (NaClO), sodium hypochlorite with TEMPO, oxalyl chloride with dimethyl sulfoxide, manganese oxide, chromium trioxide, pyridinium chlorochromate (PCC), sodium perchloride, Dess-Martin periodinane (DMP), and the like. A preferred oxidizing agent is sodium hypochlorite with TEMPO.

In preferred embodiments, the reaction in step (J-2) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and mixtures of two or more thereof. A preferred solvent is methyl tert-butyl ether (MTBE).

The reaction in step (J-2) is conducted at a suitable temperature, for example from about −20° C. to about 50° C., preferably from about −10° C. to about 10° C., and more preferably about from about −5° C. to about 5° C. In certain embodiments, the reaction in step (J-2) takes place for a period from about 10 minutes to about 10 hours, preferably about 30 minutes to about 3 hours.

Step (J-2a)

In one embodiment, the reaction in step (J-2a) occurs in a solvent. Suitable solvents include, but are not limited to, acetonitrile, dioxane, ethyl acetate, methyl tert-butyl ether, tetrahydrofuran, toluene, MeOH, EtOH, water, and mixtures of two or more thereof. A preferred solvent is a mixture of MTBE, EtOH, and water.

In one embodiment, the reaction in step (J-2a) is conducted at a suitable temperature, for example, from about 0° C. to about 60° C., preferably from about 20° C. to about 40° C. In one embodiment, the reaction takes place over a period from about 0.5 hours to about 12 hours, preferably about 2 to 6 hours.

Step (J-2b)

Step (J-2b) occurs in the presence of a suitable base, such as, but not limited to, sodium carbonate, potassium carbonate, cesium carbonate, sodium hydroxide, sodium methoxide, sodium ethoxide, sodium tert-butoxide, lithium diisopropyl amide, lithium 2,2,6,6-tetramethylpiperidide, sodium diisopropyl amide, lithium bis(trimethylsilyl)amide, sodium bis(trimethylsilyl)amide, triethylamine, diisopropylethylamine, or the like. Preferably, the base is sodium carbonate.

In one embodiment, the reaction in step (J-2b) occurs in a solvent. Suitable solvents include, but are not limited to, acetonitrile, acetone, dimethyl sulfoxide, dioxane, ethyl acetate, methyl tert-butyl ether, tetrahydrofuran, toluene, EtOH, water, and mixtures of two or more thereof. A preferred solvent is methyl tert-butyl ether (MTBE) or a mixture of MTBE and water.

In one embodiment, the reaction in step (J-2b) is conducted at a suitable temperature, for example, from about 0° C. to about 40° C., preferably from about 20° C. to about 25° C. In one embodiment, the reaction takes place over a period from about 0.5 hours to about 12 hours, preferably about 2 to 6 hours.

In certain embodiments, the process of the invention further comprises isolating the compound of Formula (G), preferably in substantially pure form.

Step (J-3)

Step (J-3) occurs in the presence of a suitable base, such as, but not limited to, sodium methoxide, sodium ethoxide, sodium tert-butoxide, lithium diisopropyl amide, lithium 2,2,6,6-tetramethylpiperidide, sodium diisopropyl amide, lithium bis(trimethylsilyl)amide, sodium bis(trimethylsilyl)amide, or the like. Preferably, the base is sodium methoxide or sodium ethoxide.

In preferred embodiments, step (J-3) occurs in presence of a sacrificial electrophile, such as, but not limited to, $CF_3CO_2Et$, ethyl trichloroacetate or ethyl formate, to prevent hydrolysis in the base-catalyzed condensation reaction and thereby improve the yield. A preferred sacrificial electrophile is $CF_3CO_2Et$.

In preferred embodiments, step (J-3) occurs in a in a suitable solvent, such as, but not limited to, dichloromethane, chloroform, dioxane, ethyl acetate, heptane, hexane, methyl t-butyl ether, tetrahydrofuran, methanol, ethanol, or toluene, and mixtures of two or more thereof. Preferably, the solvent is methanol or ethanol. More preferably, the solvent is methanol.

In preferred embodiments, step (J-3) occurs in presence of sodium methoxide or sodium ethoxide as a base; methanol or ethanol as a solvent and $CF_3CO_2Et$ as a sacrificial electrophile.

The reaction of step (J-3) is conducted at a suitable temperature, for example from about −10° C. to about 10°

C., preferably from about −5° C. to about 10° C., and more preferably about 0° C. In one embodiment, step (J-3) takes place for a period from about 30 minutes to about 10 hours, preferably about 5 hours to about 24 hours, and more preferably about 8 hours to about 14 hours.

In certain embodiments, the process of the invention further comprises isolating the compound of Formula (H), preferably in substantially pure form.

Step (J-4)

In step (J-4) the compound of Formula (H) is heated to generate the active intermediate, which can cyclize to form the compound of Formula (I).

In preferred embodiments, step (J-4) occurs in a solvent. Suitable solvents include, but are not limited to, trimethylbenzene, dichloromethane, chloroform, dioxane, ethyl acetate, heptane, hexane, methyl t-butyl ether, tetrahydrofuran, methanol, xylene, and toluene, and mixtures of two or more thereof. Preferably the solvent is a mixture of xylene and methanol. Preferably the volume ratio of xylene to methanol is greater than 1. More preferably the volume ratio of xylene to methanol is 5:1.

In certain embodiments, in step (J-4), the compound of Formula (I) is prepared via a continuous flow chemistry technology by conducting the reaction in a flow reactor with adjustable flow rate, reaction retention time, reaction temperature and pressure. Step (J-4) is carried out at a suitable temperature, such as for example from about 100° C. to about 300° C., preferably from about 150° C. to about 250° C., and more preferably about 200° C. In one embodiment, step (J-4) takes place with residence time in about 10 minutes to about 6 hours, preferably in about 25 minutes.

In preferred embodiments, the process of the invention further includes isolating the compound of Formula (I), preferably in substantially pure form.

Step (J-5)

Step (J-5) is the saponification of the ester of the compound of Formula (I) in the presence of a suitable base followed by treatment with an acid to form the compound of Formula (J). Suitable bases include, but are not limited to, sodium hydroxide, potassium hydroxide, lithium hydroxide, or combinations of two or more thereof. A preferred base is sodium hydroxide. Suitable acids include, but are not limited to, hydrogen chloride, hydrogen bromide, sulfuric acid and combinations of two or more thereof. A preferred acid is hydrogen chloride.

In preferred embodiments, step (J-5) occurs in a solvent. Suitable solvents include, but are not limited to, dichloromethane, chloroform, dioxane, ethyl acetate, heptane, hexane, methyl t-butyl ether, tetrahydrofuran, water, toluene, and mixtures of two or more thereof. Preferably the solvent is mixture of tetrahydrofuran and water or MTBE and water.

In certain embodiments, step (J-5) is carried out at a suitable temperature, such as for example from about 30° C. to about 100° C., preferably from about 55° C. to about 65° C., and more preferably about 65° C. In one embodiment, step (J-5) takes place for a period from about 1 hour to about 3 days, preferably from about 10 hours to about 2 days, and more preferably about 24 hours.

In preferred embodiments, the process of the invention further includes isolating the compound of Formula (J), preferably in substantially pure form.

In certain embodiments, the invention provides a method of producing the Compound of Formula (A) comprising steps (a), (b), (c), (d), (e), (f), (g), (J-1), (J-2), (J-3), (J-4), (J-5), (h), and (i) described above.

In certain embodiments, the invention provides a method of producing the Compound of Formula (A) comprising steps (a), (b), (c), (d), (e), (f), (g), (J-1), (J-2), (J-2a), (J-2b), (J-3), (J-4), (J-5), (h), and (i) described above.

In certain embodiments, the invention provides a method of producing the Compound of Formula (A) comprising steps (a), (b), (c), (d), (e), (f), (g), (J-3), (J-4), (J-5), (h), and (i) described above.

In one embodiment, the present invention provides a process for preparing Compound (I).

(I)

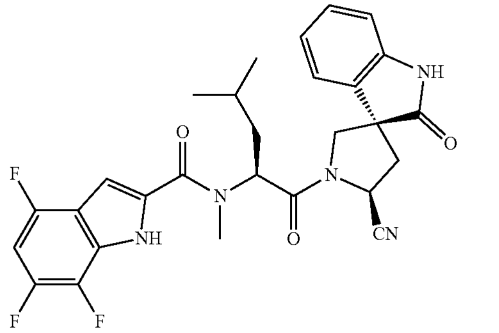

the process comprises the steps of:

(1) reacting Compound (w) with formaldehyde to produce Compound (b):

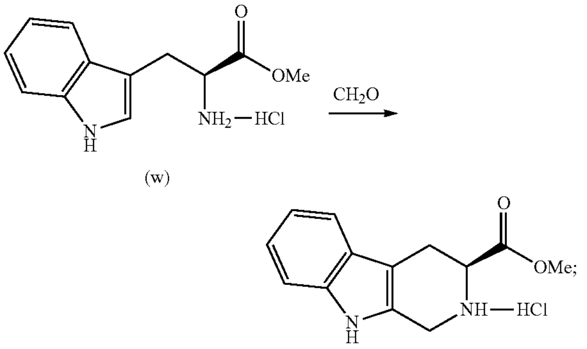

(w)

(b)

(2) converting Compound (b) to Compound (c):

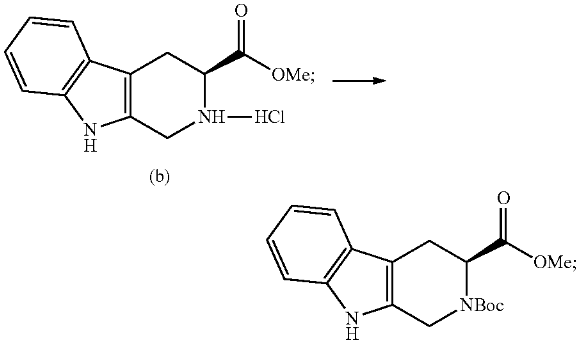

(b)

(c)

(3) converting Compound (c) to mixture of Compound (d-1) and Compound (d-2) via a rearrangement reaction:

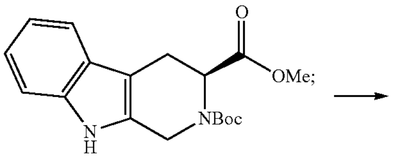

(c)

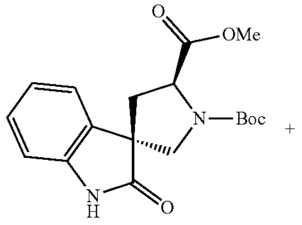

(d-1)-major

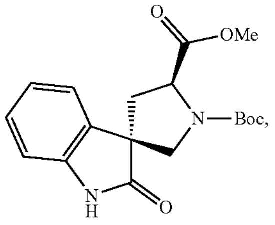

(d-2)-minor wherein one of the two diastereomers (d-1) and (d-2) is in diastereomeric excess, for example, a diastereomers excess of at least 5, 10, 20, 30, 40, 50, 60, 70, 80, 90, or 95%;

(4) converting the mixture of Compound (d-1) and Compound (d-2) to a mixture of Compound (e-1) and Compound (e-2):

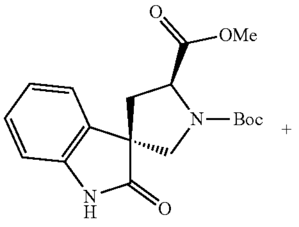

(d-1)-major

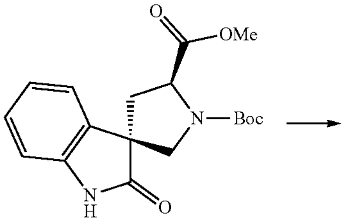

(d-2)-minor

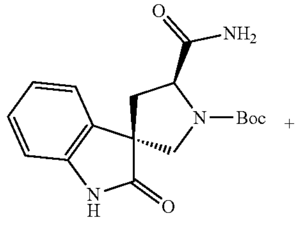

(e-1)-major

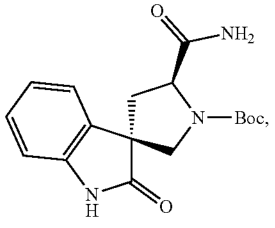

(e-2)-minor wherein one of Compound (e-1) and Compound (e-2) is produced in diastereomeric excess, for example, a diastereomers excess of at least 5, 10, 20, 30, 40, 50, 60, 70, 80, 90 or 95%;

(5) converting the mixture of Compound (e-1) and Compound (e-2) to the hydrochloride salt of Compound (f-1) and the hydrochloride salt of Compound (f-2) as a mixture of diastereomers:

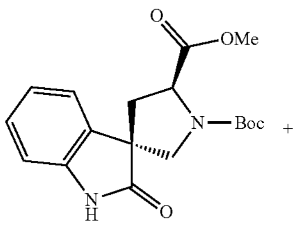

(e-1)-major

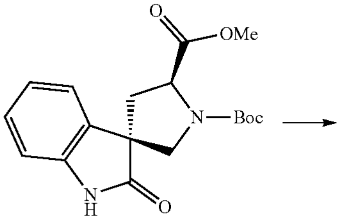

(e-2)-minor

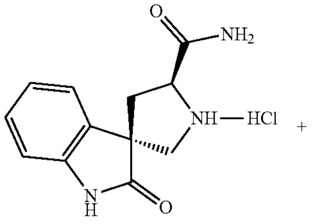

(f-1)-major

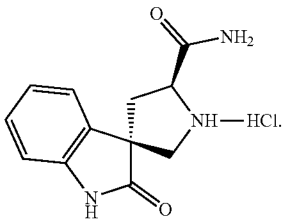

(f-2)-minor wherein one of Compound (f-1) and Compound (f-2) is produced in diastereomeric excess, for example, a diastereomeric excess of at least 5, 10, 20, 30, 40, 50, 60, 70, 80, 90, or 95%;

(6) reacting Compound (f-1) with Compound (k)

(k)

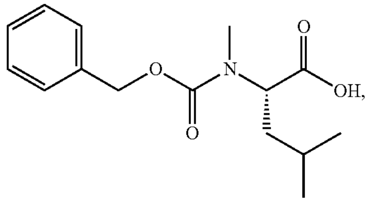

to produce Compound (l):
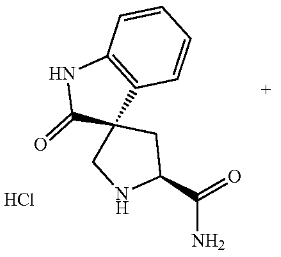
(f-1)
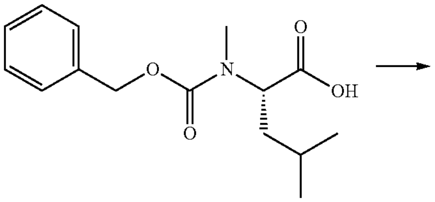
(k)
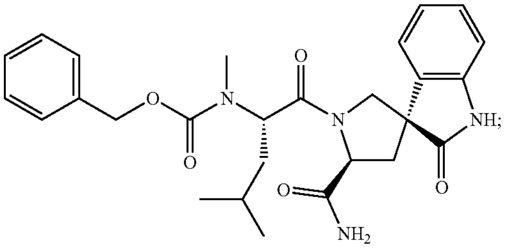
(l)
(7) converting Compound (l) to Compound (m):
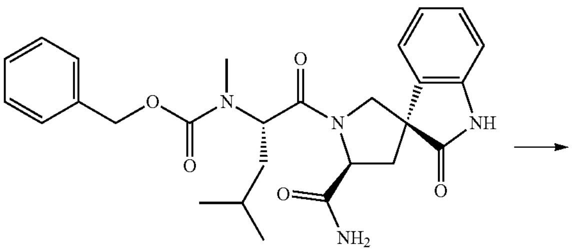
(l)
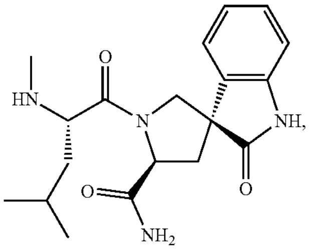
(m)
alternatively, with a suitable acid, converting Compound (l), to a salt form of Compound (m);
(8) Reacting Compound of Formula (m) or salt form of Compound of Formula (m) with indole acid Compound (j) or salt thereof,
(j)
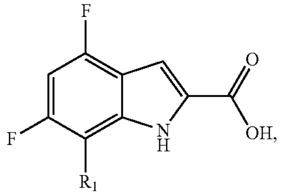
to provide Compound (n):
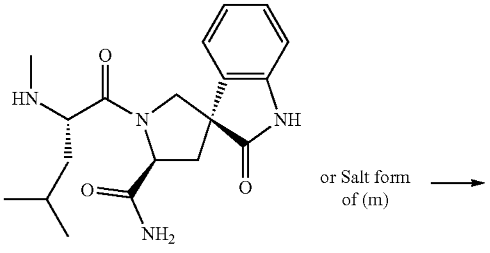
(m)
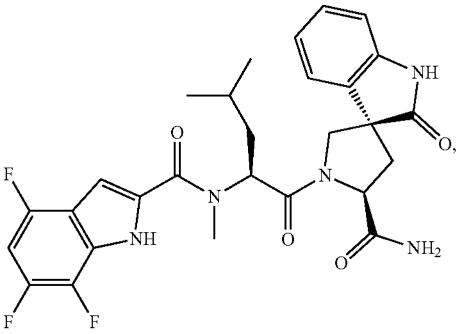
(n)
(9) converting Compound (n) to Compound (I):
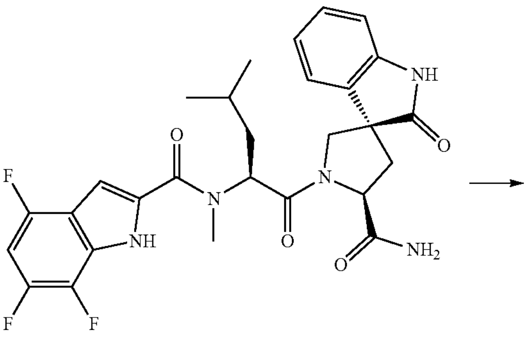
(n)

-continued

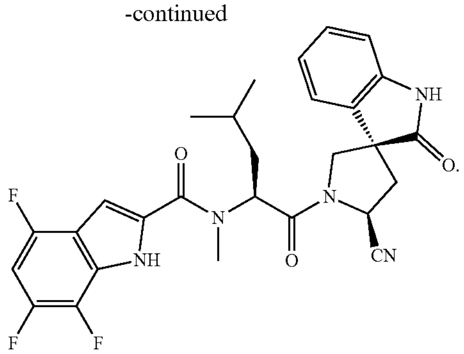

(I)

Step (1)

In preferred embodiments, step (1) occurs in a suitable solvent, such as, but not limited to, methanol, t-butyl alcohol, acetonitrile, acetone, dichloromethane, chloroform, dimethylformamide, dimethylsulfoxide, dioxane, ethyl acetate, heptane, hexane, methyl t-butyl ether, tetrahydrofuran, and toluene, or a mixture of two or more thereof. Preferably the solvent is methanol.

In one embodiment, the reaction is conducted at a temperature from about 0° C. to about 100° C., preferably from about 45° C. to about 85° C., and more preferably about 65° C. In one embodiment, step 1) takes place for a period from about half an hour to about 1 day, preferably about half an hour to about 5 hours, and more preferably about 1 hour.

In a preferred embodiment, the process of the invention further comprises isolating Compound (b), preferably in a substantially pure form.

Step (2)

In step (2), Compound (b) is reacted with a suitable Boc protection agent, such as, but not limited to, tert-butyl phenyl carbonate, di-tert-butyl dicarbonate, N-(tert-butoxycarbonyloxy)phthalimide or 1-tert-butoxycarbonyl-1,2,4-triazole. Preferably the Boc protection reagent is di-tert-butyl dicarbonate (Boc anhydride).

Step (2) preferably occurs in the presence of a suitable base, such as, but not limited to, triethylamine, diisopropylethylamine, sodium bicarbonate or N-methylmorpholine. A preferred base is triethylamine.

In preferred embodiments, step (2) occurs in a solvent. A suitable solvent is included, but not limited to 2-Me THF, t-butyl alcohol, acetonitrile, acetone, dichloromethane, chloroform, dimethyl formamide, dimethyl sulfoxide, dioxane, ethyl acetate, heptane, hexane, methyl t-butyl ether, tetrahydrofuran, water, and toluene, or a mixture of two or more thereof. Preferably the solvent is 2-Me THE and water as co-solvent. Preferably the volume ratio of 2-Me THE to water is 4:1.

In one embodiment, the reaction of step (2) is conducted at a temperature from about −10° C. to about 60° C., preferably from about 0° C. to about 40° C., and more preferably about 5° C. to about 25° C. In one embodiment, step (b) takes place for a period from about 1 hour to about 24 hours, preferably about 1 hour to about 10 hours, and more preferably about 5 hours.

In a preferred embodiment, the process of the invention further comprises isolating Compound (c), preferably in a substantially pure form.

Step (3)

In step (3), Compound (c) is reacted with an oxidizing agent to produce a mixture of Compound (d-1) and Compound (d-2). Preferably the reaction produces Compound (d-1) in diastereomeric excess. The weight ratio of Compound (d-1) and Compound (d-2) produced is preferably from about from 55:45 to 95:5, and more preferably is from about 6:1 to about 8:1.

Suitable oxidizing agents include, but are not limited to, N-bromosuccinimide (NBS), hydrogen peroxide, meta-chloroperoxybenzoic acid (m-CPBA), potassium peroxymonosulfate (Oxone), 1-chloromethyl-4-fluoro-1,4-diazoniabicyclo[2.2.2]octane bis(tetrafluoroborate) (Selecfluor), tert-butyl hypochlorite, N-iodosuccinimide (NIS), or the like. A preferred oxidizing agent is N-bromosuccinimide (NBS).

In certain embodiments, step (3) occurs in the presence of a suitable acid, such as, but not limited to, acetic acid, formic acid, trifluoroacetic acid, benzoic acid, hydrochloride acid, phosphonic acid, sulfuric acid, p-toluenesulfonic acid, or the like. A preferred acid is acetic acid.

In preferred embodiments of step (3), the oxidizing agent is N-bromosuccinimide (NBS) and the acid is acetic acid.

In preferred embodiments, step (3) occurs in a in a solvent. A suitable solvent is included, but not limited to dichloromethane, chloroform, dioxane, ethyl acetate, heptane, hexane, methyl t-butyl ether, tetrahydrofuran (THF), 2-Me THF, water and toluene, or a mixture of two or more thereof. Preferably the solvent is a mixture of 2-Me THF, THE and water. Preferably the volume ratio of 2-Me THF/TiF/water is around 3.5/1.5/1.

In one embodiment, the reaction is conducted at a temperature from about −40° C. to about 30° C., preferably from about −30° C. to about −10° C., and more preferably about −30° C. In one embodiment, step (c) takes place for a period from about 30 minutes to about 3 hours, preferably about 30 minutes to about 1 hours, and more preferably about 30 min.

In one embodiment, Compound (d-1) is the major product. In a preferred embodiment, the process of the invention further comprises isolating Compound (d-1) and Compound (d-2).

Step (4)

The mixture of Compound (d-1) and Compound (d-2) is preferably converted to the mixture of Compound (e-1) and Compound (e-2) by reaction with an ammonolysis reagent. In certain embodiments of step (4), Compound (e-1) is produced in diastereomeric excess. In certain embodiments, the weight ratio of Compound (e-1) and Compound (e-2) is from about 55:45 to 95:5, preferably from about 6:1 to 8:1.

Suitable ammonolysis reagents include, but are not limited to, ammonia, ammonium hydroxide, and the like. A preferred ammonolysis reagent is ammonia.

In preferred embodiments, step (4) occurs in a solvent. A suitable solvent is included, but not limited to dichloromethane, chloroform, dioxane, ethyl acetate, heptane, hexane, methyl t-butyl ether, tetrahydrofuran, methanol, ethanol, propanol and toluene, or a mixture of two or more thereof. Preferably the solvent is methanol.

In one embodiment, the reaction is conducted at a temperature from about 20° C. to about 60° C., preferably from about 40° C. to about 60° C., and more preferably about 45° C. In one embodiment, step (d) takes place for a period from about 2 days to about 7 days, preferably about 3 days to about 5 days, and more preferably about 5 days.

In one embodiment, Compound (e-1) is the major product. In a preferred embodiment, the process of the invention further comprises isolating Compound (e-1) and Compound (e-2).

Step (5)

The mixture of Compounds (e-1) and (e-2) is reacted with an acid to produce the mixture of Compounds (f-1) and (f-2). In certain embodiments of step (e), Compound (f-1) is produced in diastereomeric excess. In certain embodiments, the weight ratio of Compound (f-1) and Compound (f-2) produced is from about 55:45 to 95:5 and is preferably from about 6:1 to 8:1.

Suitable acids include, but are not limited to, hydrogen chloride, hydrogen bromide, trifluoroacetic acid, or the like. A preferred acid is hydrogen chloride or hydrogen chloride generated in situ from the reaction of acetyl chloride and alkyl alcohol.

In preferred embodiments, step (5) occurs in a solvent. Suitable solvents include, but are not limited to, dichloromethane, chloroform, dioxane, ethyl acetate, heptane, hexane, methyl t-butyl ether, acetonitrile, acetone, N,N-dimethylformamide, tetrahydrofuran, and toluene, and mixtures of two or more thereof. Preferably the solvent is N,N-dimethylformamide or N,N-dimethylformamide with one or more co-solvents selected from toluene, acetonitrile, ethyl acetate and dichloromethane. In certain embodiments of step (e), the mixture Compound (f-1) and Compound (f-2) is formed as a DMF solvate.

In one embodiment, the reaction is conducted at a temperature from about 0° C. to about 40° C., preferably from about 10° C. to about 30° C., and more preferably about 25° C. In one embodiment, step (e) takes place for a period from about 30 minutes to about 10 hours, preferably about 5 hours to about 3 days, and more preferably about 2 days.

In one embodiment, Compound (f-1) is separated from Compound (f-2) by recrystallizing the mixture of Compound (f-1) and Compound (f-2). The recrystallization is preferably conducted at a temperature from about 20° C. to about 100° C., more preferably from about 50° C. to about 85° C., and most preferably about 55° C. A preferred solvent for recrystallization is N,N-dimethylformamide (DMF).

In a preferred embodiment, the process of the invention further comprises isolating Compound (f-1), preferably in a substantially pure form.

Step (6)

Compound (f-1) is preferably reacted with Compound (k) in the presence of an amide coupling agent. Suitable amide coupling agents include, but are not limited to, acetic anhydride, pivaloyl chloride, ethyl chloroformate (ECF), isobutyl chloroformate (IBCF), Boc anhydride, or di-tert-butyl dicarbonate ($Boc_2O$), 2-ethoxy-1-ethoxycarbonyl-1,2-dihydroquinoline, methanesulfonyl chloride (MsCl), p-toluenesulfonyl chloride (TsCl), n-propanephosphonic acid anhydride (T3P), ethylmethylphosphinic anhydride (EMPA), 1,1'-carbonyldiimidazole (CDI), N,N'-dicyclohexylcarbodiimide (DCC), N,N'-diisopropylcarbodiimide (DIC), (1-ethyl-3-(3'-dimethylaminopropyl)-carbodiimide hydrochloride (EDC), 1-hydroxy-7-azabenzotriazole (HOAt), 1-hydroxybenzotriazole (HOBt), ((benzotriazol-1-yloxy)tris-(dimethylamino)phosphonium hexafluorophosphate (BOP), N-[(dimethylamino)-1H-1,2,3-triazolo[4,5-b]pyridin-1-ylmethylene]-N-methylmethanaminium hexafluorophosphate N-oxide (HATU), N-[(1Hbenzotriazol-1-yl)-(dimethylamino)methylene]-N-methylmethanaminiumtetrafluoroborate N-oxide (TBTU), 2-(2-oxo-1(2H)-pyridyl-1,1,3,3-tetramethyluronium tetrafluoroborate (TPTU), O-[(cyano(ethoxycarbonyl)methyleneamino]-N,N,N',N'-tetramethyluronium tetrafluoroborate (TOTU), N-[(1H-benzotriazol-1-yl) (dimethylamino)-methylene]-N-methylmethanaminium hexafluorophosphate N-oxide (HBTU), cyanuric chloride, 2-chloro-4,6-dimethoxy-1,3,5-triazine (CDMT), 4-(4,6-dimethoxy-1,3,5-triazin-2-yl)-4-methylmorpholinium chloride (DMTMM), or boric acid. Preferably the coupling agent is n-propanephosphonic acid anhydride (T3P).

In certain embodiments, step (6) occurs in the presence of a suitable base, such as but not limited to triethylamine, diisopropylethylamine, or N-methylmorpholine. A preferred base is N-methylmorpholine.

In certain embodiments, step (6) occurs in the presence of a coupling agent and a suitable base. Preferably the coupling agent is n-propanephosphonic acid anhydride (T3P) and the base is N-methylmorpholine.

In preferred embodiments, step (6) occurs in a solvent. Suitable solvents include, but are not limited to, methanol, ethanol, acetonitrile, dichloromethane, chloroform, dioxane, ethyl acetate, heptane, hexane, methyl t-butyl ether, tetrahydrofuran, N,N-dimethylformamide and toluene, or a mixture of two or more thereof. Preferably the solvent is N, N-dimethylformamide.

In certain embodiments, step (6) is carried out at a suitable temperature, such as for example from about −10° C. to about 30° C., preferably from about −10° C. to about 10° C., and more preferably about 0° C. In one embodiment, step (6) takes place for a period from about 1 hour to about 24 hours, preferably about 4 hours.

In preferred embodiments, the process of the invention further includes isolating Compound (l), preferably in substantially pure form.

Step (7)

Compound (l) is preferably converted to Compound (m) by reaction with a hydrogen source, such as hydrogen, ammonium formate, or the like, a catalyst such as, but not limited to, palladium on carbon, palladium hydroxide on carbon, or Raney nickel, optionally in the presence of a suitable acid, such as, but not limited to, hydrogen chloride, hydrogen bromide, trifluoroacetic acid, methanesulfonic acid, trifluoromethanesulfonic acid, acetic acid, or the like. Preferably the hydrogen source is $H_2$, and the catalyst is palladium on carbon. More preferably the hydrogen source is $H_2$, the catalyst is palladium on carbon and the reaction is conducted in the presence of p-toluenesulfonic acid to remove the Cbz group and to form the p-toluenesulfonic acid of Compound (m).

In certain embodiments, the reaction is conducted under a suitable hydrogen pressure, such as, but not limited to, from about 0.5 atm to about 10 atm, preferably from about 1 atm to 5 atm.

In preferred embodiments, step (7) occurs in a solvent. Suitable solvents include, but are not limited to, acetonitrile, acetone, dichloromethane, dimethyl formamide, dimethyl sulfoxide, dioxane, ethyl acetate, heptane, hexane, methanol, methyl t-butyl ether, ethanol, tetrahydrofuran, N, N-dimethylformamide, toluene, acetic acid and mixtures of two or more thereof. Preferred solvents include methanol, acetic acid, and N,N-dimethylformamide.

In certain embodiments, step (7) is carried out at a suitable temperature, such as, for example, from about −20° C. to about 50° C., preferably about 0° C. to about 30° C. In one embodiment, the reaction takes place over a period from about 1 hours to about 24 hours, preferably from about 1 hour to about 8 hours.

In certain embodiments, Compound (m) or the salt form thereof is directly used for next step without further separation.

In preferred embodiments, the process of the invention further comprises isolating Compound (m) or salt form thereof, preferably in substantially pure form.

Step (8)

Compound (m) or the salt thereof is preferably reacted with Compound (j) in the presence of an amide coupling agent. Suitable amide coupling agents include, but are not limited to, acetic anhydride, pivaloyl chloride, ethyl chloroformate (ECF), isobutyl chloroformate (IBCF), Boc anhydride, or di-tert-butyl dicarbonate ($Boc_2O$), 2-ethoxy-1-ethoxycarbonyl-1,2-dihydroquinoline, methanesulfonyl chloride (MsCl), p-toluenesulfonyl chloride (TsCl), n-propanephosphonic acid anhydride (T3P), ethylmethylphosphinic anhydride (EMPA), 1,1'-carbonyldiimidazole (CDI), N,N'-dicyclohexylcarbodiimide (DCC), N,N'-diisopropylcarbodiimide (DIC), (1-ethyl-3-(3'-dimethylaminopropyl)-carbodiimide hydrochloride (EDC), 1-hydroxy-7-azabenzotriazole (HOAt), 1-hydroxybenzotriazole (HOBt), ((benzotriazol-1-yloxy)tris-(dimethylamino)phosphonium hexafluorophosphate (BOP), N-[(dimethylamino)-1H-1,2,3-triazolo[4,5-b]pyridin-1-ylmethylene]-N-methylmethanaminium hexafluorophosphate N-oxide (HATU), N-[(1Hbenzotriazol-1-yl)-(dimethylamino)methylene]-N-methylmethanaminiumtetrafluoroborate N-oxide (TBTU), 2-(2-oxo-1(2H)-pyridyl-1,1,3,3-tetramethyluronium tetrafluoroborate (TPTU), O-[(cyano(ethoxycarbonyl)methyleneamino]-N,N,N',N'-tetramethyluronium tetrafluoroborate (TOTU), N-[(1H-benzotriazol-1-yl) (dimethylamino)-methylene]-N-methylmethanaminium hexafluorophosphate N-oxide (HBTU), cyanuric chloride, 2-chloro-4,6-dimethoxy-1,3,5-triazine (CDMT), 4-(4,6-dimethoxy-1,3,5-triazin-2-yl)-4-methylmorpholinium chloride (DMTMM), and boric acid. Preferably the coupling agent is N-[(dimethylamino)-1H-1,2,3-triazolo[4,5-b]pyridin-1-ylmethylene]-N-methylmethanaminium hexafluorophosphate N-oxide (HATU).

In certain embodiments, step (8) occurs in the presence of a suitable base, such as, but not limited to, triethylamine, diisopropylethylamine, or N-methylmorpholine. A preferred base is N-methylmorpholine.

In certain embodiments, step (8) occurs in the presence of an amide coupling agent and a suitable base where the amide coupling agent is HATU and the base is N-methylmorpholine.

Preferred salts of the compound of Formula (j) include the potassium and sodium salts. Preferred salts of the compound of Formula (m) include the acetate, chloride and bromide salts.

In preferred embodiments, step (8) occurs in a solvent such as, but are not limited to acetonitrile, acetone, chloroform, dichloromethane, N,N-dimethylformamide, dimethyl sulfoxide, dioxane, ethyl acetate, heptane, hexane, methanol, methyl t-butyl ether, tetrachloromethane, tetrahydrofuran, toluene, or a mixture of two or more thereof. Preferably the solvent is N,N-dimethylformamide.

Step (8) is conducted at a suitable temperature, for example from about 0° C. to about 50° C., preferably from about 20° C. to about 30° C., and more preferably about 25° C. In one embodiment, step (8) takes place for a period from about 1 hour to about 24 hours, preferably from about 3 hours to about 12 hours.

In a preferred embodiment, the process of the invention further comprises isolating Compound (n), preferably in a substantially pure form.

Step (9)

Compound (n) is converted to Compound (I) by reaction with a dehydration reagent. Suitable dehydration reagents include but are not limited to, n-propylphosphonic anhydride (T3P), trifluoroacetic anhydride (TFAA), methyl N-(triethylammoniumsulfonyl)carbamate (Burgess reagent), phosphorus oxide ($P_2O_5$). A preferred dehydration reagent is trifluoroacetic anhydride (TFAA).

In certain embodiments, step (9) occurs in the presence of a suitable base, such as, but not limited to, triethylamine, diisopropylethylamine, N-methylmorpholine, 1,8-diazabicyclo(5.4.0)undec-7-ene (DBU), imidazole, pyridine, 2,6-lutidine, ethyl nicotinate, N-methylpiperazine, or 1-methylimidazole. A preferred base is triethylamine.

In certain embodiments, step (9) occurs in the presence of a dehydration reagent and a base where the dehydration reagent is trifluoroacetic anhydride (TFAA), and the base is triethylamine.

In preferred embodiments, step (9) occurs in a solvent. Suitable solvents include, but are not limited to, acetonitrile, acetone, dichloromethane, dichloroethane, N,N-dimethylformamide, dimethyl sulfoxide, N-methyl-2-pyrrolidone, dioxane, ethyl acetate, heptane, hexane, methyl t-butyl ether, tetrahydrofuran, toluene, and mixtures of two or more thereof. A preferred solvent is ethyl acetate.

In certain embodiments, step (9) is carried out at a suitable temperature, such as for example from about −10° C. to about 10° C., preferably from about −5° C. to about 5° C., and more preferably about 0° C. In one embodiment, step (9) takes place for a period from about 30 minutes to about 2 hours, preferably about 1 hour.

In preferred embodiments, the process of the invention further includes isolating Compound (I), preferably in substantially pure form.

In certain embodiments, the invention further provides a method of purifying Compound (I) by crystallization. The method includes dissolving Compound (I) in a suitable solvent at a temperature from about 20° C. to about 80° C., preferably from about 45° C. to about 55° C., and more preferably about 50° C. The resulting solution is then cooled, for example, to a temperature of about 10-25° C., thereby inducing crystallization of Compound (I). Suitable solvent for crystallization include anisole, toluene, xylene, and mixtures of two or more thereof. Preferably the solvent is toluene. Compound (I) is preferably isolated as the corresponding toluene solvate.

The invention further provides a method of producing an amorphous form of Compound (I). The method comprises (ia) adding a first solvent to a toluene solvate of Compound (I) to produce a solution; (ib) removing a portion of the first solvent and toluene from the solution, for example by distillation; (ic) repeating steps (ia) and (ib) until a solution of Compound (I) is produced with a toluene concentration no greater than a predetermined value, such as 0.1% (wt/wt). The resulting solution is then mixed with a second solvent which is a nonsolvent for compound (I) to produce the amorphous form of Compound (I). Suitable first solvent/second solvent pairs include EtOH/water, isopropanol/water, acetone/water, and MTBE/n-heptane, Preferably the first solvent is ethanol and the second solvent is water.

The method of crystalizing Compound (I) and, optionally, the method of producing an amorphous form of Compound (I), can be performed on Compound (I) as produced by a method described herein.

In certain embodiments, the invention provides a method of producing Compound (I) comprising steps (6), (7), (8), and (9) described above.

In certain embodiments, the invention provides a method of producing Compound (I) comprising steps (8) and (9) described above.

In one embodiment, the present invention provides a process for preparing Compound (j), or salt thereof (j)

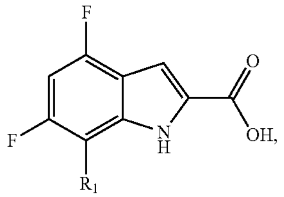

the process comprises the steps of:

(j-1) reducing Compound (g-a) to produce Compound (g-b):

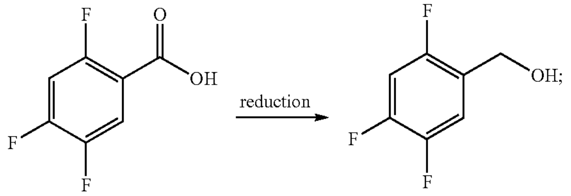

(g-a) (g-b)

(j-2) oxidizing Compound (g-b) to produce Compound (g):

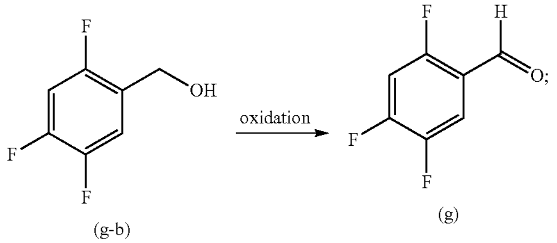 [SMILES: OCc1cc(F)c(F)cc1F ; O=Cc1cc(F)c(F)cc1F]

(g-b) (g)

(j-3) reacting Compound (g) with ethyl 2-azidoacetate in the presence of sodium methoxide as a base to produce a mixture of Compound (h-1) and Compound (h-2):

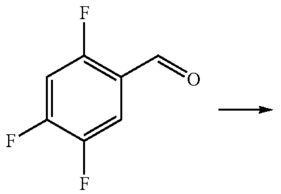

(g)

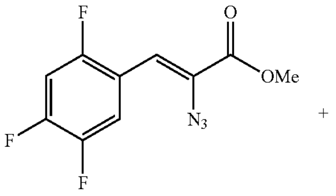

(h-1)

-continued

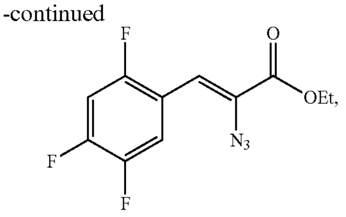

(h-2)

wherein one of Compound (h-1) and Compound (h-2) is produced in excess, for example, an excess of at least 5, 10, 20, 30, 40, 50, 60, 70, 80, 90, or 95%;

(j-4) converting the mixture of Compound (h-1) and Compound (h-2) to the mixture of Compound (i-1) and Compound (i-2) via Hemetsberger indole cyclization:

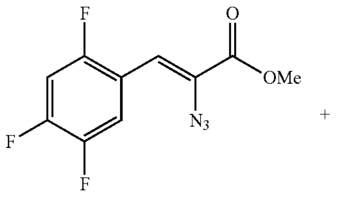

(h-1)

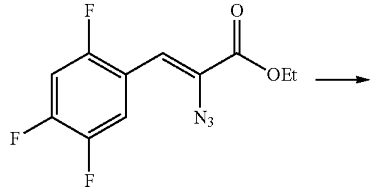

(h-2)

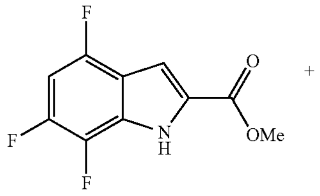

(i-1)

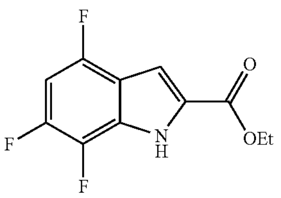

(i-2)

wherein one of Compound (i-1) and Compound (i-2) is produced in excess, for example, an excess of at least 5, 10, 20, 30, 40, 50, 60, 70, 80, 90, or 95%; and (j-5) reacting the mixture of Compound (i-1) and Compound (i-2) with a base to yield Compound (j), or salt thereof:

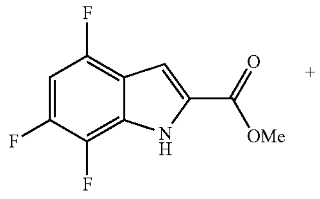

(i-1)

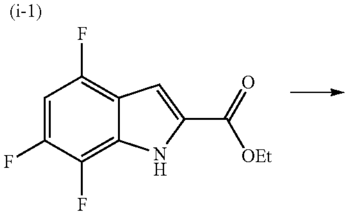

(i-2)

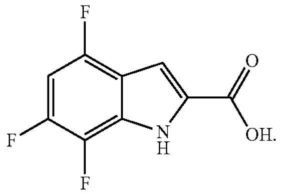

(j)

In another embodiment, the present invention provides a process for preparing Compound (j) or salt thereof (j)

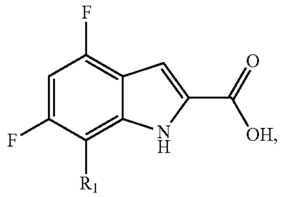

the process comprising the steps of:

(j-1) reducing Compound (g-a) to produce Compound (g-b):

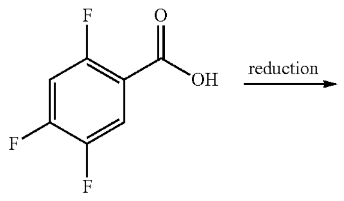

(g-a)

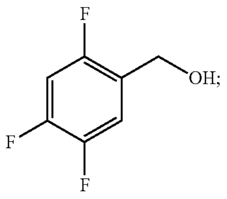

(g-b)

(j-2) oxidizing Compound (g-b) to produce Compound (g):

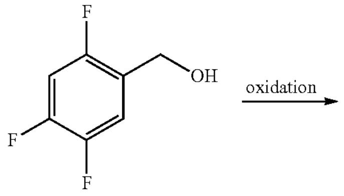

(g-b)

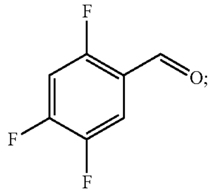

(g)

(j-2a) reacting Compound (g) with sodium bisulfite to produce Compound (g-c):

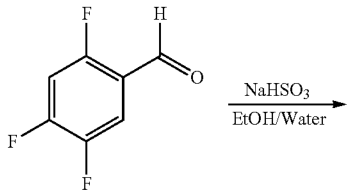

(g)

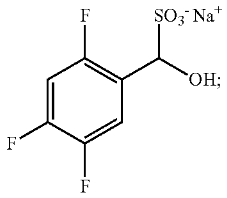

(g-c)

(j-2b) reacting the Compound (g-c) with a base to produce Compound (g):

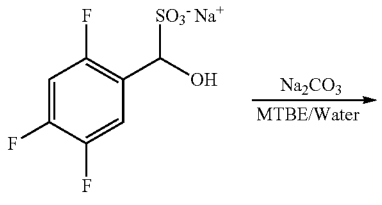

(g-c)

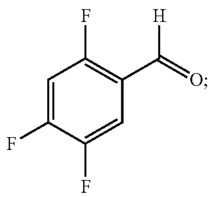

(g)

(j-3) reacting Compound (g) with ethyl 2-azidoacetate in the presence of sodium methoxide as a base to produce a mixture of Compound (h-1) and Compound (h-2):

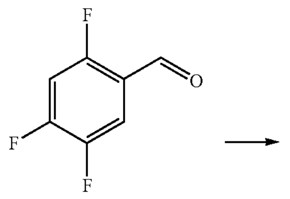

(g)

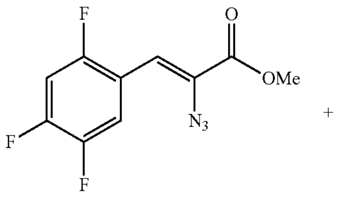

(h-1)

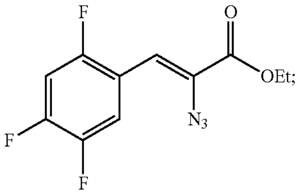

(h-2)

wherein one of Compound (h-1) and Compound (h-2) is produced in excess, for example, an excess of at least 5, 10, 20, 30, 40, 50, 60, 70, 80, 90, or 95%;

(j-4) converting the mixture of Compound (h-1) and Compound (h-2) to the mixture of Compound (i-1) and Compound (i-2) via Hemetsberger indole cyclization:

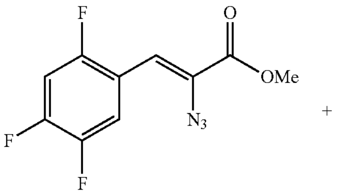

(h-1)

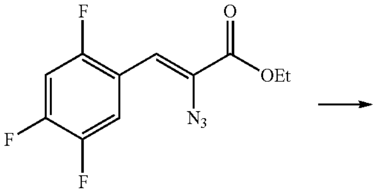

(h-2)

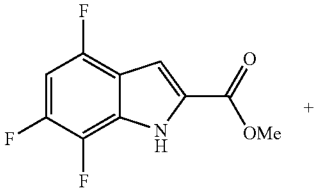

(i-1)

-continued

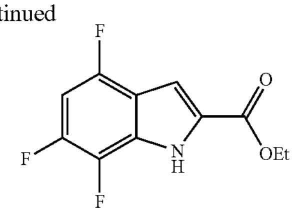

(i-2)

wherein one of Compound (i-1) and Compound (i-2) is produced in excess, for example, an excess of at least 5, 10, 20, 30, 40, 50, 60, 70, 80, 90, or 95%; and (j-5) reacting the mixture of Compound (i-1) and Compound (i-2) with a base to yield Compound (j) or salt thereof:

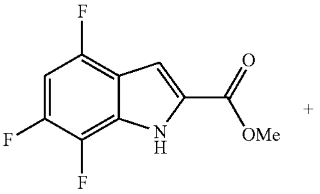

(i-1)

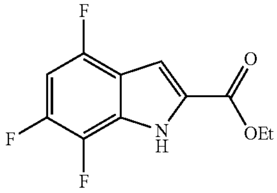

(i-2)

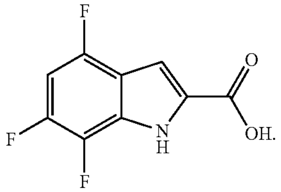

(j)

Step (j-1)

Compound (g-a) is preferably reduced by reaction with a reducing agent. Suitable reducing agents include, but are not limited to, lithium aluminum hydride, lithium borohydride, sodium borohydride, diisobutylaluminum hydride, borane-tetrahydrofuran complex, borane-dimethyl sulfide complex, and the like. Preferably the reducing agent is sodium borohydride or borane-tetrahydrofuran complex.

In preferred embodiments, step (j-1) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and mixtures of two or more thereof. A preferred solvent is tetrahydrofuran.

In one embodiment, the reaction of step (j-1) is conducted at a suitable temperature, for example, from about −20° C. to about 50° C., preferably from about −5° C. to about 25° C. In one embodiment, the reaction takes place over a period from about 0.5 hours to about 12 hours, preferably about 2 to 6 hours.

In certain embodiments, the process of the invention further comprises isolating Compound (g-b), preferably in substantially pure form.

Step (j-2)

Compound (g-b) is oxidized by reaction with an oxidizing agent. Suitable oxidizing agents include, but are not limited to, trichloroisocyanuric acid with TEMPO, sodium hypochlorite (NaClO), sodium hypochlorite with TEMPO, oxalyl chloride with dimethyl sulfoxide, manganese oxide, chromium trioxide, pyridinium chlorochromate (PCC), sodium perchloride, Dess-Martin periodinane (DMP), and the like. A preferred oxidizing agent is sodium hypochlorite with TEMPO.

In preferred embodiments, the reaction in step (j-2) occurs in a solvent. Suitable solvents include, but are not limited to, acetonitrile, acetone, dichloromethane, dimethyl formamide, dimethyl sulfoxide, dioxane, ethyl acetate, heptane, hexane, methyl t-butyl ether, tetrahydrofuran, toluene, and mixtures of two or more thereof. A preferred solvent is methyl tert-butyl ether (MTBE).

The reaction in step (j-2) is conducted at a suitable temperature, for example from about −20° C. to about 50° C., preferably from about −10° C. to about 10° C., and more preferably about from about −5° C. to about 5° C. In certain embodiments, the reaction in step (j-2) takes place for a period from about 10 minutes to about 10 hours, preferably about 30 minutes to about 3 hours.

Step (j-2a)

In one embodiment, the reaction in step (j-2a) occurs in a solvent. Suitable solvents include, but are not limited to, acetonitrile, dioxane, ethyl acetate, methyl tert-butyl ether, tetrahydrofuran, toluene, EtOH, water, and mixtures of two or more thereof. A preferred solvent is a mixture of MTBE, EtOH, and water.

In one embodiment, the reaction in step (j-2a) is conducted at a suitable temperature, for example, from about 0° C. to about 60° C., preferably from about 20° C. to about 40° C. In one embodiment, the reaction takes place over a period from about 0.5 hours to about 12 hours, preferably about 2 to 6 hours.

Step (j-2b)

Step (j-2b) occurs in the presence of a suitable base, such as, but not limited to, sodium carbonate, potassium carbonate, cesium carbonate, sodium hydroxide, sodium methoxide, sodium ethoxide, sodium tert-butoxide, lithium diisopropyl amide, lithium 2,2,6,6-tetramethylpiperidide, sodium diisopropyl amide, lithium bis(trimethylsilyl)amide, sodium bis(trimethylsilyl)amide, triethylamine, diisopropylethylamine, or the like. Preferably, the base is sodium carbonate.

In one embodiment, the reaction in step (j-2b) occurs in a solvent. Suitable solvents include, but are not limited to, acetonitrile, acetone, dimethyl sulfoxide, dioxane, ethyl acetate, methyl tert-butyl ether, tetrahydrofuran, toluene, EtOH, water, and mixtures of two or more thereof. A preferred solvent is methyl tert-butyl ether (MTBE) or a mixture of MTBE and water.

In one embodiment, the reaction in step (j-2b) is conducted at a suitable temperature, for example, from about 0° C. to about 40° C., preferably from about 20° C. to about 25° C. In one embodiment, the reaction takes place over a period from about 0.5 hours to about 12 hours, preferably about 2 to 6 hours.

In certain embodiments, the process of the invention further comprises isolating Compound (g), preferably in substantially pure form.

Step (j-3)

In preferred embodiments, step (j-3) occurs in presence of a sacrificial electrophile, such as, but not limited to, $CF_3CO_2Et$, ethyl trichloroacetate or ethyl formate, to prevent hydrolysis in the base-catalyzed condensation reaction and thereby improve the yield. A preferred sacrificial electrophile is $CF_3CO_2Et$.

In preferred embodiments, step (j-3) occurs in a suitable solvent, such as, but not limited to, dichloromethane, chloroform, dioxane, ethyl acetate, heptane, hexane, methyl t-butyl ether, tetrahydrofuran, methanol, ethanol, or toluene, and mixtures of two or more thereof. Preferably, the solvent is methanol or ethanol. More preferably, the solvent is methanol.

The reaction of step (j-3) is conducted at a suitable temperature, for example from about −10° C. to about 10° C., preferably from about −5° C. to about 10° C., and more preferably about 0° C. In one embodiment, step (j-3) takes place for a period from about 30 minutes to about 10 hours, preferably about 5 hours to about 24 hours, and more preferably about 8 hours to about 14 hours.

In certain embodiments, the process of the invention further comprises isolating Compound (h-1), preferably in substantially pure form.

Step (j-4)

In step (j-4), Compound (h-1) is heated to generate the active intermediate, which can cyclize to form Compound (i-1) and Compound (i-2).

In preferred embodiments, step (j-4) occurs in a solvent. Suitable solvents include, but are not limited to, trimethylbenzene, dichloromethane, chloroform, dioxane, ethyl acetate, heptane, hexane, methyl t-butyl ether, tetrahydrofuran, methanol, xylene, and toluene, and mixtures of two or more thereof. Preferably the solvent is a mixture of xylene and methanol. Preferably the volume ratio of xylene to methanol is greater than 1. More preferably the volume ratio of xylene to methanol is 5:1.

In certain embodiments, step (j-4) is conducted in a flow reactor, and Compound (i-1) and Compound (i-2) are prepared via continuous flow chemistry technology, and carried out at a suitable temperature, such as for example from about 100° C. to about 300° C., preferably from about 150° C. to about 250° C., and more preferably about 200° C. In one embodiment, step (j-4) takes place with residence time in about 10 minutes to about 6 hours, preferably in about 25 minutes.

In preferred embodiments, the process of the invention further includes isolating Compound (i-1), preferably in substantially pure form.

Step j-5)

Step (j-5) is the saponification of Compound (i-1) and/or Compound (i-2) in the presence of a suitable base followed by treatment with an acid to form Compound (j). Suitable bases include, but are not limited to, sodium hydroxide, potassium hydroxide, lithium hydroxide, or combinations of two or more thereof. A preferred base is sodium hydroxide. Suitable acids include, but are not limited to, hydrogen chloride, hydrogen bromide, sulfuric acid and combinations of two or more thereof. A preferred acid is hydrogen chloride.

In preferred embodiments, step (j-5) occurs in a solvent. Suitable solvents include, but are not limited to, dichloromethane, chloroform, dioxane, ethyl acetate, heptane, hexane, methyl t-butyl ether, tetrahydrofuran, water, toluene, and mixtures of two or more thereof. Preferably the solvent is mixture of tetrahydrofuran and water or MTBE and water.

In certain embodiments, step (j-5) is carried out at a suitable temperature, such as for example from about 30° C. to about 100° C., preferably from about 55° C. to about 65° C., and more preferably about 65° C. In one embodiment, step (J-5) takes place for a period from about 1 hour to about 3 days, preferably from about 10 hours to about 2 days, and more preferably about 24 hours.

In preferred embodiments, the process of the invention further includes isolating Compound (j), preferably in substantially pure form.

In certain embodiments, the invention provides a method of producing the Compound (I) comprising steps (1), (2), (3), (4), (5), (6), (7), (j-1), (j-2), (j-3), (j-4), (j-5), (8), and (9) described above.

In certain embodiments, the invention provides a method of producing the Compound (I) comprising steps (1), (2), (3), (4), (5), (6), (7), (j-1), (j-2), (j-2a), (j-2b), (j-3), (j-4), (j-5), (8), and (9) described above.

In certain embodiments, the invention provides a method of producing the Compound (I) comprising steps (1), (2), (3), (4), (5), (6), (7), j-3), (j-4), (j-5), (8), and (9) described above.

Definitions

Listed below are definitions of various terms used to describe this invention. These definitions apply to the terms as they are used throughout this specification and claims, unless otherwise limited in specific instances, either individually or as part of a larger group.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with an exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo [2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The term "sulfonyl group" refers to a group of the formula $R_a$—$SO_2$—, where $R_a$ is an alkyl, alkenyl, alkynyl or aryl group, each optionally substituted. Preferably, $R_a$ is optionally substituted alkyl or optionally substituted aryl.

The term "phosphoryl group" refers to a group of the formula $(R_b)_2P(O)$—, where $R_b$ is an alkyl-O—, alkenyl-O—, alkynyl-O— or aryl-O— group, each optionally substituted. Preferably, $R_b$ is optionally substituted alkyl, such as $C_1$-$C_3$-alkyl.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH— heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)— heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH— heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH—heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2$NH—$C_1$-$C_{12}$-alkyl, —$SO_2$NH—$C_2$-$C_8$-alkenyl, —$SO_2$NH—$C_2$-$C_8$-alkynyl, —$SO_2$NH—$C_3$-$C_{12}$-cycloalkyl, —$SO_2$NH-aryl, —$SO_2$NH-heteroaryl, —$SO_2$NH-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. It is understood that the aryls, heteroaryls, alkyls, cycloalkyls and the like can be further substituted.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure (s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl(trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery*, (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards Part*-2, (Biotechnology: Pharmaceutical Aspects), edited by V. J. Stella, et al, Springer and AAPSPress, 2007, pp 31-99.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 9-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups;

sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* 2nd Ed. Wiley-VCH (1999); T. W. Greene and P. G. M. Wuts, *Protective Groups in Organic Synthesis,* 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus, a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

Abbreviations

Abbreviations which may be used in the descriptions of the scheme and the examples that follow are:

DMAP for dimethylaminopyridine;
DMF for dimethyl formamide;
DCM for dichloromethane;
AcOH for acetic acid;
EtOAc or EA for ethyl acetate;
Cbz for benzyloxycarbonyl;
HCl for hydrogen chloride;
HBr for hydrogen bromide;
$NaHCO_3$ for sodium bicarbonate;
HPLC for high-pressure liquid chromatography;
MeOH for methanol;
MTBE for tert-butyl methyl ether;
EtOH for ethanol;
Fmoc for fluorenylmethoxycarbonyl;
Troc for 2,2,2-trichloroethoxycarbonyl;
Moz for p-methoxybenzyloxycarbonyl;
Pnz for p-nitrobenzyloxycarbonyl;
Teoc for 2-(trimethylsilyl)ethoxycarbonyl;
NMM for N-methylmorpholine;
HATU for 1-[bis(dimethylamino)methylene]-1H-1,2,3-triazolo[4,5-b]pyridinium 3-oxide hexafluorophosphate;
N-bromosuccinimide (NBS)
Rp for hydroxyl protecting group;
TEA for triethylamine;
THE for tetrahydrofuran;
2-Me THE for 2-methyltetrahydrofuran;
TFAA for trifluoroacetic anhydride;
TsOH for p-toluenesulfonic acid;
TPP or $PPh_3$ for triphenylphosphine;
T3P for n-propanephosphonic acid anhydride;
Boc for t-butoxycarbonyl;
Bz for benzyl;
Ph for phenyl;
PhMe for toluene.

All other abbreviations used herein, which are not specifically delineated above, shall be accorded the meaning which one of ordinary skill in the art would attach.

Synthetic Schemes

The present invention will be better understood in connection with Schemes 1, 2, 3, wherein $R_1$, $R_2$, $R_3$ are as previously defined unless otherwise indicated. It will be readily apparent to one of ordinary skill in the art that the process of the present invention can be practiced by substitution of the appropriate reactants and that the order of the steps themselves can be varied.

A chemical route to the synthesis of amide HCl salt (f-1) is summarized in Scheme 1. The commercially available compound (a) can react with formaldehyde to undergo Pictet-Spengler reaction to form the bicyclic compound (b) as a HCl salt. Compound (b) can be protected to generate compound (c) as a Boc amine. Compound (c) can be treated with NBS to undergo an arrangement to generate spirooxindole compound (d-1) and compound (d-2) as the mixture of diastereomer, which were converted to the corresponding amide compound (e-1) and compound (e-2) via aminolysis. The mixture of compound (e-1) and (e-2) were treated with HCl to cleave the Boc group followed by recrystallization in DMF to generate key intermediate compound (f-1) as the DMF solvate in high purity.

Scheme 1

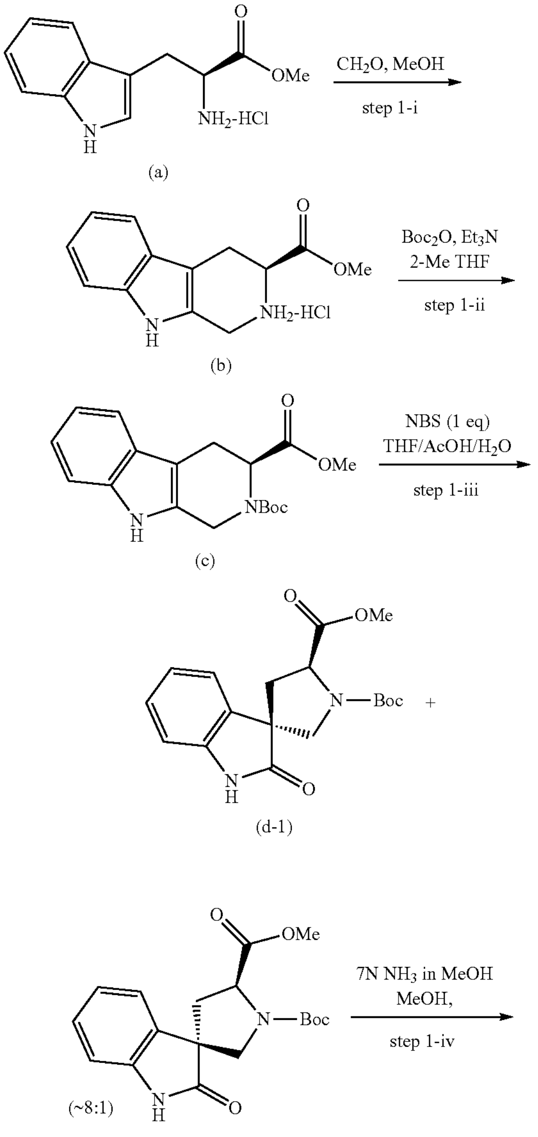

(a)

(b)

(c)

(d-1)

+

(~8:1)

(d-2)

-continued

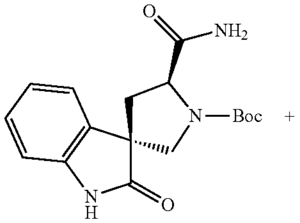

(e-1)

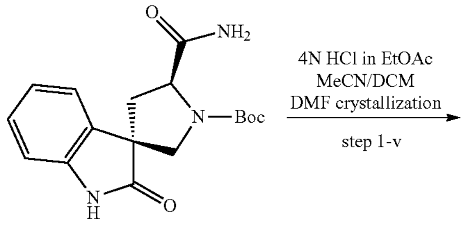

(e-2)

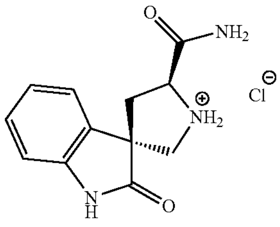

(f-1)

A chemical route to the synthesis of 2-indole carboxylate compound (j) is summarized in Scheme 2. The commercially available compound (g-a) can be reduced and then oxidized to yield compound (g). Compound (g) reacts with ethyl 2-azidoacetate in the presence of base and sacrificial electrophile (i.e. ethyl trifluoroacetate) to undergo condensation reaction to form the acrylate compound (h). Compound (h) is then subjected to Hemetsberger indole cyclization using continuous flow chemistry process to yield Compound (i) as the 2-indole carboxylate. Saponification of compound (i) provides key intermediate compound (j) as 2-indole carboxylic acid.

Scheme 2

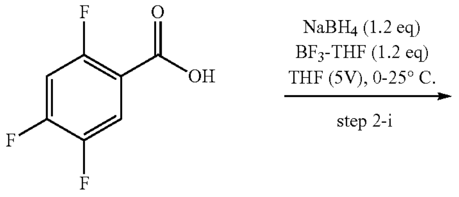

(g-a)

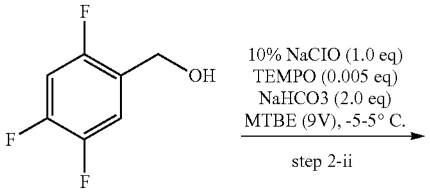

(g-b)

-continued

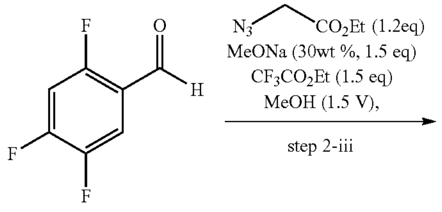

(g)

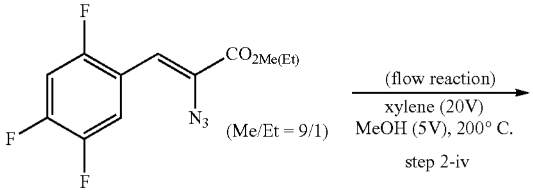

(h)

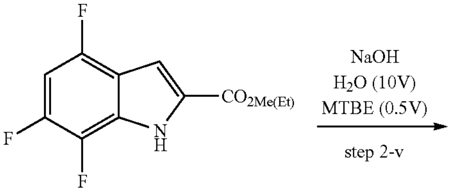

(i)

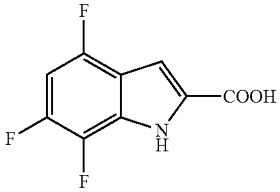

(j)

An alternative chemical route to the synthesis of 2-indole carboxylate compound (j) is summarized in Scheme 2a. The commercially available compound (g-a) can be reduced to alcohol (g-b). oxidized to yield compound (g). Compound (g) reacts sodium bisulfite to form its sodium bisulfite salt (g-c). After the treatment of base (i.e. sodium carbonate), sodium bisulfite (g-c) liberates compound (g), which reacts with ethyl 2-azidoacetate in the presence of base and sacrificial electrophile (i.e. ethyl trifluoroacetate) to undergo condensation reaction to form the acrylate compound (h). Compound (h) is then subjected to Hemetsberger indole cyclization using continuous flow chemistry process to yield Compound (i) as the 2-indole carboxylate. Saponification of compound (i) provides key intermediate compound (j) as 2-indole carboxylic acid.

Scheme 2a

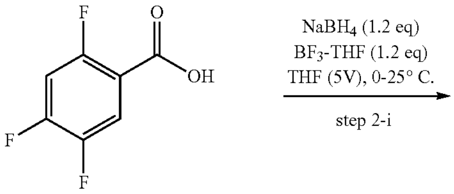

(g-a)

-continued

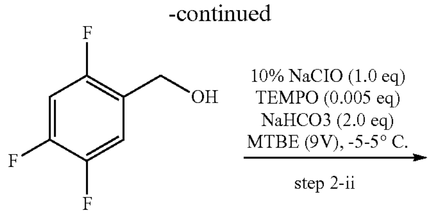

(g-b)

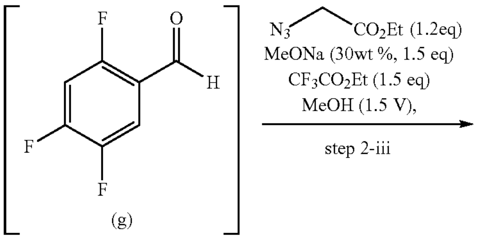

(g)

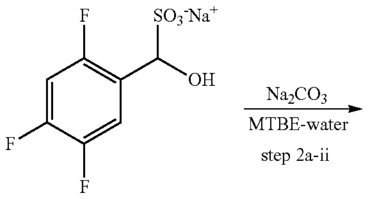

(g-c)

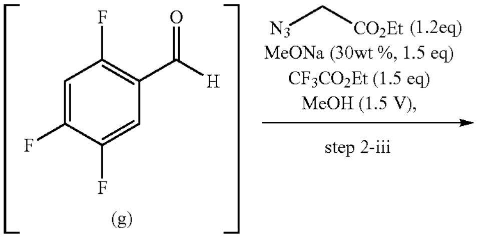

(g)

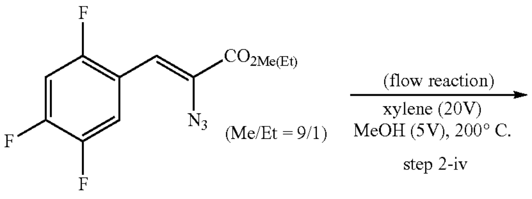

(h)

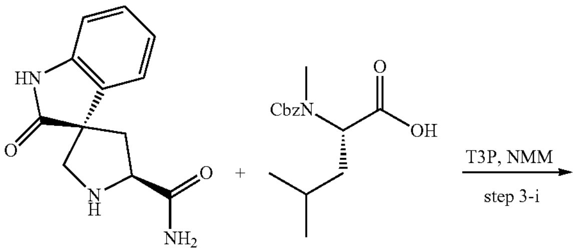

(f-1)

(k)

-continued

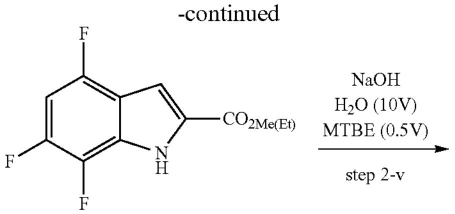

(i)

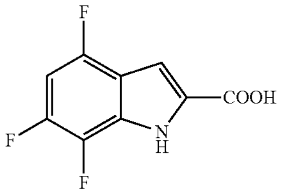

(j)

A chemical route to the synthesis of 2-indole carboxylate compound (I) is summarized in Scheme 3. Compound (f-1) can react with commercially available compound (k) under amide coupling condition to provide compound (l). A suspension of compound (l) and Pd/C catalyst in methanol is stirred under hydrogen atmosphere to enable the Cbz deprotection reaction to generate the secondary amine compound (m-1). Alternatively, a suspension of compound (l) and Pd/C catalyst in methanol is stirred under hydrogen atmosphere in the presence of acid to yield compound (m-2) as the acid salt. Alternatively, compound (l) can be treated with strong acid (such as HBr in HOAc) to enable the Cbz deprotection reaction to generate the secondary amine compound (m-3) as the acid salt. A mixture of compound (m-1), compound (j), coupling reagent (i.e. HATU), and base (i.e. NMM) in DMF is stirred to complete the coupling reaction to afford compound (n). Similar reaction condition is also applicable to compound (m-2) or (m-3) to yield compound (n). Compound (n) can undergo dehydration reaction to convert amide to as nitrile, which can be further purification by toluene crystallization to yield compound (o) as the toluene solate. The isolated toluene solvate solid is dissolved in EtOH and added to water to form a suspension. The amorphous solid product is filtered, washed with water, and dried to afford compound (I) as the amorphous solid.

-continued
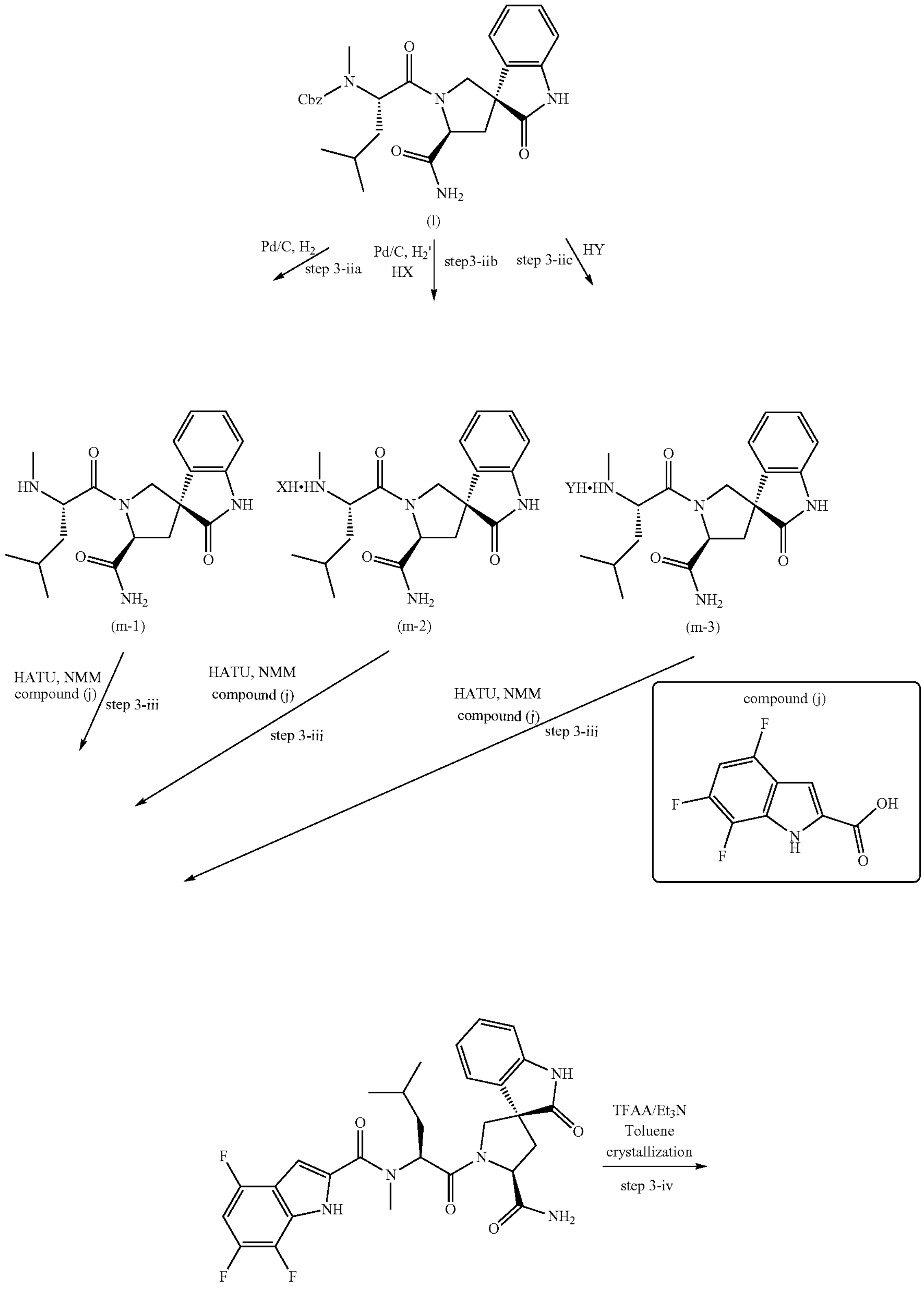
(n)

-continued

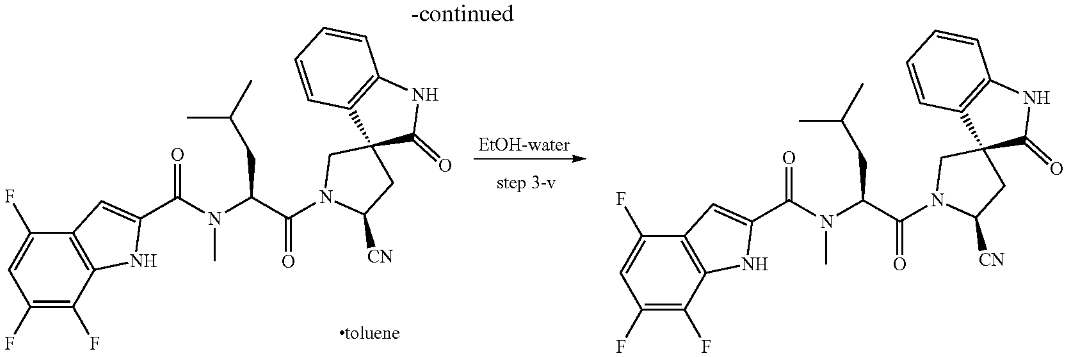

•toluene

Compound(I)

Compound(I)
Amorphous

The compounds and processes of the present invention will be understood in connection with the following illustrative methods by which the compounds of the invention may be prepared. It will be understood that any of the reactions described herein, in any of its variations, can be combined with one or more of the other reactions, in any of their respective variations, substantially in analogy with Scheme 1 above.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1. Preparation of Methyl Ester (b)

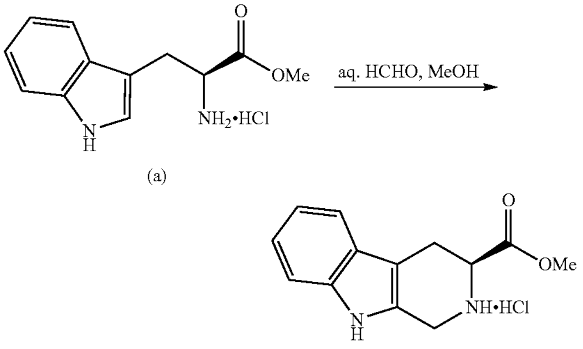

(a)

(b)

To a stirring solution of compound a (70.0 kg, 274.8 mol, 1.0 eq) in MeOH (700 L) was added 37 wt % formaldehyde aqueous (24.6 kg, 302.3 mol, 1.1 eq) dropwise within 1 h at 65° C., and the resulting solution was stirred at 65° C. for 30 min. HPLC showed compound b was completely consumed. The reaction mixture was concentrated in vacuo to approximately 60 kg while a white solid was precipitated. MTBE (840 L) was added, and the resulting white suspension was stirred at 20° C. for 2 h. The mixture was filtered, and the filter cake was washed with MTBE (70 L), and dried under vacuum to afford compound b as the methyl ester (71.0 kg, 100.0% purity, 98.9% assay, 95.7% yield). $^1$H-NMR (300 MHz, $CDCl_3$): $^1$H NMR (400 MHz, DMSO): δ 11.19 (s, 1H), 10.24 (s, 2H), 7.48 (d, J=7.8 Hz, 1H), 7.37 (d, J=8.1 Hz, 1H), 7.16-7.06 (m, 1H), 7.06-6.96 (m, 1H), 4.63 (dd, J=10.1, 5.3 Hz, 1H), 4.40 (s, 2H), 3.83 (s, 3H), 3.33-3.26 (m, 1H), 3.07 (dd, J=15.9, 10.1 Hz, 1H).

Example 2. Preparation of Boc Amine (c)

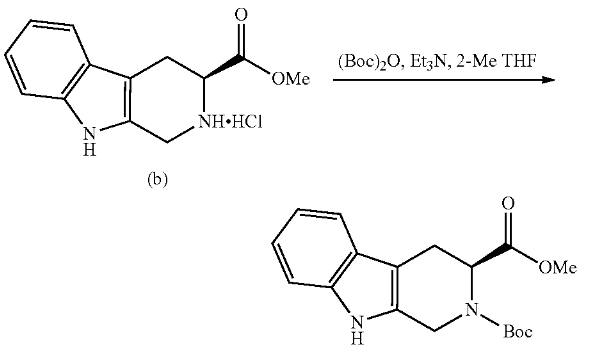

(b)

(c)

To a stirring suspension of compound b (70.0 kg, assay: 98.9%, 259.6 mol, 1.0 eq) in 2-MeTHF (643.8 kg) was added TEA (54.2 kg, 535.6 mol, 2.06 eq) at 5° C., and $H_2O$ (156.8 kg) was added. The resulting solution was stirred at 5~10° C. for 20 min. $(Boc)_2O$ (61.8 kg, 283.2 mol, 1.09 eq) was added. The reaction mixture was warmed to 25° C., and stirred at 25° C. for 5 h. The reaction mixture was cooled to 5° C., and 7 wt % HCl aqueous (208.5 kg, 400.0 mol, 1.54 eq) was slowly added. The mixture was separated, the aqueous layer was extracted with 2-Me THF (100 kg). The combined organic layer was washed with 5% sodium bicarbonate solution (109.1 kg) and 5% NaCl aq. (144.8 kg) to afford the solution (690.2 kg) of compound c in 2-methyltetrahydrofuran, which was used into the next step without further purification. $^1$H NMR (300 MHz, $CDCl_3$) δ 8.69 (s, 0.5H), 8.05 (s, 0.5H), 7.50 (d, J=7.6 Hz, 1H), 7.36-7.26 (m, 1H), 7.21-7.05 (m, 2H), 5.44 (d, J=5.5 Hz, 0.5H), 5.23 (d, J=5.3 Hz, 0.5H), 4.93 (d, J=16.1 Hz, 0.5H), 4.83 (d, J=16.2 Hz, 0.5H), 4.57 (dd, J=16.1, 11.1 Hz, 1H), 3.62 (d, J=8.7 Hz, 3H), 3.44 (d, J=15.6 Hz, 1H), 3.12 (m, 1H), 1.55 (d, J=3.0 Hz, 9H).

Example 3. Preparation of Compound (d-1) and Compound (d-2) as the Mixture of Diastereomers

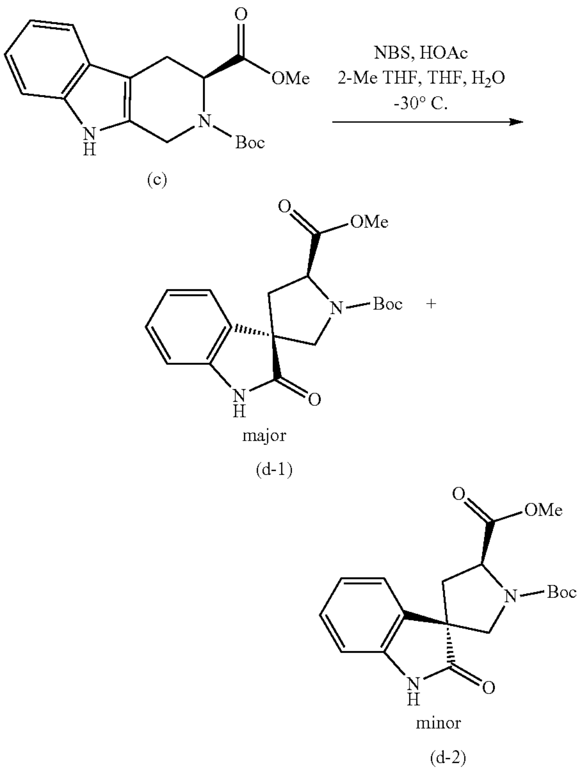

(c)

major (d-1)

minor (d-2)

To a solution of compound (c) in 2-MeTHF (688.5 kg, 259.6 mol, 1.0 eq) was added $H_2O$ (220.6 kg) and THF (312.3 kg) at 0° C., and AcOH (113.0 kg, 1881.7 mol, 7.2 eq) was added at 0° C. The cloudy mixture was cooled to −30° C. while it became a milky solution. NBS (46.9 kg, 263.5 mol, 1.0 eq) was added in 10 portions with interval 20 min at −30° C. The milky mixture became a yellow cloudy solution and was stirred at −30° C. for 30 min. HPLC showed compound 3 was completely consumed. The cloudy yellow solution was warmed to −10° C. and poured into a stirring 15 wt % $K_2CO_3$ aqueous (1156.5 kg). The mixture was separated, and the aqueous layer was extracted with DCM (370.6 kg). The combined organic layers were washed with 15 wt % $K_2CO_3$ aqueous (289.4 kg) and 10 wt % NaCl aqueous (286.4 kg×3), and concentrated under vacuum to 1/4 volume. DCM, THE and 2-MeTHF were removed by azeotropic distillation with MeOH (221.5 kg×3) to give a solution of Compound (d-1) and Compound (d-2) in MeOH (174.1 kg) which was used directly to the next step.

$^1$H NMR (400 MHz, DMSO): δ 10.66 (s, 1H), 7.23 (t, J=7.7 Hz, 1H), 7.08 (dd, J=15.3, 7.2 Hz, 1H), 7.00 (dd, J=10.2, 4.5 Hz, 1H), 6.90 (d, J=7.7 Hz, 1H), 6.84 (d, J=7.6 Hz, 1H), 4.61 (dt, J=13.8, 8.5 Hz, 1H), 3.71 (d, J=12.5 Hz, 3H), 3.54 (dt, J=26.9, 10.1 Hz, 2H), 2.39 (dd, J=12.8, 8.0 Hz, 1H), 2.25 (ddd, J=18.5, 12.8, 9.1 Hz, 1H), 1.41-1.36 (m, 9H).

Example 4. Preparation of Amide Compound (e-1) and Compound (e-2) as a Mixture of Diastereomers

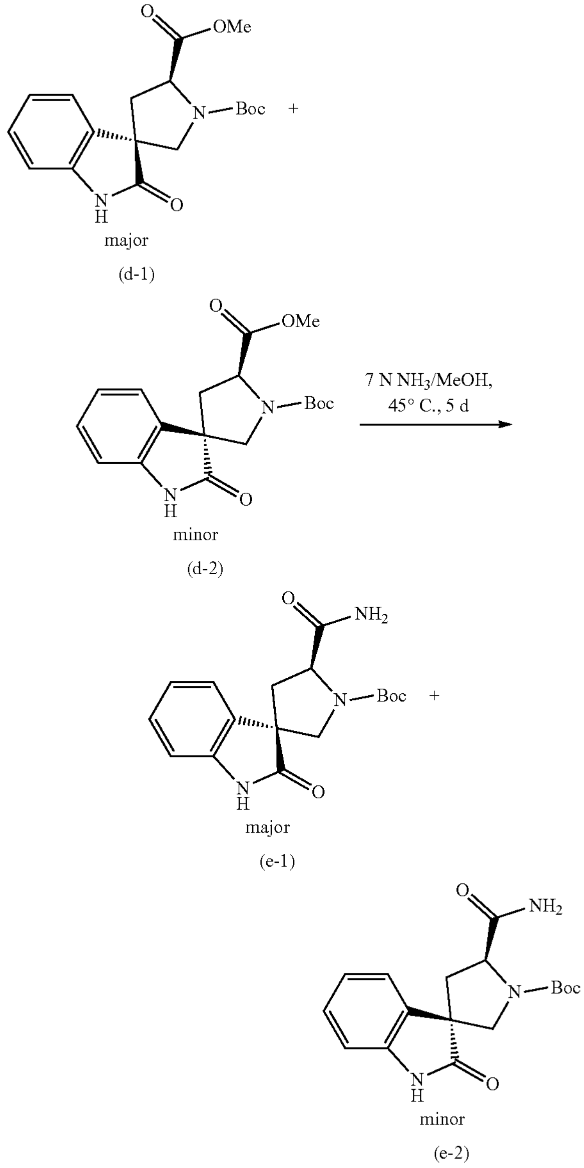

major (d-1)

minor (d-2)

major (e-1)

minor (e-2)

To a solution of compound (d-1) and compound (d-2) in MeOH (174.2 kg, 259.6 mol, 1.0 eq) was added 7 N $NH_3$ in MeOH (568.1 kg, 20 eq) at 25° C., and the reaction mixture was stirred at 50~55° C. in an autoclave for 5 d. The mixture was cooled and concentrated under vacuum to half volume. DMF (172.4 kg) and PhMe (93.5 kg) were added, and the mixture was concentrated under vacuum to afford the dark brown solution of Compound (e-1) and Compound (e-2) in DMF and toluene (222.1 kg) which was used to the next step without further purification.

$^1$H NMR (400 MHz, DMSO): δ 10.65 (s, 1H), 7.51 (d, J=7.0 Hz, 1H), 7.24 (t, J=7.6 Hz, 1H), 7.09 (d, J=25.4 Hz, 1H), 7.04-6.94 (m, 2H), 6.92 (t, J=5.5 Hz, 1H), 4.50-4.36 (m, 1H), 3.57-3.50 (m, 2H), 2.20 (t, J=6.8 Hz, 2H), 1.38 (m, 9H).

Example 5. Preparation of Compound (f-1)

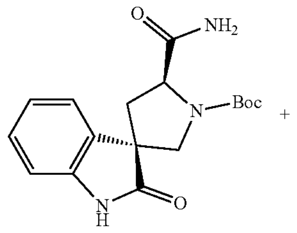

major
(e-1)

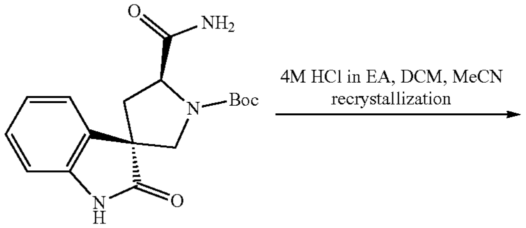

minor
(e-2)

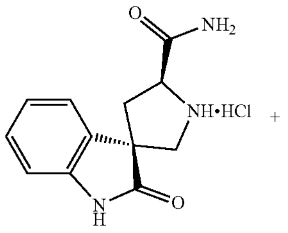

(f-1)

+

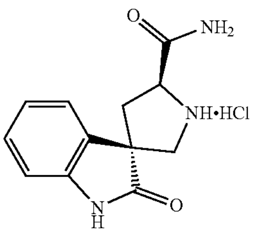

(f-2)
removed in crystallization

To DCM (2288.5 kg) was added 4 M HCl in EA (440.8 kg) at 25° C., and the solution of compound (e-1) and (e-2) in DMF and PhMe (222.1 kg, 259.6 mol) and Acetonitrile (135.5 kg) were added at 25° C. The reaction mixture stirred at 25±5° C. for 2 d. HPLC showed the reaction was completed. The mixture was filtered, and the filter cake was washed with DCM (357.5 kg) and dried under vacuum to give crude product (72.1 kg). The crude product was added into hot DMF (205.0 kg) at 55° C., and the mixture was stirred at 55° C. for 3 h. The mixture was then cooled to 10±5° C. within 6 h and then stirred for 2 h. The mixture was filtered, and the filter cake was washed with DMF (67.8 kg) and DCM (228.9 kg), and dried under vacuum at 30° C. to afford Compound (f-1) (40.0 kg, 99.5% purity, 76.3% assay, 43.9% yield for 4 steps) as a yellowish solid. $^1H$ NMR (400 MHz, DMSO): δ 11.00 (s, 1H), 10.78 (s, 1H), 9.06 (s, 1H), 8.03 (s, 1H), 7.77 (s, 1H), 7.63 (d, J=7.4 Hz, 1H), 7.27 (td, J=7.7, 1.0 Hz, 1H), 7.04 (td, J=7.6, 0.8 Hz, 1H), 6.91 (d, J=7.7 Hz, 1H), 4.64 (dd, J=11.0, 7.3 Hz, 1H), 3.59 (d, J=12.3 Hz, 1H), 3.45 (d, J=12.2 Hz, 1H), 2.47 (m, 1H), 2.22 (m, 1H).

Example 6. Preparation of Compound (g-b)

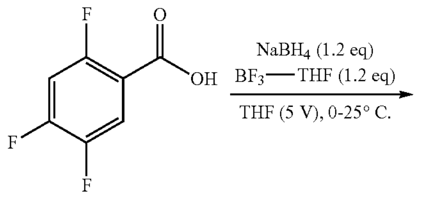

(g-a)

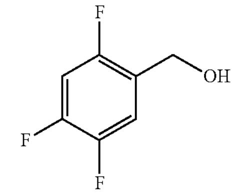

(g-b)

Charge compound (g-a) (340.0 kg, 1.0 eq) and THF (1513.0 L, 5V) into reactor 1 (R1). Cool Reactor 1 to 0~10° C. Add $NaBH_4$ (87.7 kg, 1.2 eq) into R1 at/at 0~10° C. and stirred at 0~10° C. for 1~2 h. Add $BF_3$-THF (324.0 kg, 1.2 eq) drop-wisely into R1 at 0~10° C. (recommend 0~5° C.) and stir at 0~10° C. for 0.5~1 h. R1 was warmed up to 15~25° C. and stirred for 2~3 h. Sample for IPC (HPLC) (quenched with saturated $NH_4Cl$ aq, EP-038282-A≤2.0%). Water (1500 L, 4.4V) and $NH_4Cl$ (550.8 kg) were charged into Reactor 2 (R2) to prepare $NH_4Cl$ aq. The reaction mixture in R1 was added slowly into $NH_4Cl$ aq in R2 at 20~30° C. and R2 was stirred at 20~30° C. for 2~3 h. After separation, collect the organic phase in R2, and transform aqueous phase to R1. R2 was concentrated until there was no obvious distillate out below 50° C. MTBE (1360 L, 4V) was added to R1, and R1 was stirred for 0.5 h. After separation, the organic phase was collected and transferred to R2. MTBE (1360 L, 4V) was added to R1 and the MTBE was transferred to R2. The slurry in R2 was stirred at 20~30° C. for 10~20 min. After filtration, the cake was washed with MTBE (340 L, 1V). All filtrate in R1 was collected and the crude compound (g-b) was used for next step directly.

Example 7. Preparation of Compound (g)

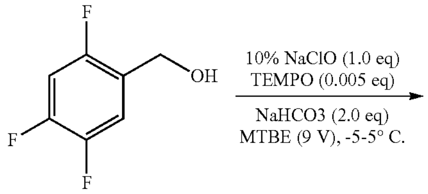

(g-b)

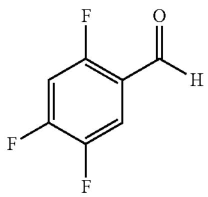

(g)
neat or in solution $NaHCO_3$ (324.4 kg, 2.0 eq) and TEMPO (1.5 kg, 0.005 eq) into the solution of compound (g-b) from the previous step (Example 6) in R1. R1 was cooled to −5~5° C. (recommend 0° C.) and 10% NaClO aq. was added dropwise into R1 at −5~5° C. (recommend 0° C.). R1 was stirred at −5~5° C. (recommend 0° C.) for 2~3 h. Sample for IPC (HPLC) (detect top layer organic phase, compound (g-b) ≤2.0%). If compound (g-b)>2.0%, 10% NaClO aq. was added until IPC results was qualified. $Na_2SO_3$ (10.2 kg) and water (23.8 kg) were added to Reactor 2 (R2) to make 30% $Na_2SO_3$ aq. The reaction in R1 was quenched with 30% $Na_2SO_3$ aq. in R2 (detect with KI-starch test paper) before filtering the slurry. After filtration, the cake was washed with MTBE (340 L, 1V) and all filtrate in R2 was collected. Anhydrous $MgSO_4$ (39.1 kg) was added into R2 and stirred at 20~30° C. for 20~30 min. After filtration, the cake was washed with MTBE (340 L, 1V) and all filtrate in R1 was collected. The aldehyde (g) in MBTE solution can be used in Experiment 20. Alternatively, R1 was concentrated to no obvious distillate below 30° C. to obtain crude compound (g) as orange oil, which was transferred to distillation reactor R3. R3 was distilled to no obvious distillate out below 30° C. under vacuum ≤0.085 MPa, and then distilled at 60~100° C. (recommend 70~80° C.) under vacuum ≥0.090 MPa to collect the distillate. The purified compound (g) (273.6 kg, 88% yield) was obtained as colorless to orange oil.

$^1$H-NMR ($CDCl_3$): δ 10.23 (s, 1H), 7.64-7.70 (m, 1H), 7.04-7.10 (m, 1H)

Example 8. Preparation of Compound (h-1) and (h-2) as the Acrylate

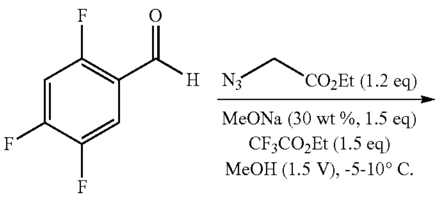

(g)

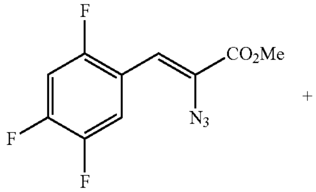

(h-1)

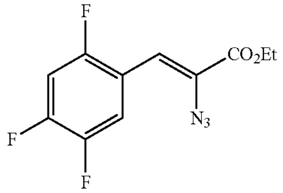

(h-2)

To the reactor was charged Compound (g) (100 kg, neat, 1.0 eq, prepared using the procedure in experiment 7, or Compound (g), 100 kg in MeOH solution, prepared using the procedure in experiment 21, $CF_3CO_2Et$ (133.1 kg, 1.5 eq) and MeOH (150 L, 1.5V). The reactor was cooled −5~5° C. (recommend −5~0° C.) and Ethyl azidoacetate (96.8 kg, 1.2 eq) was added at −5~5° C. (recommend 0° C.). Then MeONa (56.2 kg, 0.5 eq, 30 wt % in MeOH) was added drop-wisely into the reactor at −5~0° C. The reaction mixture was stirred at −5~5° C. for 2~3 hours before MeONa (56.2 kg, 0.5 eq, 30 wt % in MeOH) was added drop-wisely into the reactor at −5~0° C. The mixture was stirred at −5~5° C. for 2~3 h then MeONa (56.2 kg, 0.5 eq, 30 wt % in MeOH) was added drop-wisely at −5~0° C. The reaction mixture was stirred at −5~5° C. for 2~3 h and then at 0~10° C. (recommend 5° C.) for 8~14 h. The reaction mixture was slowly added into 2.5 wt % $NH_4Cl$ (aq) in R2 at 0~10° C. After filtration, collect the cake and wash with water (600 L, 3V×2). The crude compound (h-1) and (h-2) was used for next step directly without further purification.

$^1$H NMR (400 MHz, DMSO-$d_6$) δ 3.85-3.90 (s, 3H), 6.75-6.86 (s, 1H), 7.53-7.74 (td, J=6.9, 10.6 Hz, 1H), 8.17-8.31 (ddd, J=6.9, 9.2, 12.1 Hz, 1H).

Example 9. Preparation of Methyl/Ethyl indole-2-carboxylate (i-1)/(i-2)

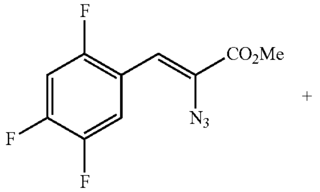

(h-1)

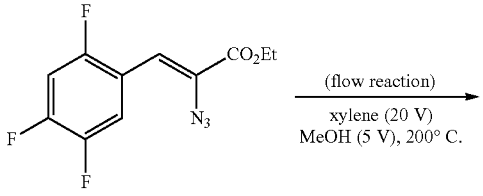

(h-2)

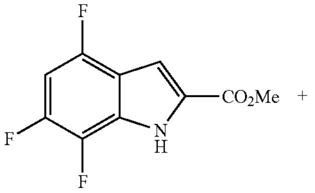

(i-1)

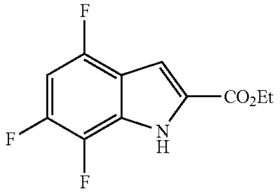

(i-2)

Solution A: To the reactor R1 was charged xylene (20V) into R1. Adjust R1 to 5° C. (0-10° C.). Charged wet cake of mixture of compound (h-1) and (h-2) into R1. Stirred for 1 hour (0.5~1.5 hour) at 5° C. (0-10° C.) before charging process water (5V) into R1 at 5° C. (0~10° C.). Stirred for 20 min (10-30 min) at 5° C. (0-10° C.) and stood for 20 min (10~30 min) at 5° C. (0-10° C.) to allow phase separation. Removed the bottom aqueous layer. The upper organic layer was filtered and used as Solution A.

Solution B: and MeOH (5V) was used as Solution B.

The Flow Procedure (10 L facility) is shown schematically in FIG. 1 and described below:

Transferred the above solution A to FLV1 (1, flow liquid tank 1) via the filter in batches. Transferred the Fresh Methanol (solution B) to FLV2 (4, flow liquid tank 2). Placed FLR1 (flow liquid reactor 1) in oven 1 (3) and controlled FLR1 at 195-205° C. (Target 200° C.). Placed post-heating tubing (FLR2) into Water/EG bath (7) and controlled post-heating tubing (FLR2) at 50~60° C. by temperature control unit (Target 55° C.). Set the pressure value of Back Pressure Valve (8) at 1.8-2.0 MPa. Set the flow rate of Pump 1 (2) and Pump 2 (5) based on residence time 25 min. Then continuously transferred the solution A in FLV1 into FLR1 by Pump 1 via valve (6), and transferred the MeOH solvent in FLV2 into FLR2 by pump 2 via valve (6) and transferred the solution in FLR2 into product tank (9) respectively.

A sample was taken for IPC (HPLC, every 2~6 h). After the flow process was finished, the combined reaction mixture was charged into the reactor and concentrated until there was no obvious distillate out below 70° C. (the distillate was collected for recycle). Xylene (4.3 kg, 5V) was added into the reactor and concentrated until there was no obvious distillate out below 70° C. (the distillate was collected for recycle). Xylene (2.6 kg, 3V) was added into R1, then the reaction mixture was cooled to −5~5° C. (recommend 0~5° C.) and stirred at −5~5° C. for 2~5 h. After centrifugation, the crude cake was washed with xylene (0.43 kg, 0.5V) and the resulting crude mixture of Compound (i-1) and Compound (i-2) (mixture of methyl ester and ethyl ester, ratio is about 9/1) was used for the next step directly without further purification.

NMR: $^1H$ NMR (300 MHz, DMSO-$d_6$) δ 12.87 (s, 1H), 7.08 (d, J=2.7 Hz, 1H), 7.02 (ddd, J=11.5, 9.7, 5.2 Hz, 1H), 3.75 (s, 3H).

Example 10. Preparation of indole-2-carboxylic Acid Compound (j)

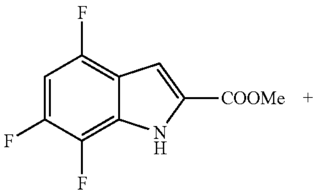

(i-1)

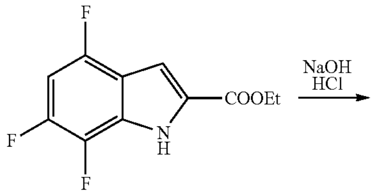

(i-2)

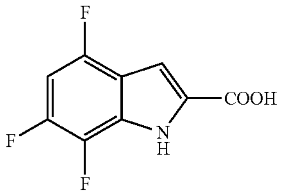

(j)

NaOH (22 kg, 2.5 eq) and $H_2O$ (100 kg, 10V) were charged into reactor R1 to make aqueous NaOH solution. A crude mixture of i-1/i-2 (50 kg, 1.0 eq) and MTBE (18.5 kg, 0.5V) were charged into reactor R1. R1 was heated to 55~65° C. and stirred at such temperature for 3~6 h. After the reaction was complete, R1 was cooled to 0~10° C. Aqueous HCl (36%, 72 kg) and $H_2O$ (43 kg) were charged into R2 to make 2N HCl aq. The 2N HCl aq was added from R2 to R1 slowly until the pH of the solution in R1 was below 3. R1 was stirred at 15~25° C. for 0.5~1.0 h. The slurry was filtered, and the cake was washed with $H_2O$ (10 kg). The cake was dried under vacuum at 60~70° C. and compound J was obtained as an off-white solid. $^1H$-NMR (300 MHz, DMSO-$d_6$): δ 13.48 (s, br, 1H), 12.86 (s, 1H), 7.12-7.21 (m, 2H).

Example 11. Preparation of Compound (l)

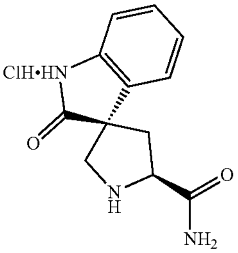

+

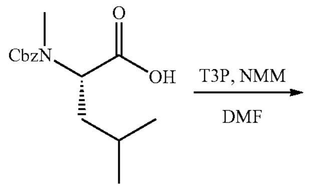

(f-1) (k)

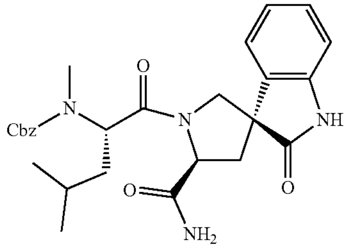

(I)

Under nitrogen atmosphere, DMF (480 kg, 5 V) was added to a reactor followed by Compound (f-1, 100 kg net weight, 1.0 eq) and Compound (k) (110 kg, 1.1 eq) around 20° C. The reactor was cooled to 0±5° C. NMM (113 kg, 3.0 eq.) was charged drop-wised into reaction system at 0±5° C. over 30 min. T3P in DMF (1.5 eq.) was charged dropwise into reaction system 0±5° C. over 1 h. The solution was stirred for at least 4 hours and reaction progress was monitor by HPLC. Once completion, the reaction mixture was charged drop-wised into 2% aq. $NaHCO_3$ (25.0 v) at 20±5° C. Then, stir for at least 2 hours. The mixture was filtered, the cake was washed with water. The filter cake was slurry with Process Water (2000 kg, 20 V) for 3 hours at 20° C. before it was filtered and washed with water. The cake was dried at 60±5° C. to give product of Compound (l) as off-white solid in 90-93% yield.

$^1H$ NMR (300 MHz, DMSO-$d_6$) δ 10.72 (d, J=6.6 Hz, 1H), 7.52 (s, 1H), 7.30 (q, J=4.5, 3.6 Hz, 2H), 7.26-7.17 (m, 2H), 7.14 (dd, J=7.1, 2.4 Hz, 1H), 7.06 (d, J=10.6 Hz, 1H), 7.01-6.85 (m, 3H), 6.80 (d, J=7.3 Hz, 1H), 4.86 (dd, J=15.5, 11.9 Hz, 2H), 4.68-4.50 (m, 2H), 3.95 (d, J=10.2 Hz, 1H), 3.73 (d, J=10.2 Hz, 1H), 2.80 (d, J=6.1 Hz, 3H), 2.33-2.11 (m, 2H), 1.63 (ddd, J=13.9, 9.5, 4.8 Hz, 1H), 1.56-1.35 (m, 2H), 0.87 (dd, J=14.5, 6.2 Hz, 6H).

Example 12. Preparation of Compound (m-1) as a Free N-Methyl Amine

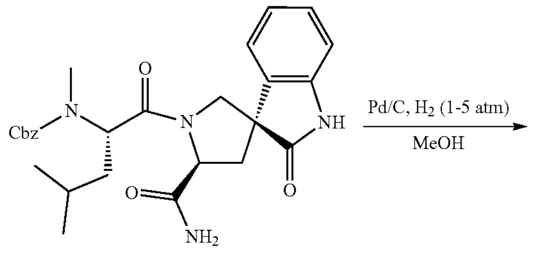

(I)

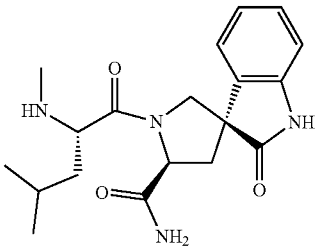

(m-1)

MeOH was charged (395.0 kg, 5 V) into reactor R1 under $N_2$ followed by Compound (I) (100 kg, 1.0 eq.). The reaction mixture was stirred for 30 min at 20° C. (15~25° C.) before Palladium on activated carbon (10 kg) was added into R1. R1 was rinsed with MeOH (79.0 kg, 1 V) under $N_2$ and cooled to 0° C. (−5~5° C.). The reaction mixture was stirred under $H_2$ (1-5 atm) for 8 h (5~12 h) at 0° C. (−5~5° C.). Once the reaction was completed, the mixture was filtered with celite (50.0 kg) and the filtrate was transferred into reactor R2 at −5-5° C. The filter cake was washed with MeOH (1 V×2) and the filtrate was combined. The solution in reactor R2 was concentrated to 2-3V below 12° C. under vacuum and cold THE (890.0 kg, 10 V) was added into reactor R2 at 0-10° C. The mixture was concentrated reactor R2 to 3-4 V below 12° C. under vacuum. Once precipitate was observed, cold THE (178 kg, 2 V) was added into reactor R2 at −5-5° C. followed by dropwise addition of n-Heptane (683.0 g, 10 V) into reactor R2 over 1 h (1~2 h).

The mixture in reactor R2 was stirred for 2 h (1~2 h) at 0° C. (−5~5° C.) and filtered. The cake was rinsed with n-heptane (136.6 kg, 2 V) and the wet cake was dried at 60° C. (55~65° C.) for 72 h to provide Compound (m-1) as a white solid in 80-85% yield. $^1H$ NMR (400 MHz, DMSO-$d_6$) δ 10.72 (s, 1H), 7.55-7.40 (m, 1H), 7.31-7.17 (m, 1H), 7.06-6.95 (m, 2H), 6.93 (dd, J=7.6, 2.0 Hz, 2H), 4.78-4.51 (m, 1H), 4.03 (d, J=10.3 Hz, 1H), 3.66 (d, J=10.2 Hz, 1H), 3.28 (dd, J=8.4, 5.6 Hz, 1H), 2.19 (d, J=9.0 Hz, 2H), 2.12 (d, J=5.6 Hz, 3H), 1.40-1.12 (m, 3H), 0.84 (dd, J=17.5, 6.6 Hz, 6H).

Example 13. Preparation of Compound (m-2)

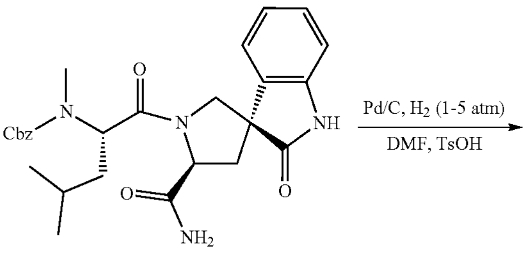

(I)

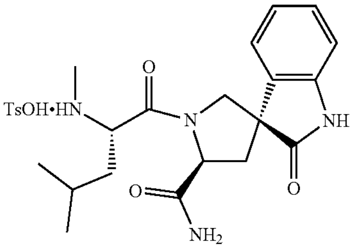

(m-2)

DMF was charged (39.5 kg, 5 V) into reactor R1 under $N_2$ followed by Compound (I) (10 kg, 1.0 eq.) and TsOH (1.0-1.1 eq). The reaction mixture was stirred for 30 min at 20° C. (15~25° C.) before Palladium on activated carbon (1 kg) was added into reactor R1. Reactor R1 was rinsed with DMF (7.9 kg, 1 V) under $N_2$ and cooled to 0° C. (−5~5° C.). The reaction mixture was stirred under $H_2$ (1-5 atms) for 8 h (5~12 h) at 0° C. (−5~5° C.). Once reaction was completed, the mixture was filtered with celite (5 kg) and the filtrate (m-2) can be carried to next step without purification.

Example 14. Preparation of Compound (m-3)

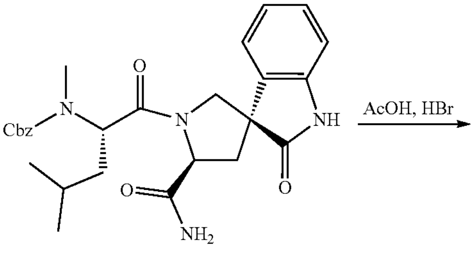

(I)

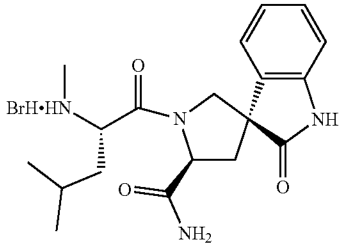

(m-3)

AcOH (10 L, 2.0 V) was charged to a reactor at 25° C. followed by Compound (I) (5 kg, 1.0 eq). HBr in AcOH (7.5 L, 1.5 V, 5.0 eq.) was charged dropwise into the reactor at 20-30° C. and the reaction mixture was stirred for at least 2 hours at 20-30° C. Once reaction was complete, the reaction solution was diluted with acetone (10 L, 2V) at 25° C. The resulting solution was then added dropwise into MTBE (100 L, 20 V) at 25° C. The slurry was stirred for at least 2 hours at 25° C. and then filtered. The cake was rinsed with MTBE (10 L, 2 V) and the cake was re-slurried with Acetone/DCM (1:10, 100 L, 20 V) three times at 25° C. The material was filtered, rinsed with DCM (10 L, 2 V), and the cake was dried at 40±5° C. to give product of Compound (m-3) as off-white solid with about 90% yield. $^{1}$H-NMR (300 MHz, Methanol-$d_4$) δ 7.31 (td, J=7.6, 1.4 Hz, 1H), 7.19-7.12 (m, 1H), 7.08 (td, J=7.5, 1.1 Hz, 1H), 7.02 (d, J=7.7 Hz, 1H), 5.01 (s, 1H), 4.33 (t, J=6.6 Hz, 1H), 4.11 (d, J=10.1 Hz, 1H), 3.91 (d, J=10.0 Hz, 1H), 2.68 (s, 3H), 2.49 (dd, J=8.8, 2.6 Hz, 2H), 2.01-1.79 (m, 2H), 1.30 (dd, J=4.7, 2.6 Hz, 1H), 1.03 (t, J=6.6 Hz, 6H).

Example 15. Preparation of Preparation of (3R,5'S)-1'-(N-methyl-N-(4,6,7-trifluoro-1H-indole-2-carbonyl)-L-leucyl)-2-oxospiro[indoline-3,3'-pyrrolidine]-5'-carboxamide (Compound (n))

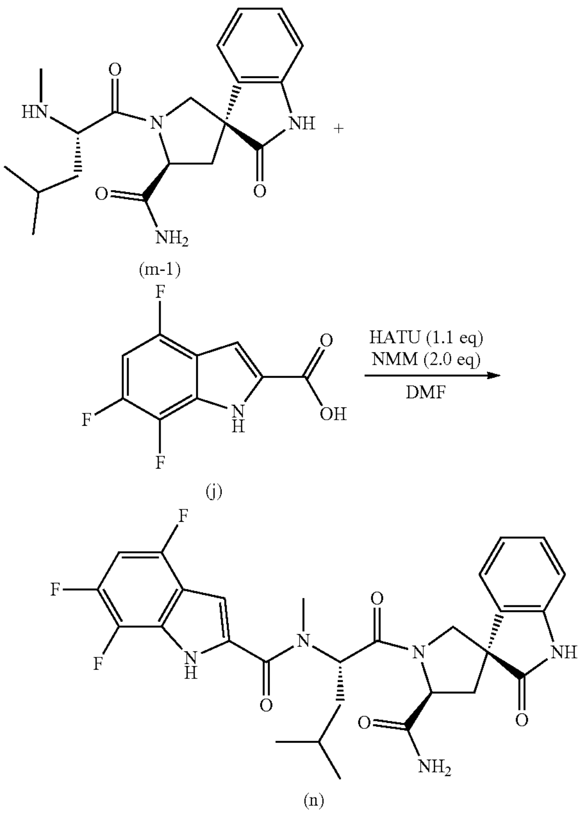

(m-1)

(j)

(n)

DMF (760 kg, 8V) was added into the reaction at 0° C. (−5~5° C.) followed by compound (j) (63 kg, 1.05 eq) and N-Methylmorpholine (56 kg, 2 eq), HATU (106 kg, 1.0 eq) and Compound (m-1) (100 kg, 1.0 eq). The reactor was rinsed with DMF (190 kg, 2V) under and warmed up to 25° C. (20-30° C.) and stirred for 5 h (3~6 h) at 25° C. (20~30° C.). After that, additional HATU (0.1 eq) was added and the reaction mixture was stirred for 16-24 h. 25% Ammonium hydroxide (38 kg) was added to the reaction mixture at 25° C. (20~30° C.) and stirred for 2 h (1~3 h) at 25° C. (20~30° C.). The reaction mixture was then added to water (5000 kg, 50V) at 20-30° C. over 2 h and the resulting slurry was stirred for 2 h (1~5 h) at 25° C. (20~30° C.). The mixture was filtered and the cake was rinsed with water (500 kg, 5 V). The cake was dissolved in ethyl acetate (1350 kg, 15 V) and washed with 10% sodium chloride solution (500 kg) for three times. The organic layer was separated to 1.5-2.5V at not more than 45° C. under vacuum. The solution was cooled to 25° C. (20~30° C.) and Dichloromethane (660 kg, 5V) was added. The mixture was stirred for 2 h (2~5 h) at 25° C. (20~30° C.) and a slurry was formed. n-Heptane (137 kg, 2V) was added dropwise over 0.5 h (0.5~2 h) at 25° C. (20~30° C.) and stirred for additional 2 h (1~3 h) at 25° C. (20~30° C.). The reaction mixture was filtered and the wet cake was rinsed with DCM/heptane (5/2). The wet cake was dried at 50° C. (45~55° C.) for 20 h (15~25 h) to provide Compound (n) as the white solid in 80~85% yield.

$^{1}$H NMR (300 MHz, DMSO-$d_6$) δ 12.46 (s, 1H), 10.68 (s, 1H), 7.56 (s, 1H), 7.15-7.00 (m, 3H), 6.91 (t, J=4.4 Hz, 2H), 6.84 (d, J=7.7 Hz, 1H), 6.55 (d, J=2.8 Hz, 1H), 5.34 (t, J=7.3 Hz, 1H), 4.63 (dd, J=9.8, 8.0 Hz, 1H), 3.83 (q, J=10.3 Hz, 2H), 3.45 (qd, J=7.0, 5.1 Hz, 1H), 3.16 (s, 3H), 2.35-2.13 (m, 2H), 1.69 (t, J=7.1 Hz, 2H), 1.56 (dq, J=13.1, 6.5 Hz, 1H), 0.93 (dd, J=12.2, 6.3 Hz, 6H).

Example 16. Preparation of (3R,5'S)-1'-(N-methyl-N-(4,6,7-trifluoro-1H-indole-2-carbonyl)-L-leucyl)-2-oxospiro[indoline-3,3'-pyrrolidine]-5'-carboxamide (Compound (n))

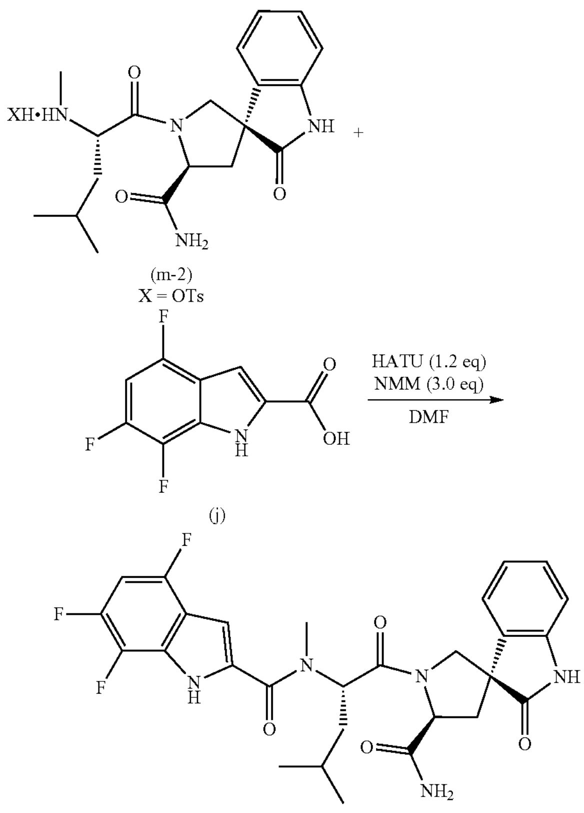

(m-2)
X = OTs (j)

(n)

DMF solution of Compound (m-2) (1 kg, 1.0 eq.) was added to a reactor at around 0-10° C. Compound (l) (600 g, 1.0 eq.), NMM (3.00 eq., 850 g) and HATU (1.00 eq., 1.06 kg) was added to the reactor while maintaining the temperature at 0~10° C.; The reaction was warmed to 20±5° C., and stirred for at least 6 hours at 20±5° C. HATU (0.20 eq., 210 g) was added to the reactor at 20±5° C. and stirred for at least 6 hours at 20±5° C. 25% Ammonium hydroxide (390 g, 1.0 eq) was added to the reaction mixture at 20° C. and stirred for 2 h (1~3 h) at 20° C. EtOAc (14.0 V) and water (14 V) was added at around 25° C. over 20 minutes, and the solution was stirred for at least 30 min. Aqueous phase was extracted with EtOAc for three times and the organic phase was combined, and washed with 10% aq. NaCl for three times at 20±5° C. The organic phase was concentrated to 6 V then EtOH (7.0 V) was charged. The EtOAc-EtOH solvent swap was repeated for three times and concentrated to 5 V before water (7.0 v) was added at 20±5° C. The mixture was cooled to 0~10° C. and stirred for 1 h before being filtered. The filter cake was dissolved in ethyl acetate (15 V) and washed with 10% sodium chloride solution for three times. The organic layer was concentrated to 2-3V at not more than 45° C. under vacuum. The solution was cooled to 25° C. (20~30° C.) and Dichloromethane (5V) was added. The mixture was stirred for 2 h (2~5 h) at 25° C. (20~30° C.) and a slurry was formed. n-Heptane (2V) was added dropwise over 0.5 h (0.5~2 h) at 25° C. (20~30° C.) and stirred for additional 2 h (1~3 h) at 25° C. (20~30° C.). The reaction mixture was filtered and wet cake was rinsed with DCM/heptane (5/2). The wet cake was dried at 50° C. (45~55° C.) for 20 h (15~25 h) to provide Compound (n) as the white solid in about 70-75% yield over two steps.

$^1$H NMR (300 MHz, DMSO-$d_6$) δ 12.46 (s, 1H), 10.68 (s, 1H), 7.56 (s, 1H), 7.15-7.00 (m, 3H), 6.91 (t, J=4.4 Hz, 2H), 6.84 (d, J=7.7 Hz, 1H), 6.55 (d, J=2.8 Hz, 1H), 5.34 (t, J=7.3 Hz, 1H), 4.63 (dd, J=9.8, 8.0 Hz, 1H), 3.83 (q, J=10.3 Hz, 2H), 3.45 (qd, J=7.0, 5.1 Hz, 1H), 3.16 (s, 3H), 2.35-2.13 (m, 2H), 1.69 (t, J=7.1 Hz, 2H), 1.56 (dq, J=13.1, 6.5 Hz, 1H), 0.93 (dd, J=12.2, 6.3 Hz, 6H).

Example 17. Preparation of (3R,5'S)-1'-(N-methyl-N-(4,6,7-trifluoro-1H-indole-2-carbonyl)-L-leucyl)-2-oxospiro[indoline-3,3'-pyrrolidine]-5'-carboxamide (Compound (n))

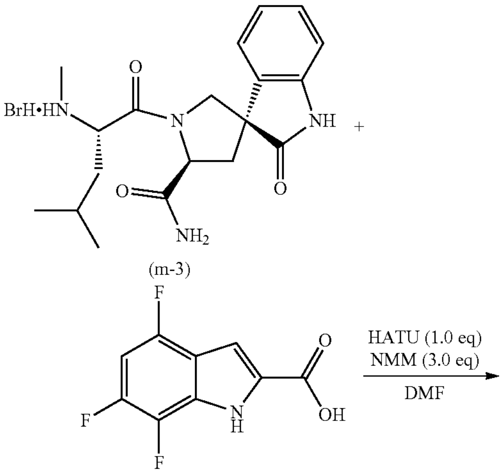

(m-3)

(j)

-continued

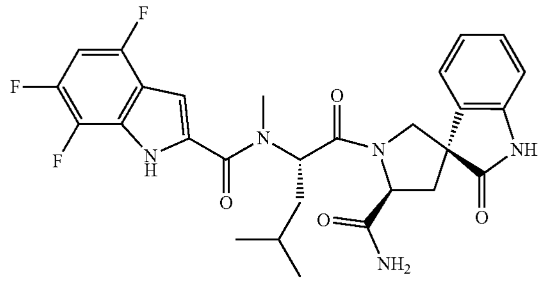

(n)

DMF (10.0 v) was added to a reactor at 25° C. followed by Compound (l) (4.4 kg, 1.0 eq.), NMM (3.0 eq.) Compound (m-3) (1.0 eq.) and HATU (1.0 eq) at 20-25° C. The reaction mixture was stirred for at least 12 hours at 20-25° C. Once reaction was complete, aqueous ammonium hydroxide (1.0 eq.) was to the reaction system at 20-25° C., then stirred for at least 2 hours at 20-25° C. The reaction mixture was then added to water (220 kg, 50V) at 20-30° C. over 2 h and the resulting slurry was stirred for 2 h (1~5 h) at 25° C. (20~30° C.). The mixture was filtered and the cake was rinsed with water (22 kg, 5 V). The cake was dissolved in ethyl acetate (135 g, 15 V) and washed with 100% sodium chloride solution (22 kg) for three times. The organic layer was separated to 1.5-2.5V at not more than 45° C. under vacuum. The solution was cooled to 25° C. (20~0.30° C.) and Dichloromethane (5V) was added. The mixture was stirred for 2 h (2~5 h) at 25° C. (20~30° C.) and a slurry was formed. n-Heptane (2V) was added dropwise over 0.5 h (0.5~2 h) at 25° C. (20~30° C.) and stirred for additional 2 h (1~3 h) at 25° C. (20~30° C.). The reaction mixture was filtered and wet cake was rinsed with DCM/heptane (5/2). The wet cake was dried at 50° C. (45~55° C.) for 20 h (15~25 h) to provide Compound (n) as the white solid in 80-85% yield. $^1$H NMR (300 MHz, DMSO-d6) δ 12.46 (s, 1H), 10.68 (s, 1H), 7.56 (s, 1H), 7.15-7.00 (m, 3H), 6.91 (t, J=4.4 Hz, 2H), 6.84 (d, J=7.7 Hz, 1H), 6.55 (d, J=2.8 Hz, 1H), 5.34 (t, J=7.3 Hz, 1H), 4.63 (dd, J=9.8, 8.0 Hz, 1H), 3.83 (q, J=10.3 Hz, 2H), 3.45 (qd, J=7.0, 5.1 Hz, 1H), 3.16 (s, 3H), 2.35-2.13 (m, 2H), 1.69 (t, J=7.1 Hz, 2H), 1.56 (dq, J=13.1, 6.5 Hz, 1H), 0.93 (dd, J=12.2, 6.3 Hz, 6H).

Example 18. Preparation of N—((S)-1-((3R,5'S)-5'-cyano-2-oxospiro[indoline-3,3'-pyrrolidin]-1'-yl)-4-methyl-1-oxopentan-2-yl)-4,6,7-trifluoro-N-methyl-1H-indole-2-carboxamide Toluene Solvate (Compound (I))

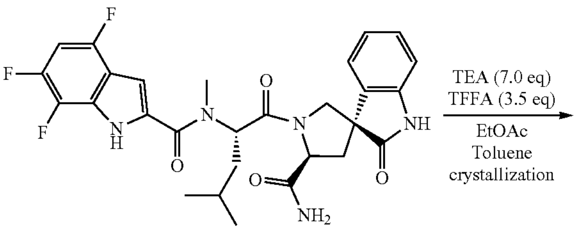

(n)

-continued

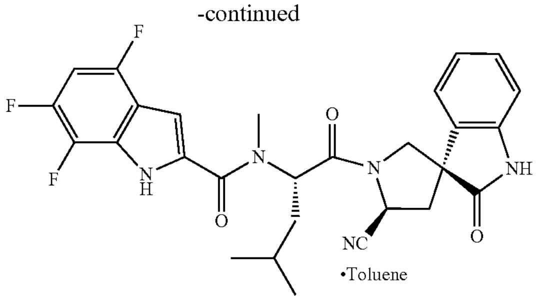

(I)

Ethyl acetate (630 kg, 10 V) was added into reactor (R1) followed by Compound (n) (70 kg). Make sure the water content was less than 0.20% (w/w). The reaction was cooled to 0° C. (−5~5° C.) and then triethylamine (89.6 kg) was added followed by trifluoroacetic anhydride (92.4 kg) at 0° C. (−5~5° C.). The reaction was stirred for 1 h (0.5~2 h) at 0° C. (−5~5° C.). Once the reaction was complete, the reaction mixture was added slowly to 0.2 N aqueous HCl solution (700 kg) over 1 h at 0° C. (−5~5° C.). The resulting solution was stirred for 30 min at 0° C. (−5~5° C.) and the organic layer was separated. 1% aqueous ammonium hydroxide (700 kg) was added to the organic layer and stirred at 20° C. for 30 min (15~25° C.). The organic layer was separated and washed with 10% brine for four times. Then the organic layer was separated and distilled to 2-3 V. Toluene-EtOAc swap was performed until precipitate was observed at 3-4 V. Then Toluene (5-6 V) was added and the slurry was stirred at 50° C. for 2 h. Then the solution was cooled down to 20° C. over 1-2 h and stirred for 10 hr (6~14 hr) at 20° C. (15~25° C.). The reaction mixture was filtered and the wet cake was rinsed with toluene (120 kg, 2V). The wet cake was then dried at 50° C. (45~55° C.) for 48 hr to provide desired compound (o) as a white solid in 80-85% yield.

$^1$H NMR (400 MHz, Acetone-d6) δ 11.17 (s, 1H), 9.65 (s, 1H), 7.02 (dd, J=13.7, 7.3 Hz, 2H), 6.94 (dd, J=6.0, 3.5 Hz, 1H), 6.92-6.85 (m, 2H), 6.81 (t, J=7.5 Hz, 1H), 5.56 (dd, J=9.4, 5.6 Hz, 1H), 5.21 (t, J=8.3 Hz, 1H), 4.25 (d, J=10.7 Hz, 1H), 3.99 (d, J=10.6 Hz, 1H), 3.43 (s, 3H), 2.79-2.61 (m, 2H), 1.93 (ddd, J=14.4, 9.5, 5.1 Hz, 1H), 1.79 (ddd, J=14.2, 8.7, 5.6 Hz, 1H), 1.64 (dpd, J=8.7, 6.6, 5.1 Hz, 1H), 0.98 (dd, J=18.5, 6.6 Hz, 6H).

Example 19. Preparation of N—((S)-1-((3R,5'S)-5'-cyano-2-oxospiro[indoline-3,3'-pyrrolidin]-1'-yl)-4-methyl-1-oxopentan-2-yl)-4,6,7-trifluoro-N-methyl-1H-indole-2-carboxamide—Amorphous Form (Compound (I))

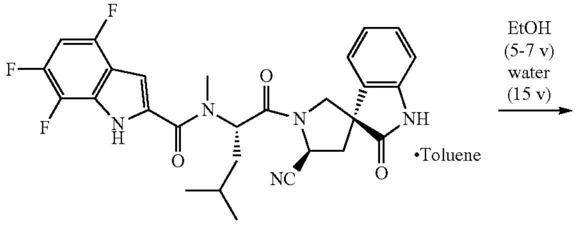

(I)

-continued

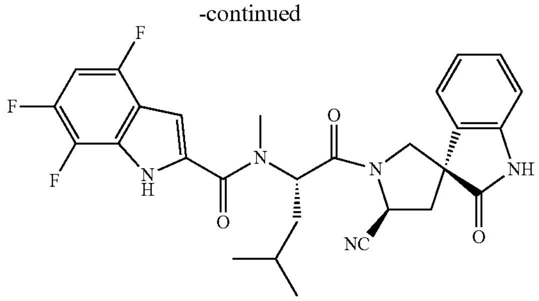

Compound (I)
Amorphous

Toluene solvate compound (I) (60 kg, net weight) and ethanol (10 Volumes (V)) were added to the reactor at 20-30° C. The mixture was stirred at 20-30° C. for 0.5-1 hour to obtain a clear solution. The solution was distilled to ~5 V at temperature (NMT 50° C.) and refilled with ethanol (5 V). The distillation was repeated until residual toluene level was ≤0.1% w/w. The compound in EtOH solution (5-6 V) was added to water (15 V) over 1-2 h at 20° C. (15~25° C.) and stirred at 15-25° C. for 1 h (0.5-2 hours). The slurry was filtered and the wet cake was rinsed with purified water (2 V). The wet cake was then dried at 50° C. (45-55° C.) for 48-72 hours to afford Compound (I) as a white to off-white amorphous solid in 95-97% yield.

$^1$H NMR (400 MHz, Acetone-$d_6$) δ 11.17 (s, 1H), 9.65 (s, 1H), 7.02 (dd, J=13.7, 7.3 Hz, 2H), 6.94 (dd, J=6.0, 3.5 Hz, 1H), 6.92-6.85 (m, 2H), 6.81 (t, J=7.5 Hz, 1H), 5.56 (dd, J=9.4, 5.6 Hz, 1H), 5.21 (t, J=8.3 Hz, 1H), 4.25 (d, J=10.7 Hz, 1H), 3.99 (d, J=10.6 Hz, 1H), 3.43 (s, 3H), 2.79-2.61 (m, 2H), 1.93 (ddd, J=14.4, 9.5, 5.1 Hz, 1H), 1.79 (ddd, J=14.2, 8.7, 5.6 Hz, 1H), 1.64 (dpd, J=8.7, 6.6, 5.1 Hz, 1H), 0.98 (dd, J=18.5, 6.6 Hz, 6H).

Figure 2:
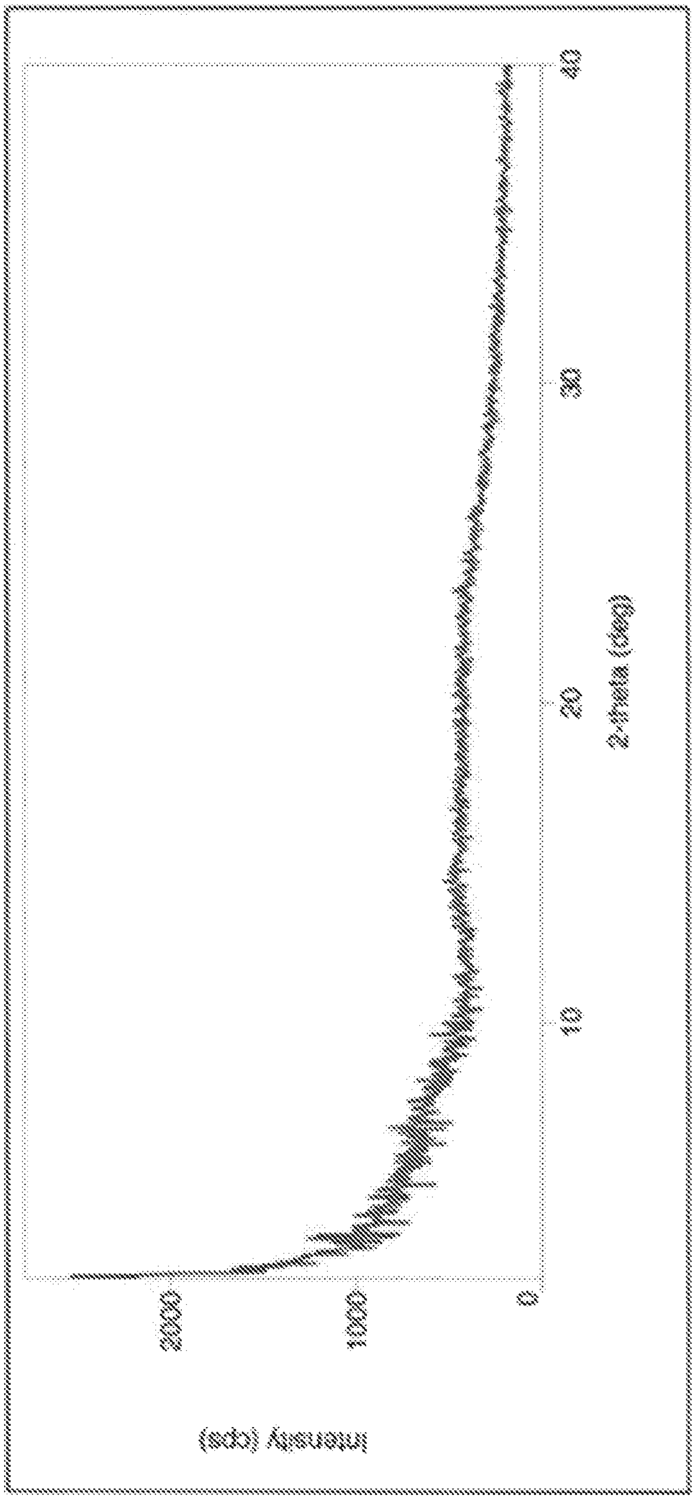
FIG. 2 is the X-ray powder diffractogram of the amorphous form of Compound 1 produced in Example 19.
Figure 3:
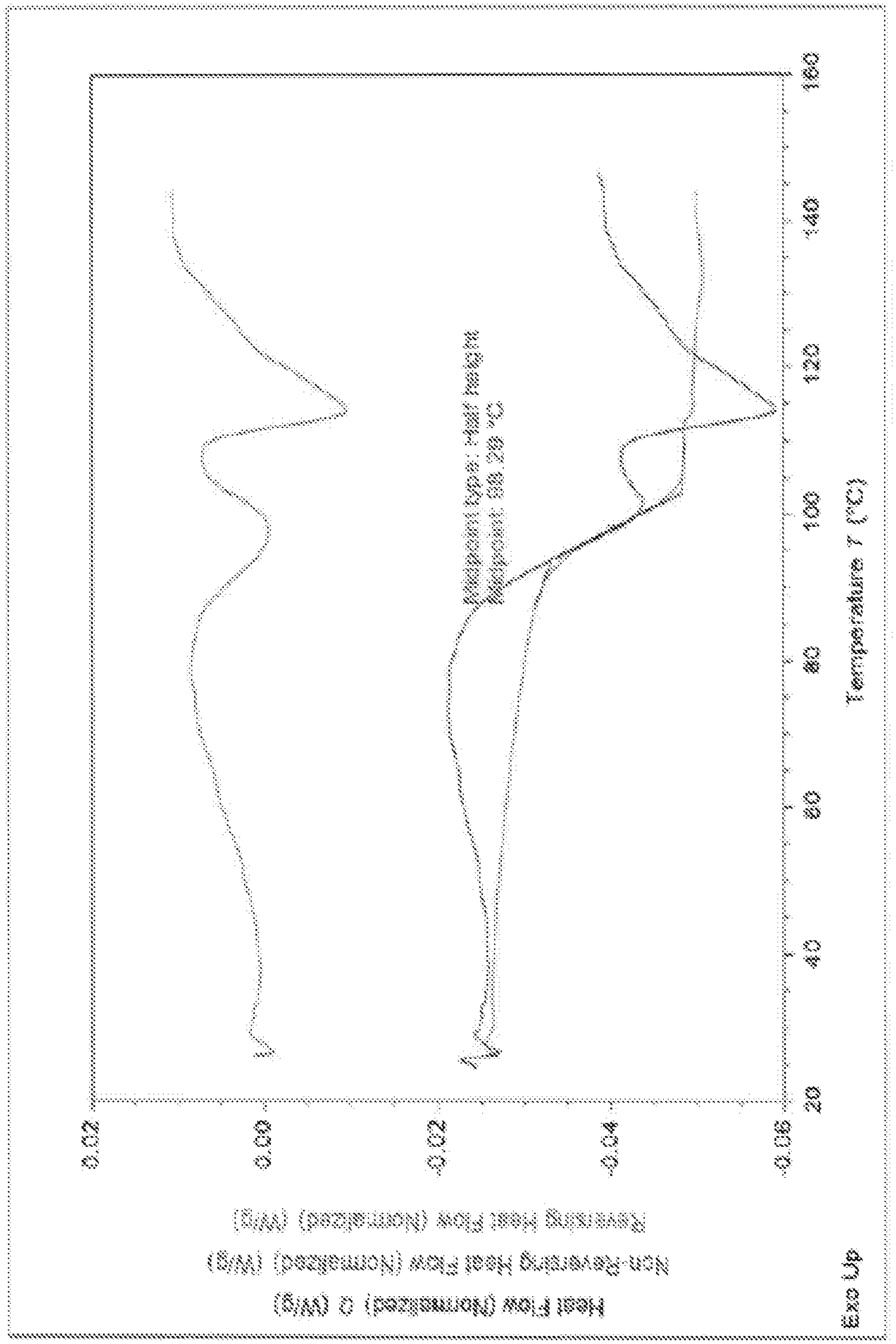
FIG. 3 is the DSC thermogram of the amorphous form of Compound 1 produced in Example 19.

Powder X-ray Diffraction (PXRD) analysis and Differential Scanning Calorimetry (DSC) analysis were used to perform the physical characterization for the said amorphous form of Compound (I). The X-ray diffractogram is shown in FIG. 2 and indicated the compound (I) is amorphous. The DSC thermogram is shown in FIG. 3 and indicated a glass transition with midpoint at 98.29° C.

Example 20. Preparation of Sodium hydroxy(2,4,5-trifluorophenyl)methanesulfonate (g-c)

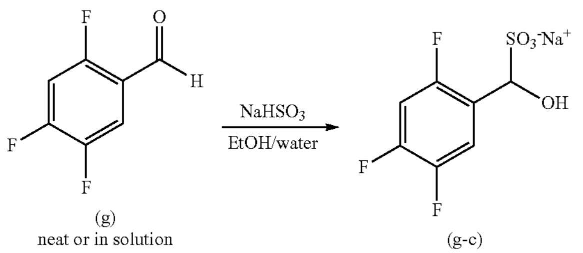

(g)
neat or in solution (g-c)

Method A: 2,4,5-trifluorobenzaldehyde (100 g neat, obtained by distillation in experiment 7) was added into reactor R1 followed by the addition of MTBE (500 mL) and EtOH (600 mL). $NaHSO_3$ (71.5 g) and water (100 g) was added into reactor R2. The mixture in R2 was heated to 40° C. and stirred for 20 minutes to form a clear solution. The solution in R1 was heated to 40° C. The solution of R2 was transferred to R1 over 1 hour and the resulting mixture in R1 was stirred for another 2 hours at 40° C. The mixture in R1 was cooled to 20° C. over 1 hour and stirred for another 1 hour at 20° C. Filter and wash the wet cake with ethanol (80 g). The cake was dried at 50° C. to provide compound (g-c) as a white solid.

Method B: 100 g of 2,4,5-trifluorobenzaldehyde in MTBE solution (100 mL) prepared from the procedure in Example 7 was added into reactor R1 followed by the addition of MTBE (400 mL) and EtOH (600 mL). $NaHSO_3$ (71.5 g) and water (100 g) was added into reactor R2. The mixture in R2 was heated to 40° C. and stirred for 20 minutes to form a clear solution. The solution in R1 was heated to 40° C. The solution of R2 was transferred to R1 over 1 hour and the resulting mixture in R1 was stirred for another 2 hours at 40° C. The mixture in R1 was cooled to 20° C. over 1 hour and stirred for another 1 hour at 20° C. Filter and wash the wet cake with ethanol (80 g). The cake was dried at 50° C. to provide compound (g-c) as a white solid.

Example 21. Preparation of Compound g from Sodium hydroxy(2,4,5-trifluorophenyl)methanesulfonate (g-c)

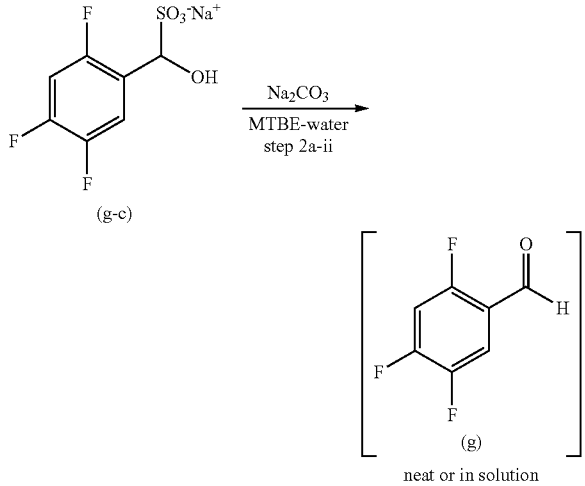

(g-c) (g)

Compound g-c (100 g) and methyl-tert-butylether (MTBE, 400 mL) was added into reactor R1 following by the addition of water (500 mL) and sodium carbonate (48 g). The mixture in R1 was stirred at 25° C. for 2 hours to form a biphasic solution. The upper layer (organic layer) was separated and remove the bottom layer (aqueous layer). The aqueous layer was extracted with MTEB and the organic layer was combined. The combined organic layer can be treated by two following methods to obtain compound (g).

Method A: The organic layer was concentrated to no obvious distillate out below 30° C. Crude compound (g) was obtained as orange oil and transferred to distillation reactor R3. R3 was distilled until there was no obvious distillate out below 30° C. under vacuum≤0.085 MPa, and then R3 was distilled at 60~100° C. (recommend 70~80° C.) under vacuum≥0.090 MPa, and the distillate was collected. The purified compound (g) was obtained as colorless to orange oil. (same procedure in Example 7)

Method B: Methanol was added to the organic layer. After solvent exchange from MTBE to Methanol, compound (g) in methanol solution can be used in the next condensation reaction to form compound (h), see experiment 8.

While this invention has been particularly shown and described with references to preferred embodiments thereof, it will be understood by those skilled in the art that various changes in form and details may be made therein without departing from the scope of the invention encompassed by the appended claims.

What is claimed is:

1. A process for producing a compound of Formula (A), (A)

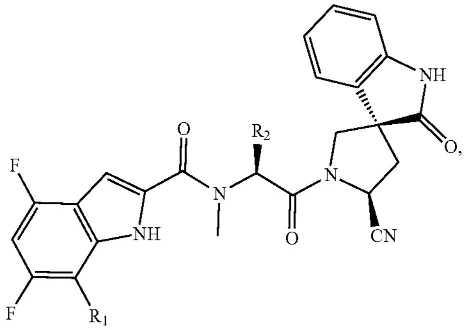

wherein $R_1$ is selected from the group consisting of hydrogen, Cl, F, optionally substituted methyl, and optionally substituted methoxy; and $R_2$ is selected from the group consisting of hydrogen, optionally substituted-$C_1$-$C_6$ alkyl, and optionally substituted-$C_1$-$C_6$ alkylaryl, said process comprising the steps of a) reacting a compound of Formula (W) with formaldehyde, to produce a compound of Formula (B):

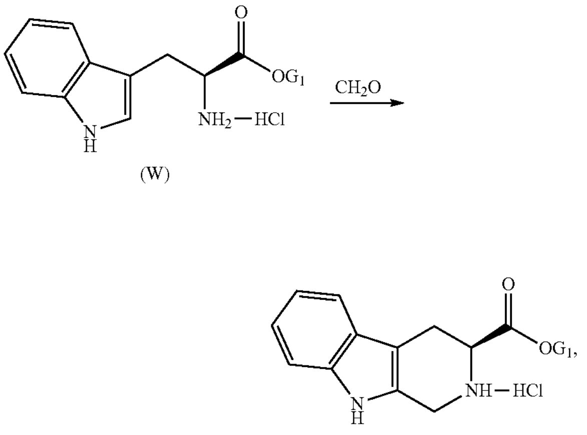

(W) (B)

wherein $G_1$ is methyl, ethyl or phenyl;

b) converting the compound of Formula (B) to a compound of Formula (C):

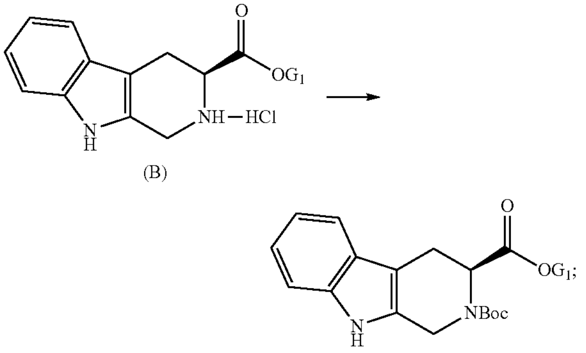

(B)

(C)

c) subjecting the compound of Formula (C) to rearrangement to produce a compound of Formula (D-1):

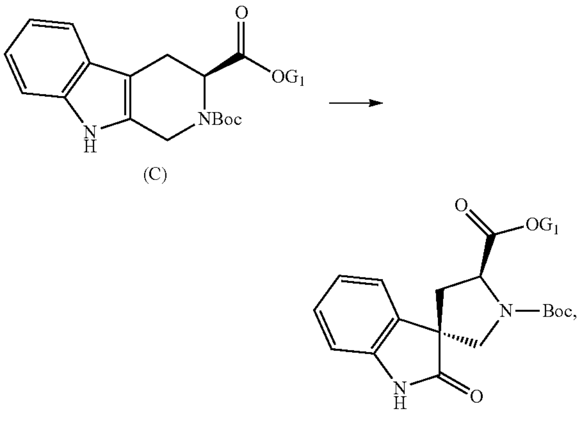

(C)

(D-1)

d) converting the compound of Formula (D-1) to a compound (e-1):

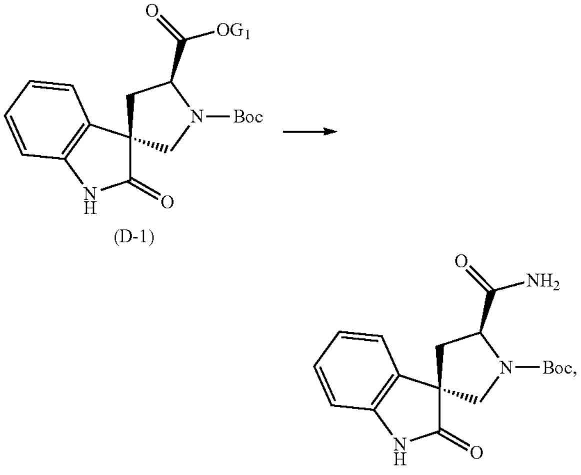

(D-1)

(e-1)

e) converting the compound (e-1) to a compound of Formula (F-1):

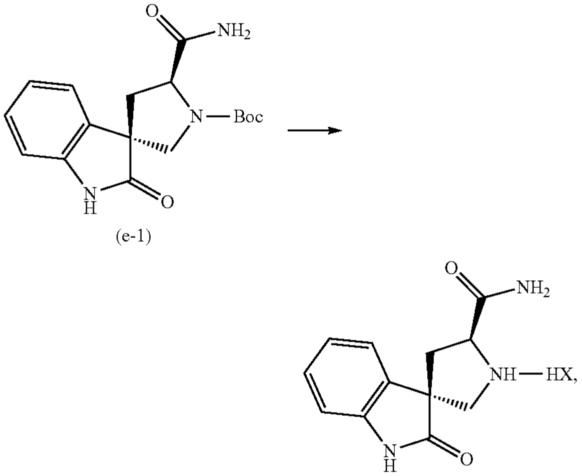

(e-1)

(F-1)

wherein X is an anion selected from the group consisting of $Cl^-$, $Br^-$, and $CF_3CO_2^-$;

f) reacting the compound of Formula (F-1) with a compound of Formula (K)

(K)

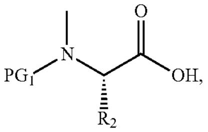

wherein $PG_1$ is selected from the group consisting of -Boc, -Cbz, —C(O) OMe, —C(O)OEt, -Fmoc, -Troc, -Moz, -Pnz, and -Teoc, to produce a compound of Formula (L):

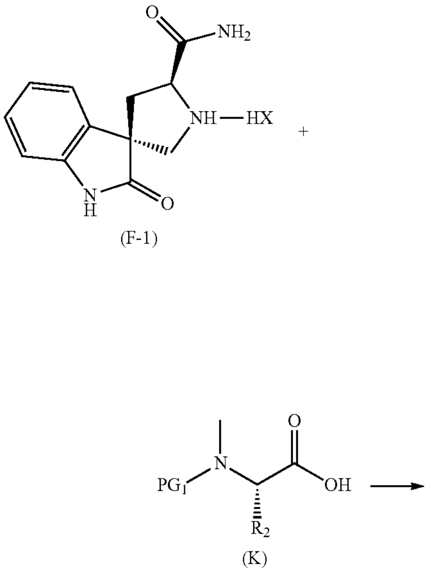

(F-1)

(K)

-continued

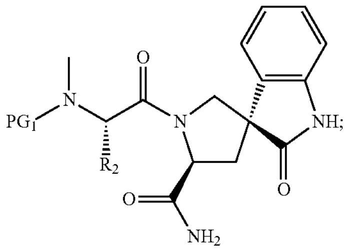

(L)

g) converting the compound of Formula (L), optionally in the presence of a suitable acid, to a compound of Formula (M) or a salt thereof:

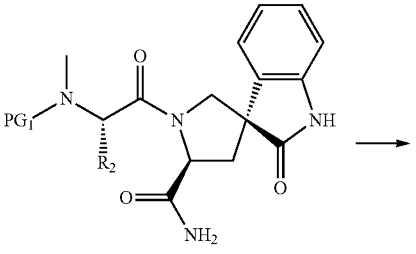

(L)

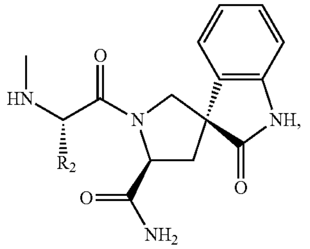

(M)

(J-1) reducing a compound of Formula (G-a) to produce a compound of Formula (G-b):

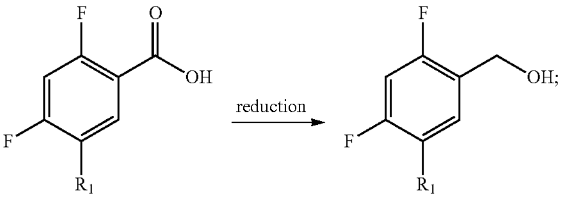

(G-a) (G-b)

(J-2) oxidizing the compound of Formula (G-b) to produce a compound of Formula (G):

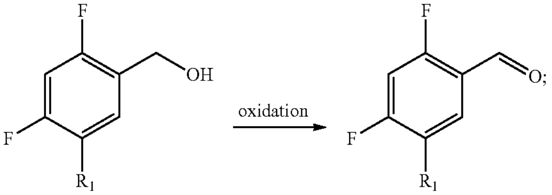

(G-b) (G)

(J-3) reacting the compound of Formula (G) with a compound of Formula (G-1), in the presence of a base to produce a compound of Formula (H):

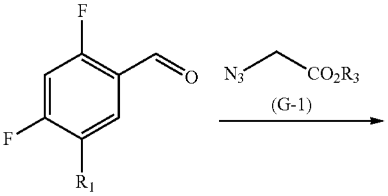

(G) (G-1)

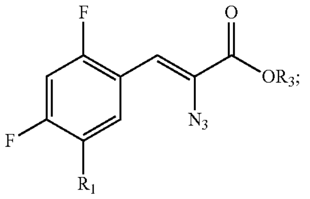

(H)

wherein $R_3$ is methyl, ethyl, or benzyl;

(J-4) converting the compound of Formula (H) to a compound of Formula (I) via Hemetsberger indole cyclization:

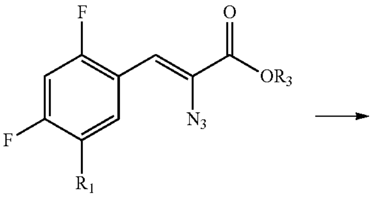

(H)

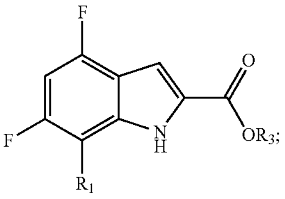

(I)

(J-5) reacting the compound (I) with a base to yield a compound of Formula (J):

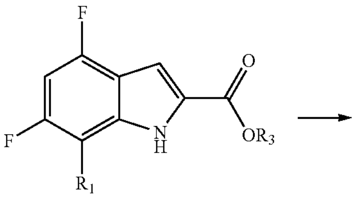

(I)

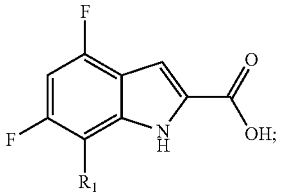

(J)

h) reacting the compound of Formula (M) or salt thereof with compound of Formula (J)

(J)

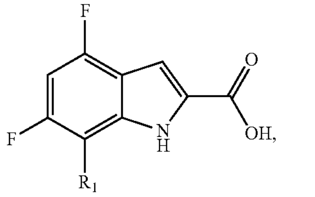

wherein $R_1$ is as previously defined; to provide a compound of Formula (N):

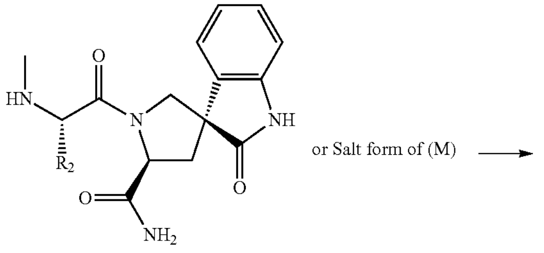

or Salt form of (M)

(M)

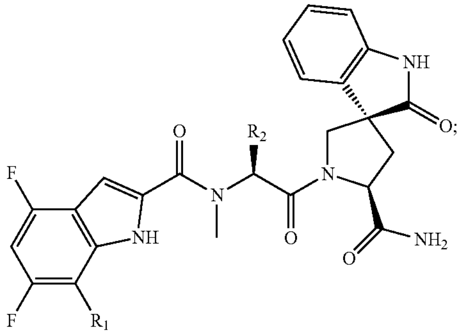

and (N)

i) converting the compound of Formula (N) to the compound of Formula (A):

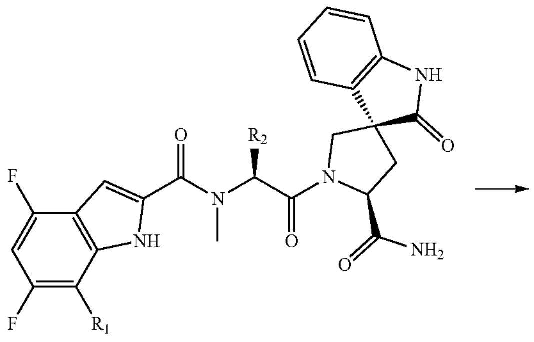

(N)

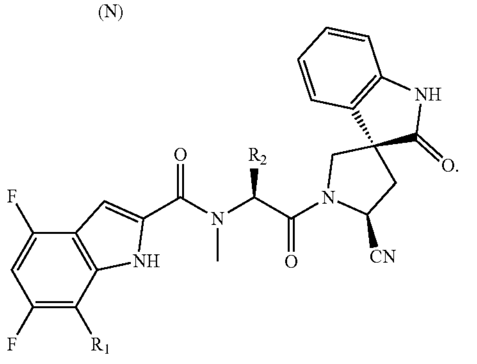

(A)

2. The process of claim 1, wherein $R_1$ is F and $R_2$ is isobutyl.

3. The process of claim 2, wherein $G_1$ is methyl, X is $Cl^-$ and $PG_1$ is Cbz.

4. The process of claim 1, wherein in step (b), the reaction is conducted in the presence of di-tert-butyl dicarbonate (Boc anhydride) as a Boc protection reagent and triethylamine as a base;

in step (c), the reaction is conducted in the presence of N-bromosuccinimide (NBS), acetic acid, at a temperature about −30° C.;

in step (d), the reaction is conducted in the presence of ammonia in methanol;

in step (e), the reaction is conducted in the presence of hydrogen chloride in ethyl acetate, and Compound (F-1) wherein X is chloride is separated by crystallization in N,N-dimethylformamide (DMF);

in step (f), the reaction is conducted in the presence of n-propanephosphonic acid anhydride (T3P) and N-methylmorpholine;

in step (g), $PG_1$ is Cbz, and the reaction is conducted in the presence of $H_2$ as hydrogen source, palladium on carbon as catalyst, and optionally conducted in the presence of p-toluenesulfonic acid; alternatively, in step (g), the reaction is conducted in the presence of hydrogen bromide in acetic acid;

in step (J-1), the reducing agent is sodium borohydride and borane-tetrahydrofuran complex;

in step (J-2), the oxidizing agent is sodium hypochlorite with TEMPO;

in step (J-3), $R_3$ is ethyl, and the reaction is conducted in the presence of sodium methoxide or sodium ethoxide as a base, and $CF_3CO_2Et$ as a sacrificial electrophile;

in step (J-4), the reaction is conducted in a flow chemistry reactor in solvent mixture of xylene and methanol, the volume ratio of xylene to methanol is 5:1 at about 200° C. as reaction temperature and under about 25 minutes as reaction time;

in step (J-5), the reaction is conducted in the presence of sodium hydroxide and followed by treatment with hydrogen chloride;

in step (h), the reaction is conducted in the presence of N-[(dimethylamino)-1H-1,2,3-triazolo[4,5-b]pyridin-1-ylmethylene]-N-methylmethanaminium hexafluorophosphate N-oxide (HATU), and N-methylmorpholine; and in step (i), the reaction is conducted in the presence of trifluoroacetic anhydride (TFAA), and triethylamine.

5. A process for producing a compound of Formula (A), (A)

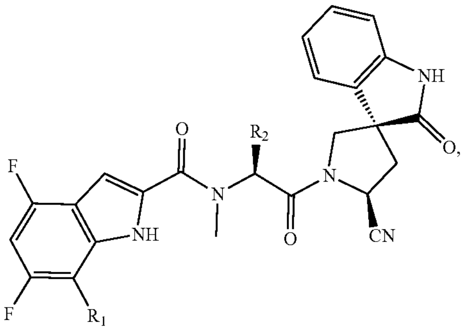

wherein $R_1$ is selected from the group consisting of hydrogen, Cl, F, optionally substituted methyl, and optionally substituted methoxy; and $R_2$ is selected from the group consisting of hydrogen, optionally substituted-$C_1$-$C_6$ alkyl, and optionally substituted-$C_1$-$C_6$ alkylaryl, said process comprising the steps of, a) reacting a compound of Formula (W), with formaldehyde, to produce a compound of Formula (B):

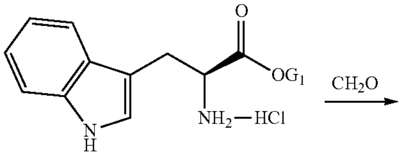

(W)

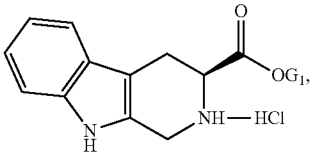

(B)

wherein $G_1$ is methyl, ethyl or phenyl;

b) converting the compound of Formula (B) to a compound of Formula (C):

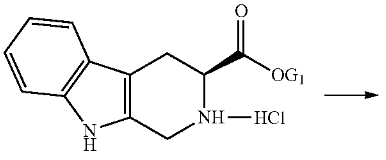

(B)

-continued

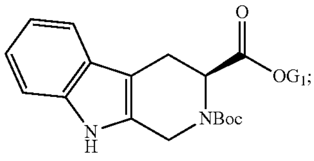

(C)

c) subjecting the compound of Formula (C) to rearrangement to produce a compound of Formula (D-1):

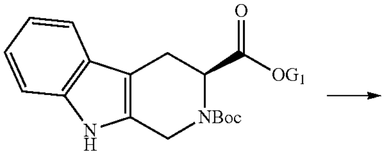

(C)

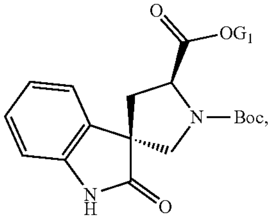

(D-1)

d) converting the compound of Formula (D-1) to a compound (e-1):

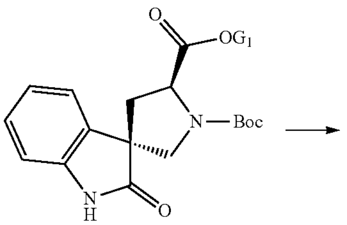

(D-1)

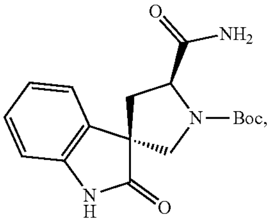

(e-1)

e) converting the compound (e-1) to a compound of Formula (F-1):

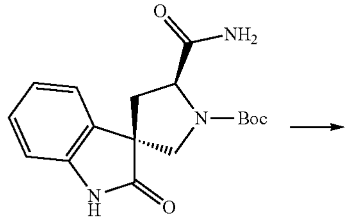

(e-1)

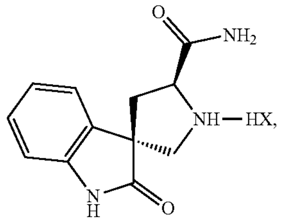

(F-1)

wherein X is an anion, selected from the group consisting of $Cl^-$, $Br^-$, and $CF_3CO_2^-$;

f) reacting the compound of Formula (F-1) with a compound of Formula (K):

(K)

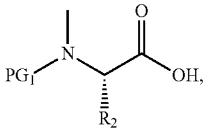

wherein $PG_1$ is selected from the group consisting of -Boc, -Cbz, —C(O) OMe, —C(O) OEt, -Fmoc, -Troc, -Moz, -Pnz, and -Teoc, to produce Compound of Formula (L):

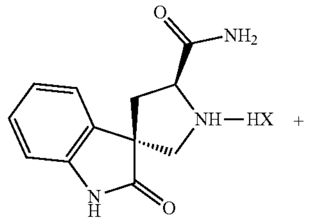

(F-1)

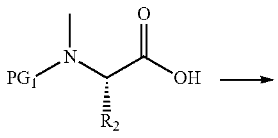

(K)

-continued

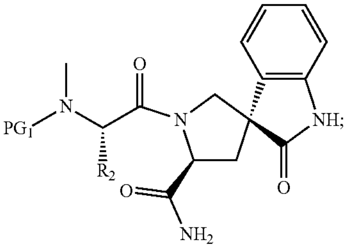

(L)

g) converting the compound of Formula (L), optionally in the presence of a suitable acid, to a compound of Formula (M) or a salt thereof:

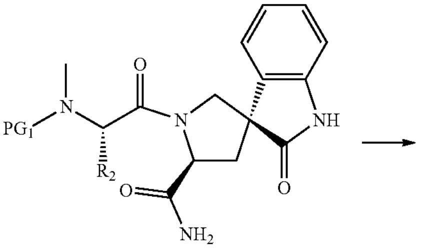

(L)

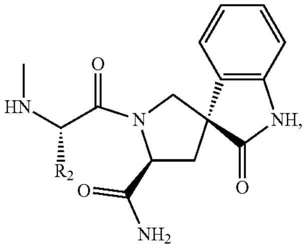

(M)

h) reacting the compound of Formula (M) or salt thereof with compound of Formula (J)

(J)

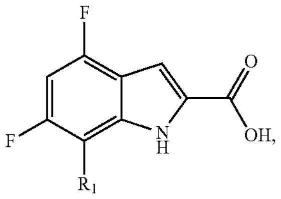

wherein $R_1$ is as previously defined; to provide a compound of Formula (N):

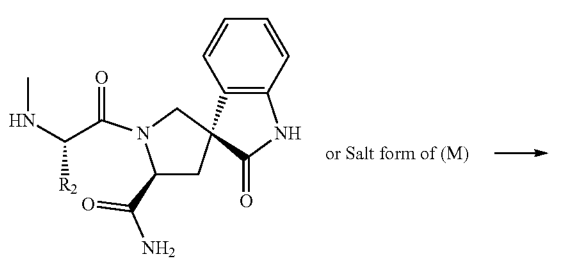

(M)

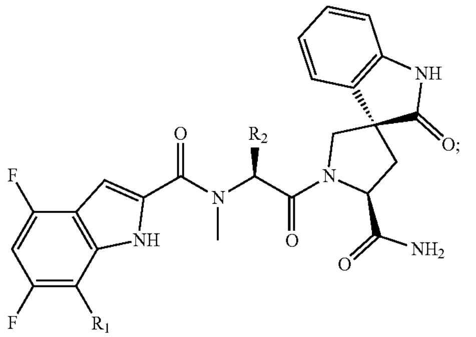

(N)

i) converting the compound of Formula (N) to the compound of Formula (A):

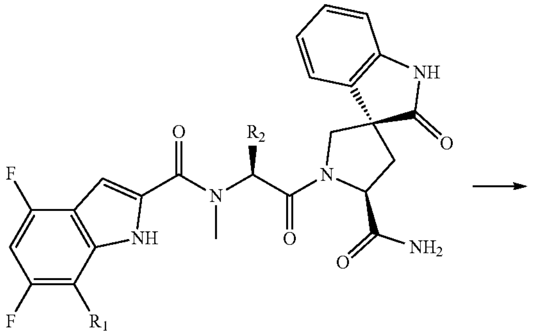

(N)

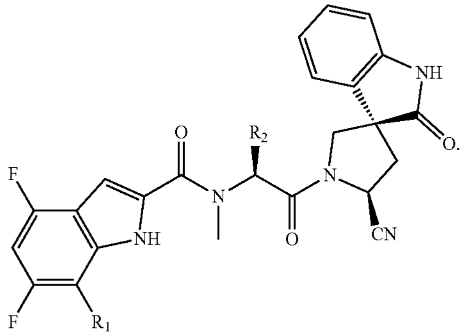

(A)

6. The process of claim 5, wherein $R_1$ is F and $R_2$ is isobutyl.

7. The process of claim 6, wherein $G_1$ is methyl, X is $Cl^-$ and $PG_1$ is Cbz.

8. The process of claim 5, wherein

In step (b), the reaction is conducted in the presence of di-tert-butyl dicarbonate (Boc anhydride) as a Boc protection reagent and triethylamine as a base;

In step (c), the reaction is conducted in the presence of N-bromosuccinimide (NBS), acetic acid, at a temperature about −30° C.;

In step (d), the reaction is conducted in the presence of ammonia in methanol;

In step (e), the reaction is conducted in the presence of hydrogen chloride in ethyl acetate, and Compound (F-1), wherein X is chloride, is separated by crystallization in N,N-dimethylformamide (DMF);

In step (f), the reaction is conducted in the presence of n-propanephosphonic acid anhydride (T3P) and N-methylmorpholine;

In step (g), $PG_1$ is Cbz, and the reaction is conducted in the presence of $H_2$ as hydrogen source, palladium on carbon as catalyst, and optionally conducted in the presence of p-toluenesulfonic acid; alternatively, in step (g), the reaction is conducted in the presence of hydrogen bromide in acetic acid;

In step (h), the reaction is conducted in the presence of N-[(dimethylamino)-1H-1,2,3-triazolo[4,5-b]pyridin-1-ylmethylene]-N-methylmethanaminium hexafluorophosphate N-oxide (HATU) and N-methylmorpholine; and In step (i), the reaction is conducted in the presence of trifluoroacetic anhydride (TFAA) and triethylamine.

9. A process for preparing a compound of Formula (A), (A)

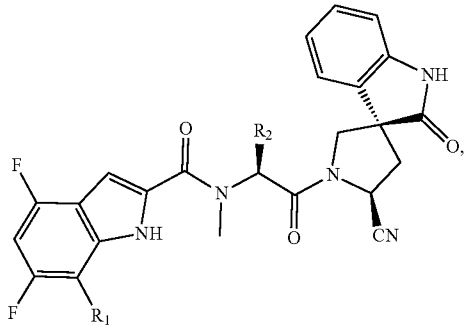

wherein $R_1$ is selected from the group consisting of hydrogen, Cl, F, optionally substituted methyl, and optionally substituted methoxy; and $R_2$ is selected from the group consisting of hydrogen, optionally substituted —$C_1$-$C_6$ alkyl, and optionally substituted —$C_1$-$C_6$ alkylaryl, said process comprising the steps of (a) reacting a compound of Formula (W) with formaldehyde, to produce a compound of Formula (B):

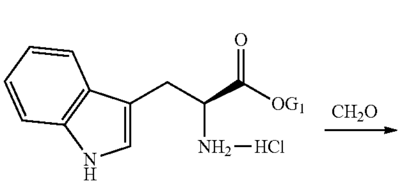

(W)

-continued

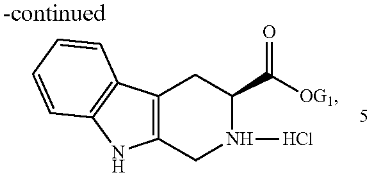

(B)

wherein $G_1$ is $C_1$-$C_6$-alkyl or aryl;

(b) converting the compound of Formula (B) to a compound of Formula (C):

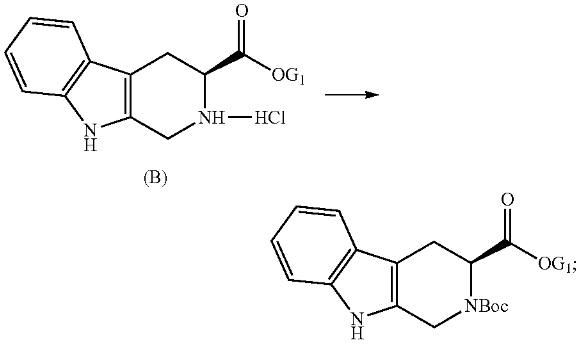

(B)

(C)

(c) subjecting the compound of Formula (C) to rearrangement to produce a compound of Formula (D-1):

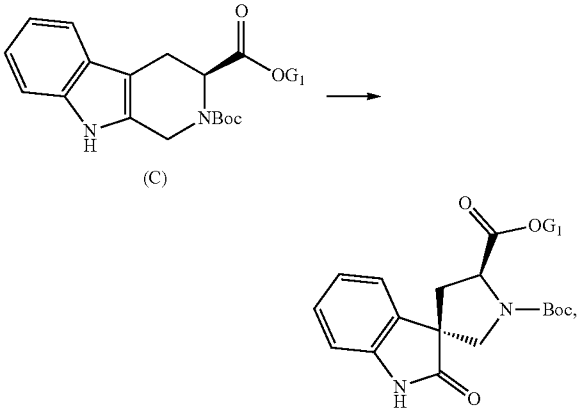

(C)

(D-1)

(d) converting the compound of Formula (D-1) to a compound (e-1):

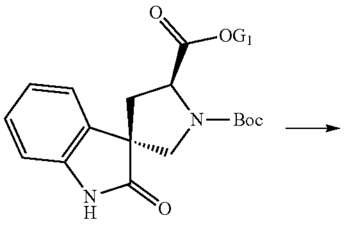

(D-1)

-continued

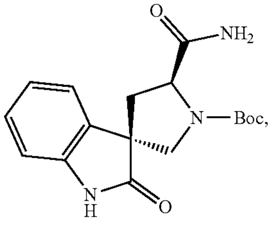

(e-1)

(e) converting Compound (e-1) to a compound of Formula (F-1):

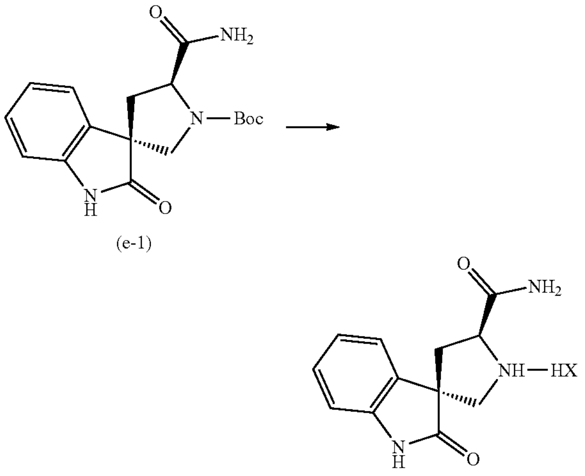

(e-1)

(F-1)

wherein X is an anion selected from $Cl^-$, $Br^-$, and $CF_3CO_2^-$;

(f) reacting the compound of Formula (F-1) with a compound of Formula (K):

(K)

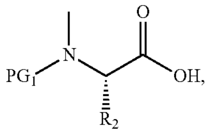

wherein $PG_1$ is selected from -Boc, -Cbz, —C(O) OMe, —C(O) OEt, -Fmoc, -Troc, -Moz, -Pnz, and -Teoc; to produce a compound of Formula (L):

(L)

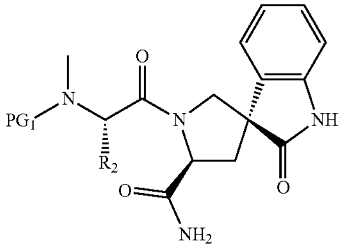

(g) converting the compound of Formula (L), optionally in the presence of a suitable acid, to a compound of Formula (M) or a salt thereof:

(M)

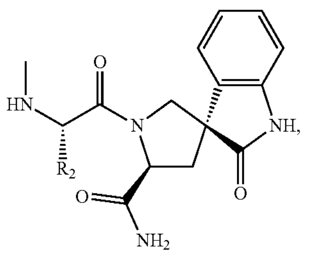

(h) Reacting the compound of Formula (M) or salt thereof with a compound of Formula (J):

(J)

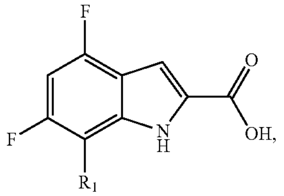

wherein $R_1$ is as previously defined to provide a compound of Formula (N):

(N)

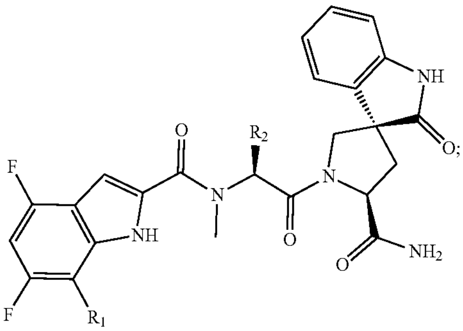

and (i) converting the compound of Formula (N) to the compound of Formula (A).

10. The process of claim 9, wherein $R_1$ is fluorine and $R_2$ is isobutyl.

11. The process of claim 2, wherein $G_1$ is methyl, X is $Cl^-$ and $PG_1$ is Cbz.

12. A process for producing a compound of Formula (A), (A)

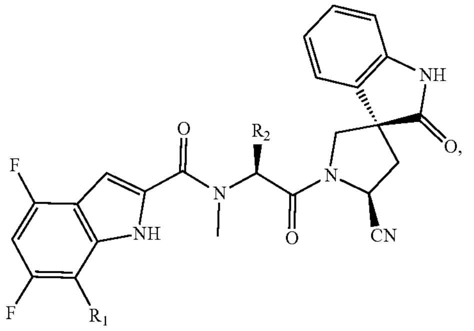

wherein $R_1$ is selected from the group consisting of hydrogen, Cl, F, optionally substituted methyl, and optionally substituted methoxy; and $R_2$ is selected from the group consisting of hydrogen, optionally substituted-$C_1$-$C_6$ alkyl, and optionally substituted-$C_1$-$C_6$ alkylaryl, said process comprising the steps of a) reacting a compound of Formula (W), with formaldehyde, to produce a compound of Formula (B):

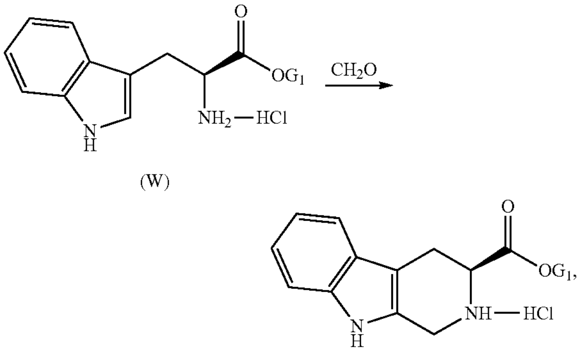

(W)

(B)

wherein $G_1$ is $C_1$-$C_6$-alkyl or aryl;

b) converting the compound of Formula (B) to a compound of Formula (C):

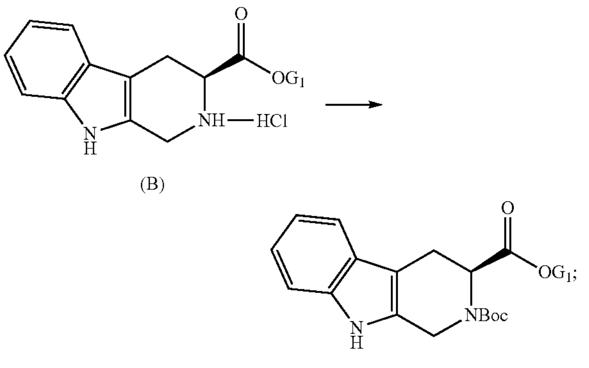

(B)

(C)

c) subjecting the compound of Formula (C) to rearrangement to produce a compound of Formula (D-1):

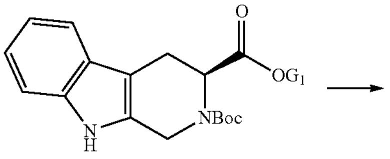

(C)

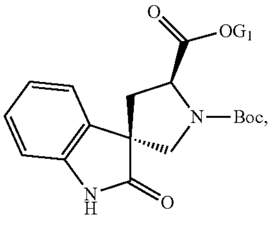

(D-1)

d) converting the compound of Formula (D-1) to compound (e-1):

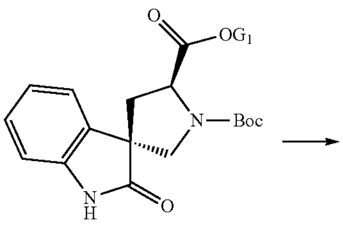

(D-1)

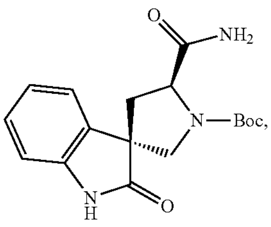

(e-1)

e) converting compound (e-1) to a compound of Formula (F-1):

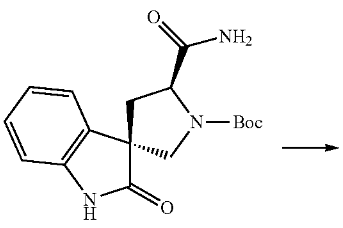

(e-1)

-continued

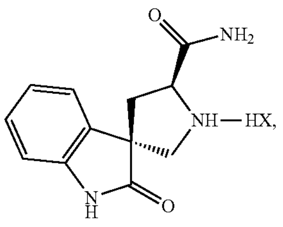

(F-1)

wherein X is an anion, selected from the group consisting of $Cl^-$, $Br^-$, and $CF_3CO_2^-$;

f) reacting the compound of Formula (F-1) with a compound of Formula (K):

(K)

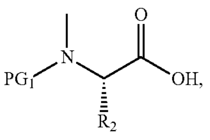

wherein $PG_1$ is selected from the group consisting of -Boc, -Cbz, —C(O) OMe, —C(O) OEt, -Fmoc, -Troc, -Moz, -Pnz, and -Teoc, to produce Compound of Formula (L):

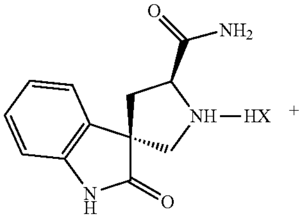

(F-1)

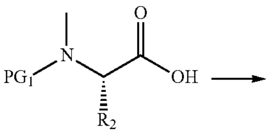

(K)

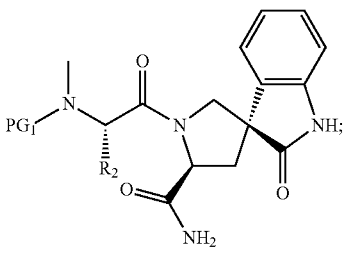

(L)

g) converting the compound of Formula (L), optionally in the presence of a suitable acid, to a compound of Formula (M) or a salt thereof:

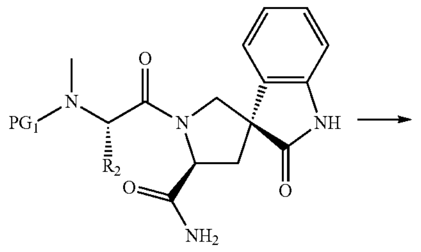

(L)

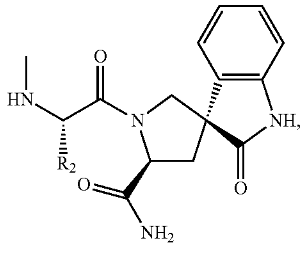

(M)

alternatively, with a suitable acid, converting Compound of Formula (L) to a salt form of Compound of Formula (M);

(J-1) reducing a compound of Formula (G-a) to produce a compound of Formula (G-b):

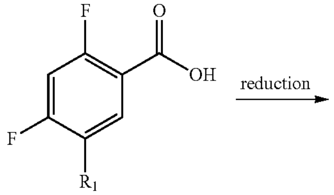

(G-a)

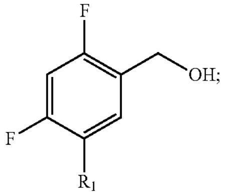

(G-b)

(J-2) oxidizing the compound of Formula (G-b) to produce a compound of Formula (G):

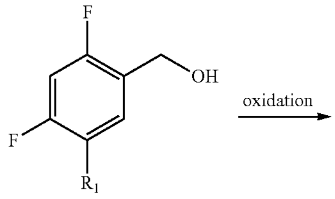

(G-b)

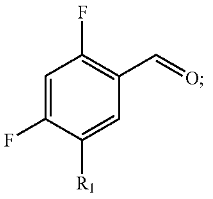

(G)

(J-2a) reacting the compound of Formula (G) with sodium bisulfite to produce a compound of Formula (G-c):

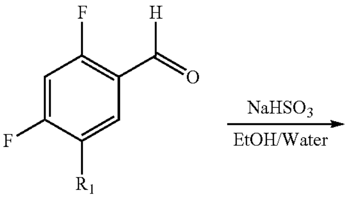

(G)

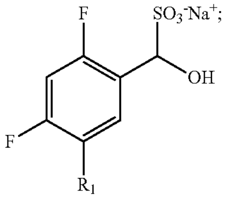

(G-c)

(J-2b) reacting the compound of Formula (G-c) with a base to produce a compound of Formula (G):

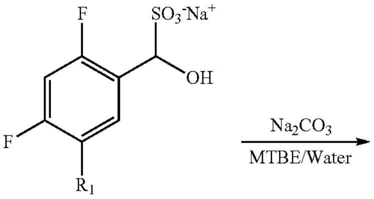

(G-c)

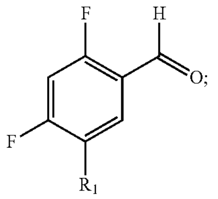

(G)

(J-3) reacting the compound of Formula (G) with a compound of Formula (G-1), in the presence of a base to produce a compound of Formula (H):

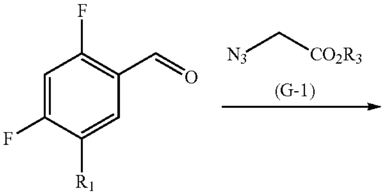

(G)

-continued

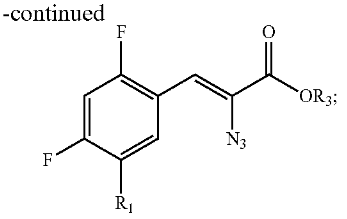

(H)

wherein $R_3$ is methyl, ethyl, or benzyl;

(J-4) converting the compound of Formula (H) to a compound of Formula (I) via Hemetsberger indole cyclization:

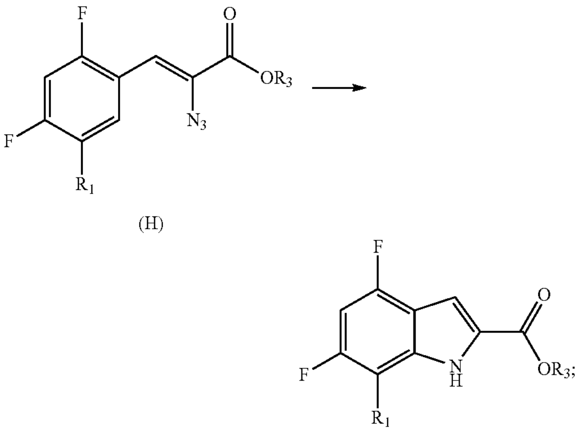

(H)

(I)

(J-5) reacting the compound (I) with a base to yield a compound of Formula (J), or a salt thereof:

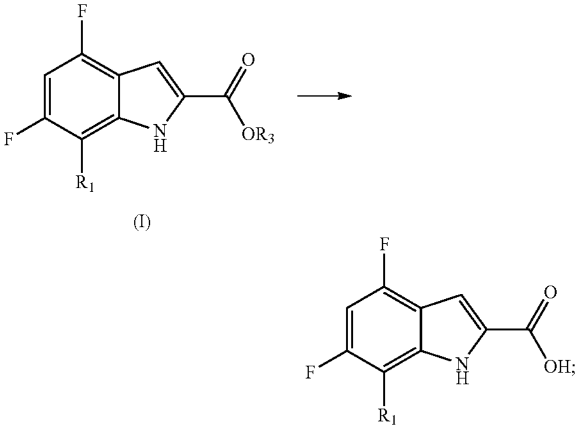

(I)

(J)

h) reacting the compound of Formula (M) or salt thereof with compound of Formula (J) or salt thereof (J)

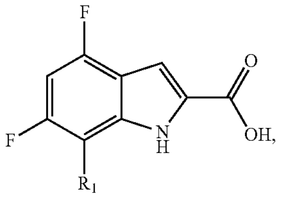

wherein $R_1$ is as previously defined; to provide a compound of Formula (N):

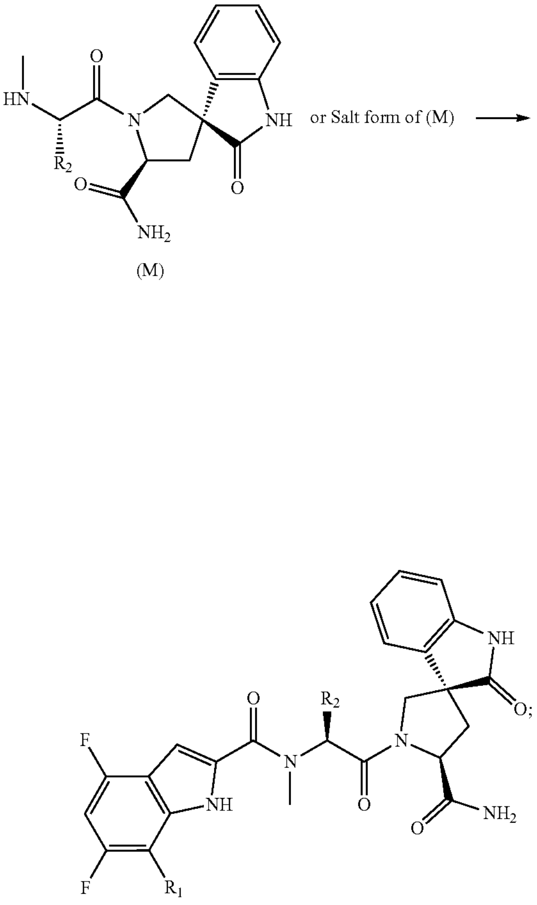

(M)

(N)

and i) converting the compound of Formula (N) to the compound of Formula (A).

* * * * *